(12) United States Patent
Buechler et al.

(10) Patent No.: US 6,420,113 B1
(45) Date of Patent: Jul. 16, 2002

(54) CHIMERIC POLYCLONAL ANTIBODIES

(75) Inventors: Joe Buechler, Carlsbad; Gunars Valkirs, Escondido; Jeff Gray, Solana Beach, all of CA (US)

(73) Assignee: Biosite Diagnostics, Inc., San Diego, CA (US)

( * ) Notice: Subject to any disclaimer, the term of this patent is extended or adjusted under 35 U.S.C. 154(b) by 0 days.

(21) Appl. No.: 09/410,903

(22) Filed: Oct. 2, 1999

Related U.S. Application Data

(63) Continuation-in-part of application No. PCT/US98/06704, filed on Apr. 3, 1998, which is a continuation-in-part of application No. 08/835,159, filed on Apr. 4, 1997, which is a continuation-in-part of application No. 08/832,985, filed on Apr. 4, 1997, now Pat. No. 6,057,098.

(51) Int. Cl.[7] .......................... C12Q 1/68; C12P 21/06; C07H 21/02
(52) U.S. Cl. .......................... 435/6; 435/7.1; 435/69.1; 435/320.1; 435/DIG. 1; 435/DIG. 2; 435/DIG. 3; 435/DIG. 4; 435/DIG. 14; 435/DIG. 17; 536/23.1; 536/23.53
(58) Field of Search .............................. 435/6, 7.1, 7.8, 435/91.4, 471, 489, 69.1, 69.6, 320.1, DIG. 1, DIG. 2, DIG. 3, DIG. 4, DIG. 14, DIG. 17; 536/23.1, 23.53

*Primary Examiner*—Padmashri Ponnaluri
(74) *Attorney, Agent, or Firm*—Townsend and Townsend and Crew LLP

(57) ABSTRACT

The invention is directed to production of chimeric antibodies using display screening methods. The invention is based in part on two related but self-sufficient improvements in conventional display methods. The first improvement provides methods of enriching conventional display libraries for members displaying more than one copy of a polypeptide prior to affinity screening of such libraries with a target of interest. These methods can achieve diverse populations in which the vast majority of members retaining full-length coding sequences encode polypeptides having specific affinity for the target. In a second aspect, the invention provides methods of subcloning nucleic acids encoding displayed polypeptides of enriched libraries from a display vector to an expression vector without the need for clonal isolation of individual members. These methods can be used to produce polyclonal libraries of chimeric antibodies for use, e.g., as diagnostic or therapeutic reagents.

12 Claims, 7 Drawing Sheets

| 5' PCR HEAVY CHAIN OLIGOS FOR ANTIBODIES | |
|---|---|
| OLIGO # | 5' TO 3' SEQUENCE |
| 185 | TT ACC CCT GTG GCA AAA GCC GAG GTG CAG CTT CAG GAG TCA GG |
| 186 | TT ACC CCT GTG GCA AAA GCC CAG GTC CAG CTG CAG CAG TCT GG |
| 188 | TT ACC CCT GTG GCA AAA GCC GAA GTG CAG CTG GTG GAG TCT GG |
| 187 | TT ACC CCT GTG GCA AAA GCC GAG GTG AAG CTG GTG GAA TCT GG |
| 18 | TT ACC CCT GTG GCA AAA GCC CAG GTG CAG CTG AAG GAG TCA GG |
| 19 | TT ACC CCT GTG GCA AAA GCC CAG GTT ACG CTG AAA GAG TCT GG |
| 48 | TT ACC CCT GTG GCA AAA GCC GAG GTG AAG CTG GAT GAG ACT GG |
| 49 | TT ACC CCT GTG GCA AAA GCC GAG GTA AAG CTT CTC GAG TCT GG |
| 50 | TT ACC CCT GTG GCA AAA GCC GAA ATC AGA CTG GTG GAA TCT GG |
| 53 | TT ACC CCT GTG GCA AAA GCC GAA GTG AAG CTG GTG GAG TCT GA |
| 64 | TT ACC CCT GTG GCA AAA GCC CAG GTT CAG CTG CAA CAG TCT GA |
| 66 | TT ACC CCT GTG GCA AAA GCC GAG ATC CAG CTG CAG CAG TCT GG |
| 67 | TT ACC CCT GTG GCA AAA GCC GAA GTG ATC CTG GTG GAG TCT GG |
| 68 | TT ACC CCT GTG GCA AAA GCC GAG GTG CAG CCT GTT GAG TCT GG |
| 69 | TT ACC CCT GTG GCA AAA GCC GAC GTG AAG CAT ATG GAG TCT GG |
| 70 | TT ACC CCT GTG GCA AAA GCC GAA GTG AAG CTT GAG GAG TCT GG |
| 71 | TT ACC CCT GTG GCA AAA GCC GAG GTC CAG CTT CAG CAG TCA GG |
| 73 | TT ACC CCT GTG GCA AAA GCC CAG GTC CAG CTG CAG CAG TCT AG |
| 74 | TT ACC CCT GTG GCA AAA GCC CAG GTC CAG CTG CAG CAG TCT CG |
| 75 | TT ACC CCT GTG GCA AAA GCC GAG GTT CAG CTG CAG CAG TCT GT |
| 124 | TT ACC CCT GTG GCA AAA GCC CAG GTC CAA CTG CAG CAG CCT GG |
| 125 | TT ACC CCT GTG GCA AAA GCC GAG GTT CAG CTG CAG CAG TCT GG |
| 126 | TT ACC CCT GTG GCA AAA GCC GAG GTC CAG CTG CAA CAA TCT GG |
| 127 | TT ACC CCT GTG GCA AAA GCC CAG GTC CAC GTG AAG CAG TCT GG |
| 204 | TT ACC CCT GTG GCA AAA GCC GAT GTG CAG CTT CAG GAG TCG GG |
| 205 | TT ACC CCT GTG GCA AAA GCC CAA GTT ACT CTA AAA GAG TCT GG |
| 207 | TT ACC CCT GTG GCA AAA GCC GAA GTG CAG CTG TTG GAG ACT GG |
| 51 | TT ACC CCT GTG GCA AAA GCC CAG ATC CAG TTG GTG CAA TCT GG |
| 63 | TT ACC CCT GTG GCA AAA GCC GAT GTG AAC TTG GAA GTG TCT GG |
| 72 | TT ACC CCT GTG GCA AAA GCC CAG GCT TAT CTA CAG CAG TCT GG |
| 206 | TT ACC CCT GTG GCA AAA GCC CAG GTC CAA GTG CAG CAG CCT GG |
| 208 | TT ACC CCT GTG GCA AAA GCC GAA GTG CAG CTG GTG GAG ACT GC |
| 526 | TT ACC CCT GTG GCA AAA GCC GAC GTG CAG GTG GTG GAG TCT GG |

*FIG. 1*

| PCR KAPPA CHAIN OLIGOS FOR ANTIBODIES | |
|---|---|
| OLIGO # | 5' TO 3' SEQUENCE |
| 96 | CT GCC CAA CCA GCC ATG GCC GAT GTT TTG ATG ACC CAA ACT CC |
| 97 | CT GCC CAA CCA GCC ATG GCC GAC ATC CAG ATG ACC CAG TCT CC |
| 98 | CT GCC CAA CCA GCC ATG GCC GAT ATC CAG ATG ACA CAG ACT AC |
| 99 | CT GCC CAA CCA GCC ATG GCC GAC ATT GTG ATG ACC CAG TCT CC |
| 128 | CT GCC CAA CCA GCC ATG GCC AAC ATT GTG CTG ACC CAA TCT CC |
| 129 | CT GCC CAA CCA GCC ATG GCC GAT GTT GTG ATG ACC CAA ACT CC |
| 189 | CT GCC CAA CCA GCC ATG GCC GAA ATT GTG CTC ACC CAG TCT CC |
| 190 | CT GCC CAA CCA GCC ATG GCC AGT ATT GTG ATG ACC CAG ACT CC |
| 13 | CT GCC CAA CCA GCC ATG GCC GAT ATT GTG CTA ACT CAG TCT CC |
| 17 | CT GCC CAA CCA GCC ATG GCC CAA ATT GTT CTC ACC CAG TCT CC |
| 38 | CT GCC CAA CCA GCC ATG GCC GAC ATT CAG CTG ACC CAG TCT CC |
| 39 | CT GCC CAA CCA GCC ATG GCC GAT ATT GTG ATG ACC CAG GCT GC |
| 40 | CT GCC CAA CCA GCC ATG GCC GAC CTT GTG CTG ACA CAG TCT CC |
| 41 | CT GCC CAA CCA GCC ATG GCC GAA AAT GTG CTC ACC CAG TCT CC |
| 42 | CT GCC CAA CCA GCC ATG GCC GAA ACA ACT GTG ACC CAG TCT CC |
| 43 | CT GCC CAA CCA GCC ATG GCC GAT GCT GTG ATG ACC CAG ATT CC |
| 44 | CT GCC CAA CCA GCC ATG GCC GAC ATC TTG CTG ACT CAG TCT CC |
| 45 | CT GCC CAA CCA GCC ATG GCC GAT GTT GTG ATA ACT CAG GAT GA |
| 46 | CT GCC CAA CCA GCC ATG GCC GAT GTT GTG GTG ACT CAA ACT CC |
| 47 | CT GCC CAA CCA GCC ATG GCC AAC ATT GTG ATG GCC TGG TCT CC |
| 54 | CT GCC CAA CCA GCC ATG GCC TCA TTA TTG CAG GTG CTT GTG GG |
| 55 | CT GCC CAA CCA GCC ATG GCC GAT ATT GTG ATA ACC CAG GAT GA |
| 56 | CT GCC CAA CCA GCC ATC GCC GAC ATT GTG ATG ACC CAG TCT CA |
| 57 | CT GCC CAA CCA GCC ATG GCC GAA ATG GTT CTC ACC CAG TCT CC |
| 58 | CT GCC CAA CCA GCC ATG GCC GAT GTT GTG CTG ACC CAA ACT CC |
| 59 | CT GCC CAA CCA GCC ATG GCC GAC GTT GTG ATG TCA CAG TCT CC |
| 60 | CT GCC CAA CCA GCC ATG GCC GAC ATT GTG ACG TCA CAG TCT CC |
| 61 | CT GCC CAA CCA GCC ATG GCC CAA GTT GTT CTC ACC CAG TCT CC |
| 62 | CT GCC CAA CCA GCC ATG GCC GAC GTC CAG ATA ACC CAG TCT CC |

| PCR OLIGO FOR HC AND K ANTIBODIES | |
|---|---|
| 1 HC | GA TGG GGG TGT CGT TTT GGC |
| 2 K | AC AGT TGG TGC AGC ATC AGC |

FIG. 2

* represents 19 base pairs at the 5'-end of the tetracycline promoter removed by HinDIII digestion

SEQUENCE LISTING

<160> NUMBER OF SEQ ID NOS: 100

<210> SEQ ID NO 1
<211> LENGTH: 43
<212> TYPE: DNA
<213> ORGANISM: Artificial Sequence
<220> FEATURE:
<223> OTHER INFORMATION: oligo 185

<400> SEQUENCE: 1
ttacccctgt ggcaaaagcc gaggtgcagc ttcaggagtc agg         43

<210> SEQ ID NO 2
<211> LENGTH: 43
<212> TYPE: DNA
<213> ORGANISM: Artificial Sequence
<220> FEATURE:
<223> OTHER INFORMATION: oligo 186

<400> SEQUENCE: 2
ttacccctgt ggcaaaagcc caggtccagc tgcagcagtc tgg         43

<210> SEQ ID NO 3
<211> LENGTH: 43
<212> TYPE: DNA
<213> ORGANISM: Artificial Sequence
<220> FEATURE:
<223> OTHER INFORMATION: oligo 188

<400> SEQUENCE: 3
ttacccctgt ggcaaaagcc gaagtgcagc tggtggagtc tgg         43

<210> SEQ ID NO 4
<211> LENGTH: 43
<212> TYPE: DNA
<213> ORGANISM: Artificial Sequence
<220> FEATURE:
<223> OTHER INFORMATION: oligo 187

<400> SEQUENCE: 4
ttacccctgt ggcaaaagcc gaggtgaagc tggtggaatc tgg         43

<210> SEQ ID NO 5
<211> LENGTH: 43
<212> TYPE: DNA
<213> ORGANISM: Artificial Sequence
<220> FEATURE:
<223> OTHER INFORMATION: oligo 18

<400> SEQUENCE: 5
ttacccctgt ggcaaaagcc caggtgcagc tgaaggagtc agg         43

<210> SEQ ID NO 6
<211> LENGTH: 43
<212> TYPE: DNA
<213> ORGANISM: Artificial Sequence
<220> FEATURE:
<223> OTHER INFORMATION: oligo 19

<400> SEQUENCE: 6
ttacccctgt ggcaaaagcc caggttacgc tgaaagagtc tgg         43

<210> SEQ ID NO 7
<211> LENGTH: 43

```
<212> TYPE: DNA
<213> ORGANISM: Artificial Sequence
<220> FEATURE:
<223> OTHER INFORMATION: oligo 48

<400> SEQUENCE: 7
ttacccctgt ggcaaaagcc gaggtgaagc tggatgagac tgg              43

<210> SEQ ID NO 8
<211> LENGTH: 43
<212> TYPE: DNA
<213> ORGANISM: Artificial Sequence
<220> FEATURE:
<223> OTHER INFORMATION: oligo 49

<400> SEQUENCE: 8
ttacccctgt ggcaaaagcc gaggtaaagc ttctcgagtc tgg              43

<210> SEQ ID NO 9
<211> LENGTH: 43
<212> TYPE: DNA
<213> ORGANISM: Artificial Sequence
<220> FEATURE:
<223> OTHER INFORMATION: oligo 50

<400> SEQUENCE: 9
ttacccctgt ggcaaaagcc gaaatgagac tggtggaatc tgg              43

<210> SEQ ID NO 10
<211> LENGTH: 43
<212> TYPE: DNA
<213> ORGANISM: Artificial Sequence
<220> FEATURE:
<223> OTHER INFORMATION: oligo 53

<400> SEQUENCE: 10
ttacccctgt ggcaaaagcc gaagtgaagc tggtggagtc tga              43

<210> SEQ ID NO 11
<211> LENGTH: 43
<212> TYPE: DNA
<213> ORGANISM: Artificial Sequence
<220> FEATURE:
<223> OTHER INFORMATION: oligo 64

<400> SEQUENCE: 11
ttacccctgt ggcaaaagcc caggttcagc tgcaacagtc tga              43

<210> SEQ ID NO 12
<211> LENGTH: 43
<212> TYPE: DNA
<213> ORGANISM: Artificial Sequence
<220> FEATURE:
<223> OTHER INFORMATION: oligo 66

<400> SEQUENCE: 12
ttacccctgt ggcaaaagcc gagatccagc tgcagcagtc tgg              43

<210> SEQ ID NO 13
<211> LENGTH: 43
<212> TYPE: DNA
<213> ORGANISM: Artificial Sequence
<220> FEATURE:
<223> OTHER INFORMATION: oligo 67

<400> SEQUENCE: 13
```

```
ttaccccctgt ggcaaaagcc gaagtgatgc tggtggagtc tgg          43

<210> SEQ ID NO 14
<211> LENGTH: 43
<212> TYPE: DNA
<213> ORGANISM: Artificial Sequence
<220> FEATURE:
<223> OTHER INFORMATION: oligo 68

<400> SEQUENCE: 14 ttaccccctgt ggcaaaagcc gaggtgcagc ctgttgagtc tgg          43

<210> SEQ ID NO 15
<211> LENGTH: 43
<212> TYPE: DNA
<213> ORGANISM: Artificial Sequence
<220> FEATURE:
<223> OTHER INFORMATION: oligo 69

<400> SEQUENCE: 15 ttaccccctgt ggcaaaagcc gacgtgaagc atatggagtc tgg          43

<210> SEQ ID NO 16
<211> LENGTH: 43
<212> TYPE: DNA
<213> ORGANISM: Artificial Sequence
<220> FEATURE:
<223> OTHER INFORMATION: oligo 70

<400> SEQUENCE: 16 ttaccccctgt ggcaaaagcc gaagtgaagc ttgaggagtc tgg          43

<210> SEQ ID NO 17
<211> LENGTH: 43
<212> TYPE: DNA
<213> ORGANISM: Artificial Sequence
<220> FEATURE:
<223> OTHER INFORMATION: oligo 71

<400> SEQUENCE: 17 ttaccccctgt ggcaaaagcc gaggtccagc ttcagcagtc agg          43

<210> SEQ ID NO 18
<211> LENGTH: 43
<212> TYPE: DNA
<213> ORGANISM: Artificial Sequence
<220> FEATURE:
<223> OTHER INFORMATION: oligo 73

<400> SEQUENCE: 18 ttaccccctgt ggcaaaagcc caggtccagc tgcagcagtc tag          43

<210> SEQ ID NO 19
<211> LENGTH: 43
<212> TYPE: DNA
<213> ORGANISM: Artificial Sequence
<220> FEATURE:
<223> OTHER INFORMATION: oligo 74

<400> SEQUENCE: 19 ttaccccctgt ggcaaaagcc caggtccagc tgcagcagtc tcg          43

<210> SEQ ID NO 20
<211> LENGTH: 43
<212> TYPE: DNA
<213> ORGANISM: Artificial Sequence
```

```
<220> FEATURE:
<223> OTHER INFORMATION: oligo 75

<400> SEQUENCE: 20
ttacccctgt ggcaaaagcc gaggttcagc tgcagcagtc tgt                    43

<210> SEQ ID NO 21
<211> LENGTH: 43
<212> TYPE: DNA
<213> ORGANISM: Artificial Sequence
<220> FEATURE:
<223> OTHER INFORMATION: oligo 124

<400> SEQUENCE: 21
ttacccctgt ggcaaaagcc caggtccaac tgcagcagcc tgg                    43

<210> SEQ ID NO 22
<211> LENGTH: 43
<212> TYPE: DNA
<213> ORGANISM: Artificial Sequence
<220> FEATURE:
<223> OTHER INFORMATION: oligo 125

<400> SEQUENCE: 22
ttacccctgt ggcaaaagcc gaggttcagc tgcagcagtc tgg                    43

<210> SEQ ID NO 23
<211> LENGTH: 43
<212> TYPE: DNA
<213> ORGANISM: Artificial Sequence
<220> FEATURE:
<223> OTHER INFORMATION: oligo 126

<400> SEQUENCE: 23
ttacccctgt ggcaaaagcc gaggtccagc tgcaacaatc tgg                    43

<210> SEQ ID NO 24
<211> LENGTH: 43
<212> TYPE: DNA
<213> ORGANISM: Artificial Sequence
<220> FEATURE:
<223> OTHER INFORMATION: oligo 127

<400> SEQUENCE: 24
ttacccctgt ggcaaaagcc caggtccacg tgaagcagtc tgg                    43

<210> SEQ ID NO 25
<211> LENGTH: 43
<212> TYPE: DNA
<213> ORGANISM: Artificial Sequence
<220> FEATURE:
<223> OTHER INFORMATION: oligo 204

<400> SEQUENCE: 25
ttacccctgt ggcaaaagcc gatgtgcagc ttcaggagtc ggg                    43

<210> SEQ ID NO 26
<211> LENGTH: 43
<212> TYPE: DNA
<213> ORGANISM: Artificial Sequence
<220> FEATURE:
<223> OTHER INFORMATION: oligo 205

<400> SEQUENCE: 26
ttacccctgt ggcaaaagcc caagttactc taaaagagtc tgg                    43
```

<210> SEQ ID NO 27
<211> LENGTH: 43
<212> TYPE: DNA
<213> ORGANISM: Artificial Sequence
<220> FEATURE:
<223> OTHER INFORMATION: oligo 207

<400> SEQUENCE: 27
ttacccctgt ggcaaaagcc gaagtgcagc tgttggagac tgg    43

<210> SEQ ID NO 28
<211> LENGTH: 43
<212> TYPE: DNA
<213> ORGANISM: Artificial Sequence
<220> FEATURE:
<223> OTHER INFORMATION: oligo 51

<400> SEQUENCE: 28
ttacccctgt ggcaaaagcc cagatccagt tggtgcaatc tgg    43

<210> SEQ ID NO 29
<211> LENGTH: 43
<212> TYPE: DNA
<213> ORGANISM: Artificial Sequence
<220> FEATURE:
<223> OTHER INFORMATION: oligo 63

<400> SEQUENCE: 29
ttacccctgt ggcaaaagcc gatgtgaact ggaagtgtc tgg    43

<210> SEQ ID NO 30
<211> LENGTH: 43
<212> TYPE: DNA
<213> ORGANISM: Artificial Sequence
<220> FEATURE:
<223> OTHER INFORMATION: oligo 72

<400> SEQUENCE: 30
ttacccctgt ggcaaaagcc caggcttatc tacagcagtc tgg    43

<210> SEQ ID NO 31
<211> LENGTH: 43
<212> TYPE: DNA
<213> ORGANISM: Artificial Sequence
<220> FEATURE:
<223> OTHER INFORMATION: oligo 206

<400> SEQUENCE: 31
ttacccctgt ggcaaaagcc caggtccaag tgcagcagcc tgg    43

<210> SEQ ID NO 32
<211> LENGTH: 43
<212> TYPE: DNA
<213> ORGANISM: Artificial Sequence
<220> FEATURE:
<223> OTHER INFORMATION: oligo 208

<400> SEQUENCE: 32
ttacccctgt ggcaaaagcc gaagtgcagc tggtggagac tgc    43

<210> SEQ ID NO 33
<211> LENGTH: 43
<212> TYPE: DNA
<213> ORGANISM: Artificial Sequence
<220> FEATURE:
<223> OTHER INFORMATION: oligo 526

<400> SEQUENCE: 33
ttacccctgt ggcaaaagcc gacgtgcagg tggtggagtc tgg          43

<210> SEQ ID NO 34
<211> LENGTH: 43
<212> TYPE: DNA
<213> ORGANISM: Artificial Sequence
<220> FEATURE:
<223> OTHER INFORMATION: oligo 96

<400> SEQUENCE: 34
ctgcccaacc agccatggcc gatgttttga tgacccaaac tcc          43

<210> SEQ ID NO 35
<211> LENGTH: 43
<212> TYPE: DNA
<213> ORGANISM: Artificial Sequence
<220> FEATURE:
<223> OTHER INFORMATION: oligo 97

<400> SEQUENCE: 35
ctgcccaacc agccatggcc gacatccaga tgacccagtc tcc          43

<210> SEQ ID NO 36
<211> LENGTH: 43
<212> TYPE: DNA
<213> ORGANISM: Artificial Sequence
<220> FEATURE:
<223> OTHER INFORMATION: oligo 98

<400> SEQUENCE: 36
ctgcccaacc agccatggcc gatatccaga tgacacagac tac          43

<210> SEQ ID NO 37
<211> LENGTH: 43
<212> TYPE: DNA
<213> ORGANISM: Artificial Sequence
<220> FEATURE:
<223> OTHER INFORMATION: oligo 99

<400> SEQUENCE: 37
ctgcccaacc agccatggcc gacattgtga tgacccagtc tcc          43

<210> SEQ ID NO 38
<211> LENGTH: 43
<212> TYPE: DNA
<213> ORGANISM: Artificial Sequence
<220> FEATURE:
<223> OTHER INFORMATION: oligo 128

<400> SEQUENCE: 38
ctgcccaacc agccatggcc aacattgtgc tgacccaatc tcc          43

<210> SEQ ID NO 39
<211> LENGTH: 43
<212> TYPE: DNA
<213> ORGANISM: Artificial Sequence
<220> FEATURE:
<223> OTHER INFORMATION: oligo 129

<400> SEQUENCE: 39
ctgcccaacc agccatggcc gatgttgtga tgacccaaac tcc          43

<210> SEQ ID NO 40

```
<211> LENGTH: 43
<212> TYPE: DNA
<213> ORGANISM: Artificial Sequence
<220> FEATURE:
<223> OTHER INFORMATION: oligo 189

<400> SEQUENCE: 40
ctgcccaacc agccatggcc gaaattgtgc tcacccagtc tcc            43

<210> SEQ ID NO 41
<211> LENGTH: 43
<212> TYPE: DNA
<213> ORGANISM: Artificial Sequence
<220> FEATURE:
<223> OTHER INFORMATION: oligo 190

<400> SEQUENCE: 41
ctgcccaacc agccatggcc agtattgtga tgacccagac tcc            43

<210> SEQ ID NO 42
<211> LENGTH: 43
<212> TYPE: DNA
<213> ORGANISM: Artificial Sequence
<220> FEATURE:
<223> OTHER INFORMATION: oligo 13

<400> SEQUENCE: 42
ctgcccaacc agccatggcc gatattgtgc taactcagtc tcc            43

<210> SEQ ID NO 43
<211> LENGTH: 43
<212> TYPE: DNA
<213> ORGANISM: Artificial Sequence
<220> FEATURE:
<223> OTHER INFORMATION: oligo 17

<400> SEQUENCE: 43
ctgcccaacc agccatggcc caaattgttc tcacccagtc tcc            43

<210> SEQ ID NO 44
<211> LENGTH: 43
<212> TYPE: DNA
<213> ORGANISM: Artificial Sequence
<220> FEATURE:
<223> OTHER INFORMATION: oligo 38

<400> SEQUENCE: 44
ctgcccaacc agccatggcc gacattcagc tgacccagtc tcc            43

<210> SEQ ID NO 45
<211> LENGTH: 43
<212> TYPE: DNA
<213> ORGANISM: Artificial Sequence
<220> FEATURE:
<223> OTHER INFORMATION: oligo 39

<400> SEQUENCE: 45
ctgcccaacc agccatggcc gatattgtga tgacccaggc tgc            43

<210> SEQ ID NO 46
<211> LENGTH: 43
<212> TYPE: DNA
<213> ORGANISM: Artificial Sequence
<220> FEATURE:
<223> OTHER INFORMATION: oligo 40

<400> SEQUENCE: 46
```

-continued ctgcccaacc agccatggcc gaccttgtgc tgacacagtc tcc          43

<210> SEQ ID NO 47
<211> LENGTH: 43
<212> TYPE: DNA
<213> ORGANISM: Artificial Sequence
<220> FEATURE:
<223> OTHER INFORMATION: oligo 41

<400> SEQUENCE: 47
ctgcccaacc agccatggcc gaaaatgtgc tcacccagtc tcc          43

<210> SEQ ID NO 48
<211> LENGTH: 43
<212> TYPE: DNA
<213> ORGANISM: Artificial Sequence
<220> FEATURE:
<223> OTHER INFORMATION: oligo 42

<400> SEQUENCE: 48
ctgcccaacc agccatggcc gaaacaactg tgacccagtc tcc          43

<210> SEQ ID NO 49
<211> LENGTH: 43
<212> TYPE: DNA
<213> ORGANISM: Artificial Sequence
<220> FEATURE:
<223> OTHER INFORMATION: oligo 43

<400> SEQUENCE: 49
ctgcccaacc agccatggcc gatgctgtga tgacccagat tcc          43

<210> SEQ ID NO 50
<211> LENGTH: 43
<212> TYPE: DNA
<213> ORGANISM: Artificial Sequence
<220> FEATURE:
<223> OTHER INFORMATION: oligo 44

<400> SEQUENCE: 50
ctgcccaacc agccatggcc gacatcttgc tgactcagtc tcc          43

<210> SEQ ID NO 51
<211> LENGTH: 43
<212> TYPE: DNA
<213> ORGANISM: Artificial Sequence
<220> FEATURE:
<223> OTHER INFORMATION: oligo 45

<400> SEQUENCE: 51
ctgcccaacc agccatggcc gatgttgtga taactcagga tga          43

<210> SEQ ID NO 52
<211> LENGTH: 43
<212> TYPE: DNA
<213> ORGANISM: Artificial Sequence
<220> FEATURE:
<223> OTHER INFORMATION: oligo 46

<400> SEQUENCE: 52
ctgcccaacc agccatggcc gatgttgtgg tgactcaaac tcc          43

<210> SEQ ID NO 53
<211> LENGTH: 43
<212> TYPE: DNA

```
<213> ORGANISM: Artificial Sequence
<220> FEATURE:
<223> OTHER INFORMATION: oligo 47

<400> SEQUENCE: 53
ctgcccaacc agccatggcc aacattgtga tggcctggtc tcc                    43

<210> SEQ ID NO 54
<211> LENGTH: 43
<212> TYPE: DNA
<213> ORGANISM: Artificial Sequence
<220> FEATURE:
<223> OTHER INFORMATION: oligo 54

<400> SEQUENCE: 54
ctgcccaacc agccatggcc tcattattgc aggtgcttgt ggg                    43

<210> SEQ ID NO 55
<211> LENGTH: 43
<212> TYPE: DNA
<213> ORGANISM: Artificial Sequence
<220> FEATURE:
<223> OTHER INFORMATION: oligo 55

<400> SEQUENCE: 55
ctgcccaacc agccatggcc gatattgtga taacccagga tga                    43

<210> SEQ ID NO 56
<211> LENGTH: 43
<212> TYPE: DNA
<213> ORGANISM: Artificial Sequence
<220> FEATURE:
<223> OTHER INFORMATION: oligo 56

<400> SEQUENCE: 56
ctgcccaacc agccatggcc gacattgtga tgacccagtc tca                    43

<210> SEQ ID NO 57
<211> LENGTH: 43
<212> TYPE: DNA
<213> ORGANISM: Artificial Sequence
<220> FEATURE:
<223> OTHER INFORMATION: oligo 57

<400> SEQUENCE: 57
ctgcccaacc agccatggcc gaaatggttc tcacccagtc tcc                    43

<210> SEQ ID NO 58
<211> LENGTH: 43
<212> TYPE: DNA
<213> ORGANISM: Artificial Sequence
<220> FEATURE:
<223> OTHER INFORMATION: oligo 58

<400> SEQUENCE: 58
ctgcccaacc agccatggcc gatgttgtgc tgacccaaac tcc                    43

<210> SEQ ID NO 59
<211> LENGTH: 43
<212> TYPE: DNA
<213> ORGANISM: Artificial Sequence
<220> FEATURE:
<223> OTHER INFORMATION: oligo 59

<400> SEQUENCE: 59
ctgcccaacc agccatggcc gacgttgtga tgtcacagtc tcc                    43
```

-continued

<210> SEQ ID NO 60
<211> LENGTH: 43
<212> TYPE: DNA
<213> ORGANISM: Artificial Sequence
<220> FEATURE:
<223> OTHER INFORMATION: oligo 60

<400> SEQUENCE: 60
ctgcccaacc agccatggcc gacattgtga cgtcacagtc tcc        43

<210> SEQ ID NO 61
<211> LENGTH: 43
<212> TYPE: DNA
<213> ORGANISM: Artificial Sequence
<220> FEATURE:
<223> OTHER INFORMATION: oligo 61

<400> SEQUENCE: 61
ctgcccaacc agccatggcc caagttgttc tcacccagtc tcc        43

<210> SEQ ID NO 62
<211> LENGTH: 43
<212> TYPE: DNA
<213> ORGANISM: Artificial Sequence
<220> FEATURE:
<223> OTHER INFORMATION: oligo 62

<400> SEQUENCE: 62
ctgcccaacc agccatggcc gacgtccaga taacccagtc tcc        43

<210> SEQ ID NO 63
<211> LENGTH: 20
<212> TYPE: DNA
<213> ORGANISM: Artificial Sequence
<220> FEATURE:
<223> OTHER INFORMATION: oligo 1 HC

<400> SEQUENCE: 63 gatggggtg tcgttttggc                                    20

<210> SEQ ID NO 64
<211> LENGTH: 20
<212> TYPE: DNA
<213> ORGANISM: Artificial Sequence
<220> FEATURE:
<223> OTHER INFORMATION: oligo 2 K

<400> SEQUENCE: 64
acagttggtg cagcatcagc                                   20

<210> SEQ ID NO 65
<211> LENGTH: 70
<212> TYPE: DNA
<213> ORGANISM: Artificial Sequence
<220> FEATURE:
<223> OTHER INFORMATION: oligo to delete CDR1-CDR3 regions of 668-4

<400> SEQUENCE: 65
tatttccagc ttggtccctc tagagttaac gatatcaacg tttatctaat cagcaagaga    60
tggaggcttg                                                            70

<210> SEQ ID NO 66
<211> LENGTH: 70
<212> TYPE: DNA

```
<213> ORGANISM: Artificial Sequence
<220> FEATURE:
<223> OTHER INFORMATION: oligo to delete CDR1-CDR3 regions of 668-4

<400> SEQUENCE: 66
tgaggttcct tgaccccact gcagagtact aggcctctga gctactcagt taggtgattg      60
agtagccagt                                                            70

<210> SEQ ID NO 67
<211> LENGTH: 75
<212> TYPE: DNA
<213> ORGANISM: Artificial Sequence
<220> FEATURE:
<223> OTHER INFORMATION: oligonucleotide 864

<400> SEQUENCE: 67
atctggcaca tcatatggat aagtttcgtg tacaaaatgc cagacctaga ggaattttat      60
ttccagcttg gtccc                                                      75

<210> SEQ ID NO 68
<211> LENGTH: 69
<212> TYPE: DNA
<213> ORGANISM: Artificial Sequence
<220> FEATURE:
<223> OTHER INFORMATION: oligonucleotide 862

<400> SEQUENCE: 68
gtgatggtga tggtgatgga tcggagtacc aggttatcga gccctcgata ttgaggagac      60
ggtgactga                                                             69

<210> SEQ ID NO 69
<211> LENGTH: 17
<212> TYPE: DNA
<213> ORGANISM: Artificial Sequence
<220> FEATURE:
<223> OTHER INFORMATION: oligonucleotide primer 5

<400> SEQUENCE: 69
gcaactgttg ggaaggg                                                    17

<210> SEQ ID NO 70
<211> LENGTH: 20
<212> TYPE: DNA
<213> ORGANISM: Artificial Sequence
<220> FEATURE:
<223> OTHER INFORMATION: oligonucleotide primer 197

<400> SEQUENCE: 70
tcgctgccca accagccatg                                                 20

<210> SEQ ID NO 71
<211> LENGTH: 46
<212> TYPE: DNA
<213> ORGANISM: Artificial Sequence
<220> FEATURE:
<223> OTHER INFORMATION: oligonucleotide 5' PCR primer 869

<400> SEQUENCE: 71
gggaccaagc tggaaataaa acgggctgtg gctgcaccat ctgtct                    46

<210> SEQ ID NO 72
<211> LENGTH: 45
<212> TYPE: DNA
<213> ORGANISM: Artificial Sequence
```

```
<220> FEATURE:
<223> OTHER INFORMATION: oligonucleotide 3' PCR primer 870

<400> SEQUENCE: 72
atctggcaca tcatatggat aagactctcc cctgttgaag ctctt                45

<210> SEQ ID NO 73
<211> LENGTH: 38
<212> TYPE: DNA
<213> ORGANISM: Artificial Sequence
<220> FEATURE:
<223> OTHER INFORMATION: oligonucleotide 5' PCR primer 867

<400> SEQUENCE: 73
tcagtcaccg tctcctcagc ctccaccaag ggcccatc                         38

<210> SEQ ID NO 74
<211> LENGTH: 43
<212> TYPE: DNA
<213> ORGANISM: Artificial Sequence
<220> FEATURE:
<223> OTHER INFORMATION: oligonucleotide 3' PCR primer 876

<400> SEQUENCE: 74
gtgatggtga tggtgatgag atttgggctc tgctttcttg tcc                   43

<210> SEQ ID NO 75
<211> LENGTH: 21
<212> TYPE: DNA
<213> ORGANISM: Artificial Sequence
<220> FEATURE:
<223> OTHER INFORMATION: oligonucleotide primer 885

<400> SEQUENCE: 75
taagagcggt aagagtgcca g                                           21

<210> SEQ ID NO 76
<211> LENGTH: 20
<212> TYPE: DNA
<213> ORGANISM: Artificial Sequence
<220> FEATURE:
<223> OTHER INFORMATION: oligonucleotide 197

<400> SEQUENCE: 76
tcgctgccca accagccatg                                             20

<210> SEQ ID NO 77
<211> LENGTH: 26
<212> TYPE: DNA
<213> ORGANISM: Artificial Sequence
<220> FEATURE:
<223> OTHER INFORMATION: oligonucleotide 938

<400> SEQUENCE: 77
gatgaagaca gatggtgcag ccacag                                      26

<210> SEQ ID NO 78
<211> LENGTH: 29
<212> TYPE: DNA
<213> ORGANISM: Artificial Sequence
<220> FEATURE:
<223> OTHER INFORMATION: oligonucleotide 939

<400> SEQUENCE: 78
gggaagaccg atgggccctt ggtggaggc                                   29
```

```
<210> SEQ ID NO 79
<211> LENGTH: 21
<212> TYPE: DNA
<213> ORGANISM: Artificial Sequence
<220> FEATURE:
<223> OTHER INFORMATION: oligonucleotide 949

<400> SEQUENCE: 79
tttacccctg tggcaaaagc c                                            21

<210> SEQ ID NO 80
<211> LENGTH: 30
<212> TYPE: DNA
<213> ORGANISM: Artificial Sequence
<220> FEATURE:
<223> OTHER INFORMATION: oligonucleotide 950

<400> SEQUENCE: 80
tggatagaca gatgggcccg tcgtggtggc                              30

EQ ID NO 81

211> LENGTH: 69
<212> TYPE: DNA
<213> ORGANISM: Artificial Sequence
<220> FEATURE:
<223> OTHER INFORMATION: oligonucleotide 970

<400> SEQUENCE: 81
gtgataaact accgtaaagc ttatcgatga taagctgtca attagtgatg gtgatggtga  60
     tgagatttg                                                         69

EQ ID N 82

ENGTH: 0
<212> TYPE: PRT
<213> ORGANISM: Artificial Sequence
<220> FEATURE:
<223> OTHER INFORMATION: decapeptide

<400> SEQUENCE: 82

Tyr Pro Tyr Asp Val Pro Asp Tyr Ala Ser
       1               5                  10

EQ ID N 83
<211> LENGTH: 50
<212> TYPE: DNA
<213> ORGANISM: Artificial Sequence
<220> FEATURE:
<223> OTHER INFORMATION: primer A

<400> SEQUENCE: 83
cactcaaccc tatctattaa tgtggaattc aaatggacga agcagggatt           50

EQ ID N 84
<211> LENGTH: 38
<212> TYPE: DNA
<213> ORGANISM: Artificial Sequence
<220> FEATURE:
<223> OTHER INFORMATION: primer B

<400> SEQUENCE: 84
gtaggcaata ggtatttcat cgtttcactc catccaaa                       38

EQ ID N 85
<211> LENGTH: 18
<212> TYPE: DNA
```

<213> ORGANISM: Artificial Sequence
<220> FEATURE:
<223> OTHER INFORMATION: primer C

<400> SEQUENCE: 85

```
    tccgtgccgg ttgtgaag                                              18
```

EQ ID N 86
<211> LENGTH: 18
<212> TYPE: DNA
<213> ORGANISM: Artificial Sequence
<220> FEATURE:
<223> OTHER INFORMATION: primer D

<400> SEQUENCE: 86

```
tacgcgaggc ttgtcagt                                                  18
```

<210> SEQ ID NO 87
<211> LENGTH: 18
<212> TYPE: DNA
<213> ORGANISM: Artificial Sequence
<220> FEATURE:
<223> OTHER INFORMATION: primer E

<400> SEQUENCE: 87

```
ttcatcacta cggtcgtc                                                  18
```

<210> SEQ ID NO 88
<211> LENGTH: 18
<212> TYPE: DNA
<213> ORGANISM: Artificial Sequence
<220> FEATURE:
<223> OTHER INFORMATION: primer F

<400> SEQUENCE: 88

```
gacggcaatg tctgatgc                                                  18
```

<210> SEQ ID NO 89
<211> LENGTH: 42
<212> TYPE: DNA
<213> ORGANISM: Artificial Sequence
<220> FEATURE:
<223> OTHER INFORMATION: primer G

<400> SEQUENCE: 89

```
gatatcaacg tttatctaat caggccatgg ctggttgggc ag                       42
```

<210> SEQ ID NO 90
<211> LENGTH: 20
<212> TYPE: DNA
<213> ORGANISM: Artificial Sequence
<220> FEATURE:
<223> OTHER INFORMATION: primer H

<400> SEQUENCE: 90

```
ggcatcccag ggtcaccatg                                                20
```

<210> SEQ ID NO 91
<211> LENGTH: 20
<212> TYPE: DNA
<213> ORGANISM: Artificial Sequence
<220> FEATURE:
<223> OTHER INFORMATION: primer I

<400> SEQUENCE: 91

```
tcgctgccca accagccatg                                                20
```

<210> SEQ ID NO 92
<211> LENGTH: 69
<212> TYPE: DNA
<213> ORGANISM: Artificial Sequence
<220> FEATURE:
<223> OTHER INFORMATION: primer J

<400> SEQUENCE: 92
gtgataaact accgcattaa agcttatcga tgataagctg tcaattaaga atccctgggc    60
acaattttc                                                           69

<210> SEQ ID NO 93
<211> LENGTH: 89
<212> TYPE: DNA
<213> ORGANISM: Artificial Sequence
<220> FEATURE:
<223> OTHER INFORMATION: primer K

<400> SEQUENCE: 93
agagctgcag aattcagctg atcatctcac caataaaaaa cgcccggcgg caaccgagcg    60
ttctgaacaa atggacgaag cagggattc                                     89

<210> SEQ ID NO 94
<211> LENGTH: 87
<212> TYPE: DNA
<213> ORGANISM: Artificial Sequence
<220> FEATURE:
<223> OTHER INFORMATION: primer L

<400> SEQUENCE: 94
tctctccaag gaagcttaaa aaaaagcccg ctcattaggc gggctagctt aatcaatcat    60
gcatcgtttc actccatcca aaaaaac                                       87

<210> SEQ ID NO 95
<211> LENGTH: 69
<212> TYPE: DNA
<213> ORGANISM: Artificial Sequence
<220> FEATURE:
<223> OTHER INFORMATION: primer M

<400> SEQUENCE: 95
acaggtacga agcttatcga tgataagctg tcaaaccaag gagcttaaaa aaaagcccgc    60
tcattaggc                                                           69

<210> SEQ ID NO 96
<211> LENGTH: 51
<212> TYPE: DNA
<213> ORGANISM: Artificial Sequence
<220> FEATURE:
<223> OTHER INFORMATION: primer N

<400> SEQUENCE: 96
acccgttttt ttggatggag tgaaacgatg cattacctat tgcctacggc a             51

<210> SEQ ID NO 97
<211> LENGTH: 71
<212> TYPE: DNA
<213> ORGANISM: Artificial Sequence
<220> FEATURE:
<223> OTHER INFORMATION: primer O

<400> SEQUENCE: 97

-continued

```
gtgataaact accgcattaa agcttatcga tgataagctg tcaattaaga agcgtagtag        60
tccggaacgt c                                                             71

<210> SEQ ID NO 98
<211> LENGTH: 75
<212> TYPE: DNA
<213> ORGANISM: Artificial Sequence
<220> FEATURE:
<223> OTHER INFORMATION: primer P

<400> SEQUENCE: 98
gtgataaact accgcattaa agcttatcga tgataagctg tcaattagtg atggtgatgg        60
tgatgacaat ccctg                                                         75

<210> SEQ ID NO 99
<211> LENGTH: 51
<212> TYPE: DNA
<213> ORGANISM: Artificial Sequence
<220> FEATURE:
<223> OTHER INFORMATION: primer Q

<400> SEQUENCE: 99
acccgttttt ttggatggag tgaaacgatg tcaggaaaag atgtaaatgt c                 51

<210> SEQ ID NO 100
<211> LENGTH: 89
<212> TYPE: DNA
<213> ORGANISM: Artificial Sequence
<220> FEATURE:
<223> OTHER INFORMATION: primer R

<400> SEQUENCE: 100
gtgataaact accgcattaa agcttatcga tgataagctg tcaattagtg atggtgatgg        60
tgatggtacc atcctcttaa tttcatagc                                          89
```

CHIMERIC POLYCLONAL ANTIBODIES

CROSS-REFERENCES TO RELATED APPLICATIONS

The present application is a continuation-in-part of PCT/US 98/06704, filed, Apr. 3, 1998, which is a continuation-in-part of U.S. Ser. No. 08/835,159, filed Apr. 4, 1997 and U.S. Ser. No. 08/832,985, filed Apr. 4, 1997, (now U.S. Pat. No. 6,057,098) all of which are incorporated by reference in their entirety for all purposes. Related applications Ser. No. 60/0442,292, filed Apr. 4, 1997 and Ser. No. 08/835,159, filed Apr. 4, 1997, are also incorporated by reference in their entirety for all purposes.

BACKGROUND

Over recent years, many publications have reported the use of phage-display technology to produce and screen libraries of polypeptides for binding to a selected target. See, e.g, Cwirla, et al., Proc. Natl. Acad. Sci. USA 87:6378–6382 (1990); Devlin, et al., Science 249:404–406 (1990), Scott & Smith, Science 249:386–388 (1990); Ladner, et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means.

Phage display technology has also been used to produce and screen libraries of heterodimeric proteins, such as Fab fragments. See e.g., Garrard, et al., Bio/Tech 9:1373–1377 (1991). Phage display libraries of Fab fragments are produced by expressing one of the component chains as a fusion with a coat protein, as for display of single-chain polypeptides. The partner antibody chain is expressed in the same cell from the same or a different replicon as the first chain, and assembly occurs within the cell. Thus, a phage-Fab fragment has one antibody chain fused to a phage coat protein so that it is displayed from the outer surface of the phage and the other antibody chain is complexed with the first chain.

In a further expansion of the basic approach, polypeptide libraries have been displayed from replicable genetic packages other than phage. These replicable genetic packages include eukaryotic viruses and bacteria. The principles and strategy are closely analogous to those employed for phage, namely, that nucleic acids encoding antibody chains or other polypeptides to be displayed are inserted into the genome of the package to create a fusion protein between the polypeptides to be screened and an endogenous protein that is exposed on the cell or viral surface. Expression of the fusion protein and transport to the cell surface result in display of polypeptides from the cell or viral surface.

Although conventional display methods have achieved considerable success in isolating antibodies and other polypeptides with specific binding to selected targets, some inefficiencies and limitations remain. In conventional methods, many library members bind nonspecifically to the target or the solid phase bearing the target and are amplified along with specifically bound library members causing poor efficiency at each round of affinity selection. Not only can this waste time and effort in performing many rounds of affinity selection, but members bearing polypeptides having specific affinity are lost at each round. Selection is generally terminated when sufficient rounds of affinity selection have been performed to achieve a significant number of members bearing polypeptides with affinity for a target even though many nonspecifically binding members are still present. Clonal isolates are then picked and tested individually to reduce the risk of losing specific-binding members through further rounds of selection. Clonal isolates shown to bind specifically may then be cloned into an expression work for future analysis, and, large-scale production. Accordingly, only one or a few of library members bearing polypeptides with specific affinity for the target present in the original repertoire are ever isolated.

The present application provides inter alia novel methods that overcome these inefficiencies and difficulties, and produce new diagnostic and therapeutic reagents.

SUMMARY OF THE INVENTION

The invention provides libraries of at least four chimeric antibodies. At least 50% of the antibodies in the library have specific affinity for the same target and no library member constitutes more than 25% of the library. In some libraries, the antibodies are Fab fragments. In some libraries, the antibodies are single-chain antibodies. In some libraries, the antibodies are intact antibodies. Typically, a chimeric antibody light chain comprises a nonhuman light chain variable region and a human light chain constant region. Typically, a chimeric antibody heavy chain comprises a nonhuman heavy chain variable region and a human heavy chain constant region. In some libraries at least some antibodies have light and heavy chain variable regions that are randomly associated.

The invention further provides libraries of at least four different nucleic segments encoding chimeric antibody chains comprising a variable region and a constant region from different species. At least 90% of segments in the library encode chimeric antibody chains showing specific affinity for the same target and no library member constitutes more than 50% of the library. Some such libraries comprise at least four pairs of the different nucleic acid segments, the members of a pair respectively encoding heavy and light chimeric antibody chains, wherein at least 90% of the pairs encode heavy and light chimeric antibody chains that form complexes showing specific affinity for the same target, and no pair of nucleic acid segments constitutes more than 50% of the library. In some libraries, at least 95% of library members encode chimeric antibody chains forming complexes having specific affinity for the target and no member constitutes more than 25% of the library. Some libraries have at least 100 different members. In some libraries, each pair of nucleic acids is expressed as a discistronic transcript.

The invention further provides methods of producing a polypeptide library having affinity for a target. Such methods entail providing a library of replicable genetic packages, wherein a member comprises a replicable genetic package capable of displaying an antibody chain encoded by a genome of the package and the antibody chain varying between members. One then subclones a mixed population of DNA molecules encoding at least four different antibody chains of the library of replicable genetic packages into multiple copies of an expression vector to produce modified forms of the expression vector. One then introduces the modified forms of the expression vector into a host and expressing the antibody chains as chimeric antibody chains in the host, wherein a library of at least four different chimeric antibody chains are expressed, at least 90% of modified forms of the expression vector encode chimeric antibody chains having specific affinity for a target and no modified form of the expression vector constitutes more than 50% of the total forms.

The invention further provides methods of producing an antibody library having affinity for a target as follows. A library of phage is provided in which a member of the library comprises a phage capable of displaying from its outersurface an antibody comprising an antibody heavy chain variable domain complexed with an antibody light chain variable domain, in which either the heavy or light chain variable domain is expressed as a fusion protein with a coat protein of the phage and the heavy and light chain variable domains are encoded by the genome of the phage, and the heavy and light chain varies between members. A mixture of DNA molecules encoding the heavy and light chain variable domains from the phage library members are subcloned into an expression vector to produce modified forms of the expression vector. The modified forms of the expression vector are then into a host and expressed to produce the heavy and light chain variable domains as chimeric heavy and light chains, which complex as chimeric antibodies. The antibodies are released from the host to form an antibody library of at least four antibodies in which at least 90% of modified forms of the expression vector encode antibodies with specific affinity for a target and no modified form of the expression vector constitutes more than 50% of the total forms.

The invention further provides method of enriching a polypeptide display library. Such methods entail providing a library of replicable genetic packages, in which a member comprises a replicable genetic package capable of displaying from its outersurface an antibody chain to be screened and a tag fused to the polypeptide or to a binding partner of the antibody chain, if present, which antibody chain is encoded by a segment of a genome of the package. The antibody chains varies between library members. The number of copies of the antibody chain and/or the binding partner (if present) displayed per library member varies between library members, and the tag is the same in different library members. The antibody chain is a chimeric antibody chain comprising a variable region from a first species and a constant region from a second species. The library is then contacted with a receptor having a specific affinity for the tag under conditions in which library members displaying the antibody chain or the binding partner fused to the tag are bound to immobilized receptor. Library members bound to the immobilized receptor are separated from unbound library members to produce a sublibrary enriched relative to the library for members displaying the antibody chain or the binding partner.

The invention further provides methods of enriching a Fab phage display library. Such methods entail providing a library of phage in which a library member comprises a phage capable of displaying from its outersurface a fusion protein comprising a phage coat protein, a chimeric antibody light or heavy chain comprising a variable region and a constant region from different species, and a tag, wherein in at least some members, the chimeric antibody heavy or light chain is complexed with a partner chimeric antibody heavy or light chain domain chain, comprising a variable region and a constant region from the different species, the complex forming a Fab fragment to be screened, wherein the fusion protein and/or the partner chimeric antibody heavy or light chain are encoded by segment(s) of the genome of the phage, and the number of copies of the fusion protein and the partner chimeric antibody chain displayed per phage vary between library members. The library or a fraction thereof is contacted with a receptor having a specific affinity for the tag whereby library members displaying a copy of the fusion protein are bound to immobilized receptor by bonding between the receptor and the tag. Library members bound to the receptor are separated from unbound library members to produce an sublibrary enriched relative to the library for members displaying the fusion protein.

The invention further provides a method of enrich a phage display library as follows.

A library of phage is provided in which a library member comprises a phage capable of displaying from its outersurface a fusion protein comprising a phage coat protein, and a chimeric antibody heavy or light chain comprising a heavy or light chain variable region from a first species and a heavy or light chain constant region from a second species, wherein in at least some members, the chimeric antibody heavy or light chain is complexed with a partner chimeric antibody heavy or light chain comprising a heavy or light chain variable region from the first species and a heavy or light chain constant region from the second species, the partner being fused to a tag, the complex forming a chimeric Fab fragment to be screened, wherein the fusion protein and/or the partner chimeric antibody heavy or light chain fused to the tag are encoded by segment(s) of the genome of the phage, and the number of copies of the fusion protein and the partner chimeric antibody chain displayed per phage vary between library members. The library or a faction thereof is contacted with a receptor having a specific affinity for the tag under conditions whereby library members displaying the partner chimeric antibody chain are bound to immobilized receptor by binding between the immobilized receptor and the tag. Library members bound to the receptor are separated from unbound library members to produce an sublibrary enriched relative to the library for members displaying the partner chimeric antibody chain.

In another aspect, the invention provides methods of producing a multivalent polypeptide display library. The starting material is a library of replicable genetic packages, such as phage. A member of such a library is capable of displaying from its outer surface a fusion protein comprising a polypeptide to be screened and a tag. The fusion protein is encoded by a segment of a genome of the package. The polypeptides vary between library members, as does the number of copies of the fusion protein displayed per library member. The tag is the same in different library members. The library is contacted with a receptor having a specific affinity for the tag under conditions whereby library members displaying at least two copies of the fusion protein are preferentially bound to immobilized receptor by multivalent bonds between the receptor and the at least two copies of the tag. Library members bound to the immobilized receptor are then separated from unbound library members to produce a sublibrary enriched relative to the library for members displaying at least two copies of the fusion protein.

Polypeptides of particular interest are antibodies, particularly Fab fragments. Multivalent Fab phage display libraries can be produced as follows. The starting material is a library of phage in which a library member comprises a phage capable of displaying from its outer surface a fusion protein comprising a phage coat protein, an antibody light or heavy chain variable domain, and a tag. In at least some members, the antibody heavy or light chain is complexed with a partner antibody heavy or light chain variable domain chain, the complex forming a Fab fragment to be screened. The fusion protein and/or the partner antibody heavy or light chain are encoded by segment(s) of the genome of the phage. The number of copies of the fusion protein and the partner antibody chain displayed per phage vary between library members. The library or a fraction thereof is contacted with a receptor having a specific affinity for the tag under conditions whereby library members displaying at least two copies of the fusion protein are preferentially bound to immobilized receptor by multivalent bonds between the receptor and the at least two copies of the tag. Library members bound to the receptor are then separated from unbound library members to produce a sublibrary enriched relative to the library for members displaying at least two copies of the fusion protein.

An alternative method of producing a multivalent Fab phage display library is as follows. The starting material is a library of phage in which a library member comprises a phage capable of displaying from its outer surface a fusion protein comprising a phage coat protein, and an antibody light or heavy chain variable domain. At least in some members, the antibody light or heavy chain is complexed with a partner antibody heavy or light chain variable domain chain fused to a tag, the complex forming a Fab fragment to be screened. The fusion protein and/or the partner antibody heavy or light chain fused to the tag are encoded by segment(s) of the genome of the phage. The number of copies of the fusion protein and the partner antibody chain displayed per phage vary between library members. The library or a fraction thereof is contacted with a receptor having a specific affinity for the tag under conditions whereby library members displaying at least two copies of the partner antibody chain are preferentially bound to immobilized receptor by multivalent bonds between the immobilized receptor and the at least two copies of the tag. Bound library members are separated from unbound library members to produce an sublibrary enriched relative to the library for members displaying at least two copies of the partner antibody chain.

Having produced a polyvalent phage display library, such as described above, it can be screened by contacting the library with a target lacking specific affinity for the tag moiety(ies) and separating library members bound to the target via their displayed polypeptides from unbound library members.

DNA segments encoding polypeptides having specific affinity for a target can be subcloned in an expression vector, and the polypeptides expressed in host cells. Polypeptides can then, for example, be formulated with diagnostic or therapeutic excipients.

In another aspect, the invention provides libraries of nucleic acid segments encoding polyclonal polypeptides having specific affinity for a target. Such a library comprises least four different nucleic acid segments. At least 90% of segments in the library encode polypeptides showing specific affinity for a target and no library member constitutes more than 50% of the library. In some libraries, at least 95% of library members encode polypeptides having specific affinity for a target and no member constitutes more than 25% of the library. Some libraries have at least 100 different members. In some libraries, the segments are contained in a vector. In some libraries, the segment encode antibody chains. In some libraries, first and second segments are present, respectively encoding antibody heavy chains and partner antibody light chains, which can complex to form a Fab fragment. The first and second segments can be incorporated into the same or different vectors.

The invention further provides cell libraries in which a member cell contains a nucleic acid segment from a nucleic acid library, as described above. Such a library of cells can be propagated under conditions in which the DNA segments are expressed to produce polyclonal polypeptides.

The invention further provides methods of producing polyclonal polypeptides having specific affinity for a target. The starting material for such methods is a library of replicable genetic packages. A member comprises a replicable genetic package capable of displaying a polypeptide to be screened encoded by a genome of the package. The polypeptides vary between members. DNA encoding at least four different polypeptides of the library of replicable genetic packages is subcloned into an expression vector to produce modified forms of the expression vector. The modified forms of the expression vector are introduced into a host and expressed in the host producing at least four different polypeptides. At least 75% of modified forms of the expression vector encode polypeptides having specific affinity for a target and no modified form of the expression vector constitutes more than 50% of the total.

Polypeptides of particular interest are antibodies and these are typically displayed from phage libraries. A typical member of such a library is a phage capable of displaying from its outer surface an antibody comprising an antibody heavy chain variable domain complexed with an antibody light chain variable domain. Either the heavy or light chain variable domain is expressed as a fusion protein with a coat protein of the phage and either the heavy or light chain variable domain or both is/are encoded by the genome of the phage. The heavy and/or light chain varies between members. DNA encoding the heavy and/or light chain variable domains are subcloned from the phage library members into an expression vector to produce modified forms of the expression vector. The modified forms of the expression vector are introduced into a host and expressed to produce antibodies formed by the heavy and light chain variable domains of the phage library in the host. The antibodies are then released from the host to form an antibody library of at least four antibodies. At least 75% of modified forms of the expression vector encode antibodies with specific affinity for a target and no modified form of the expression vector constitutes more than 50% of the total.

Polyclonal libraries of antibodies and other polypeptides produced by the above methods can be incorporated into a diagnostic kit, or formulated for use as a diagnostic or therapeutic reagent.

BRIEF DESCRIPTION OF THE DRAWINGS

FIG. 1: Primers used for amplification of immunoglobulin heavy chains (SEQ ID NOS: 1–33).

FIG. 2: Primers used for amplification of immunoglobulin light chains (SEQ ID NOS: 34–64).

FIG. 3A shows a vector obtained from Ixsys, Inc. and described in Huse, WO 92/06204, which provides the starting material for producing the vectors shown in FIGS. 3B and 3C. FIGS. 3B and 3C show the BS39 and BS45 vectors used in the present examples. The following abbreviations are used:

A. Nonessential DNA sequence later deleted.

B. Lac promoter and ribosome binding site.

C. Pectate lyase signal sequence.

D. Kappa chain variable region.

E. Kappa chain constant region.

F. DNA sequence separating kappa and heavy chain, includes ribosome binding site for heavy chain.

G. Alkaline phosphatase signal sequence.

H. Heavy chain variable region.

I. Heavy chain constant region including 5 amino acids of the hinge region.

J. Decapeptide DNA sequence.

K. Pseudo gene VIII sequence with amber stop codon at 5' end.

L. Nonessential DNA sequence that was later deleted.

M. Deleted kappa chain variable sequence with translational step sequences.

N. Polyhistidine (6 codon sequence).

O. Same as F above, but lacking the HindIII site.

P. Deleted heavy chain variable sequence with translational stop sequence.

Q. Pseudo gene VIII sequence without amber stop codon at 5' end.

R. Deleted kappa chain variable sequence with transcriptional stop sequence.

Figure 4:
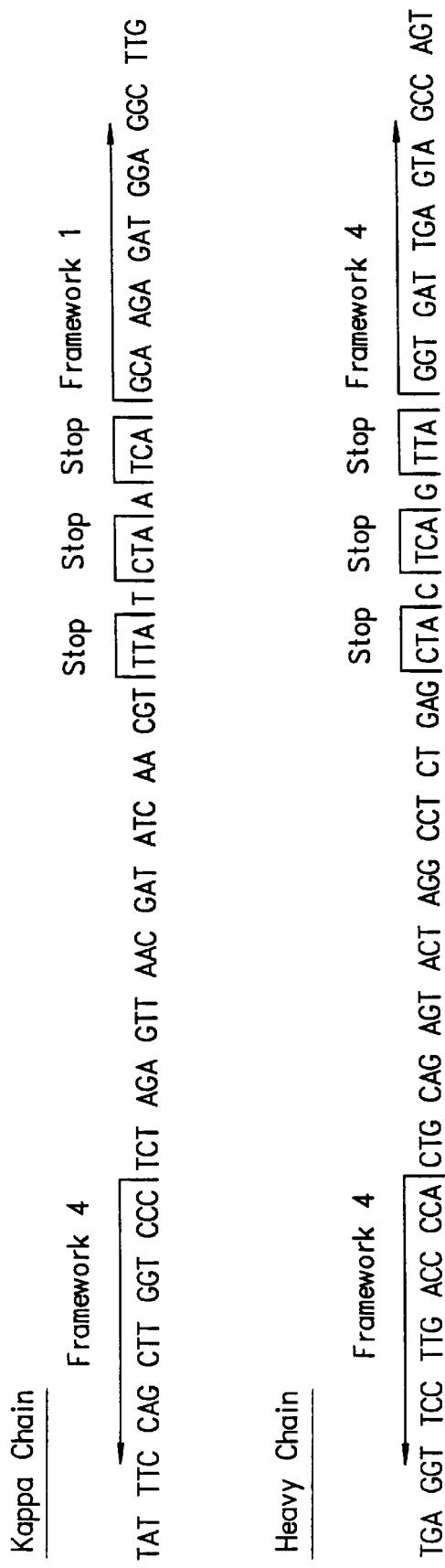

FIG. 4: Oligonucleotides used in vector construction (SEQ ID NOS: 65 and 66).

Figure 5A:
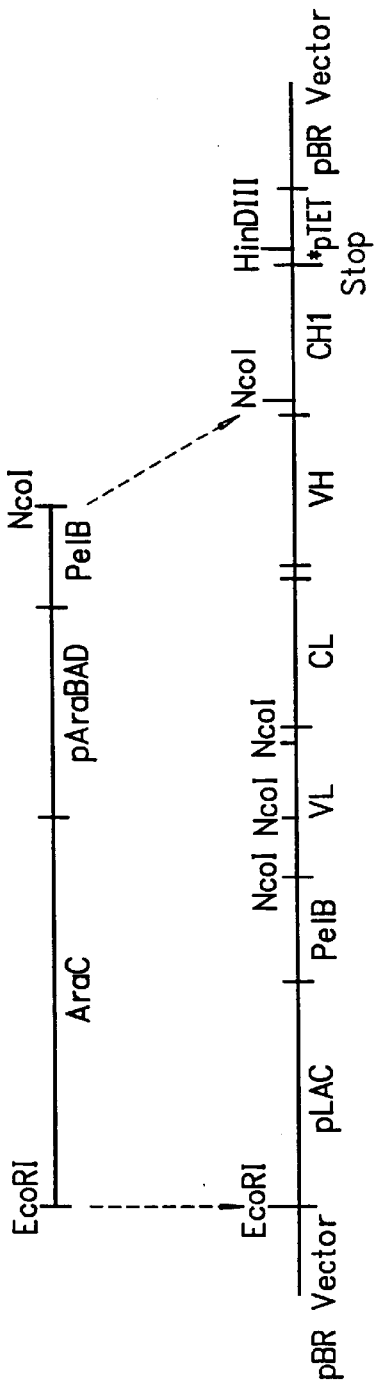
Figure 5B:
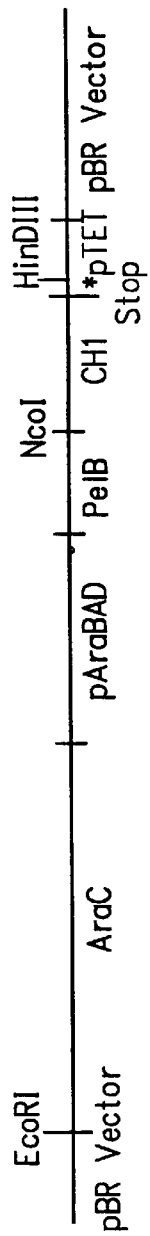

FIG. 5: Insertion of araC into pBR-based vector (FIG. 5A) and the resulting vector pBRnco (FIG. 5B).

Figure 6:
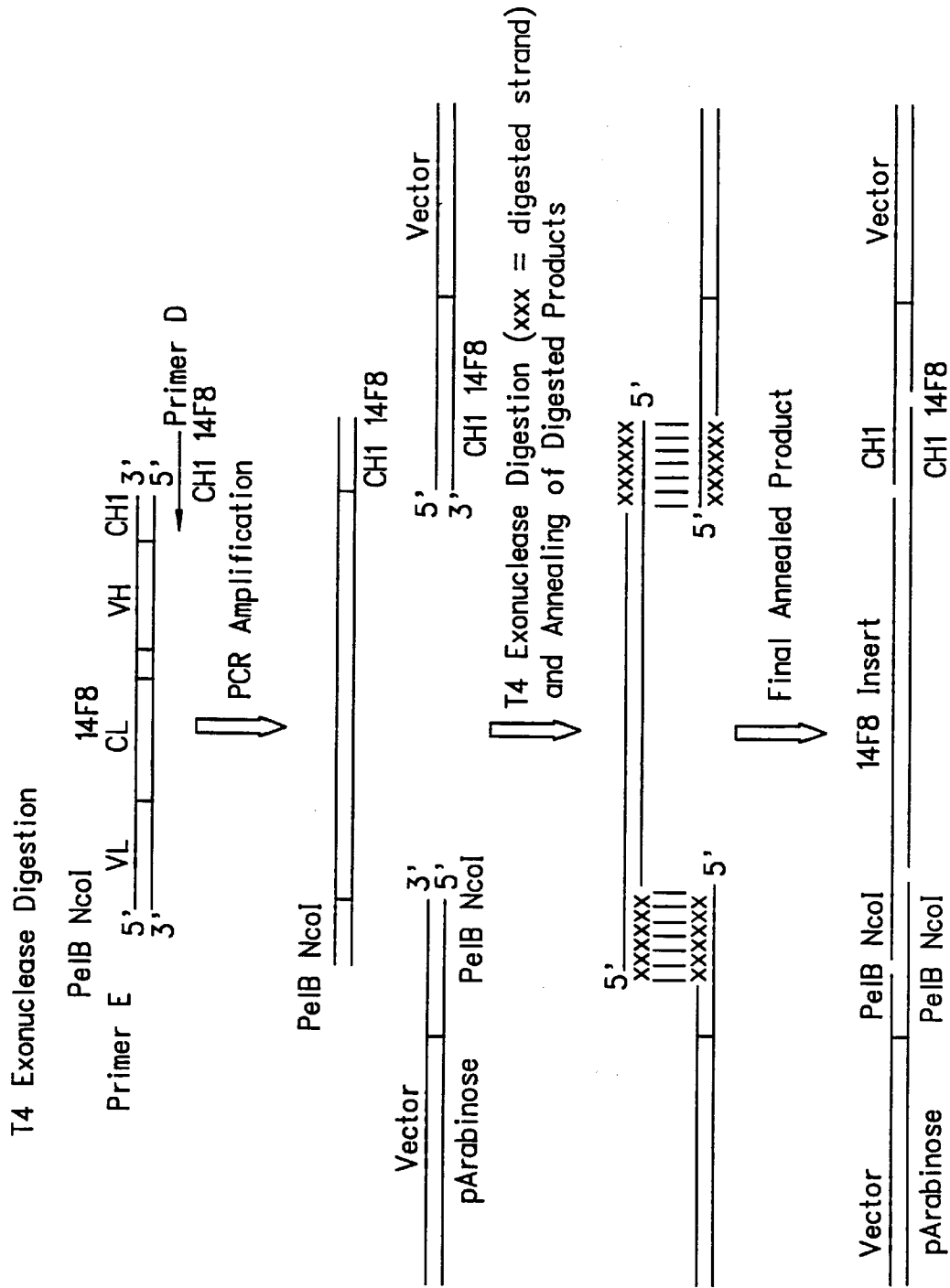

FIG. 6: Subcloning of a DNA segment encoding a Fab by T4 exonuclease digestion.

Figure 7:
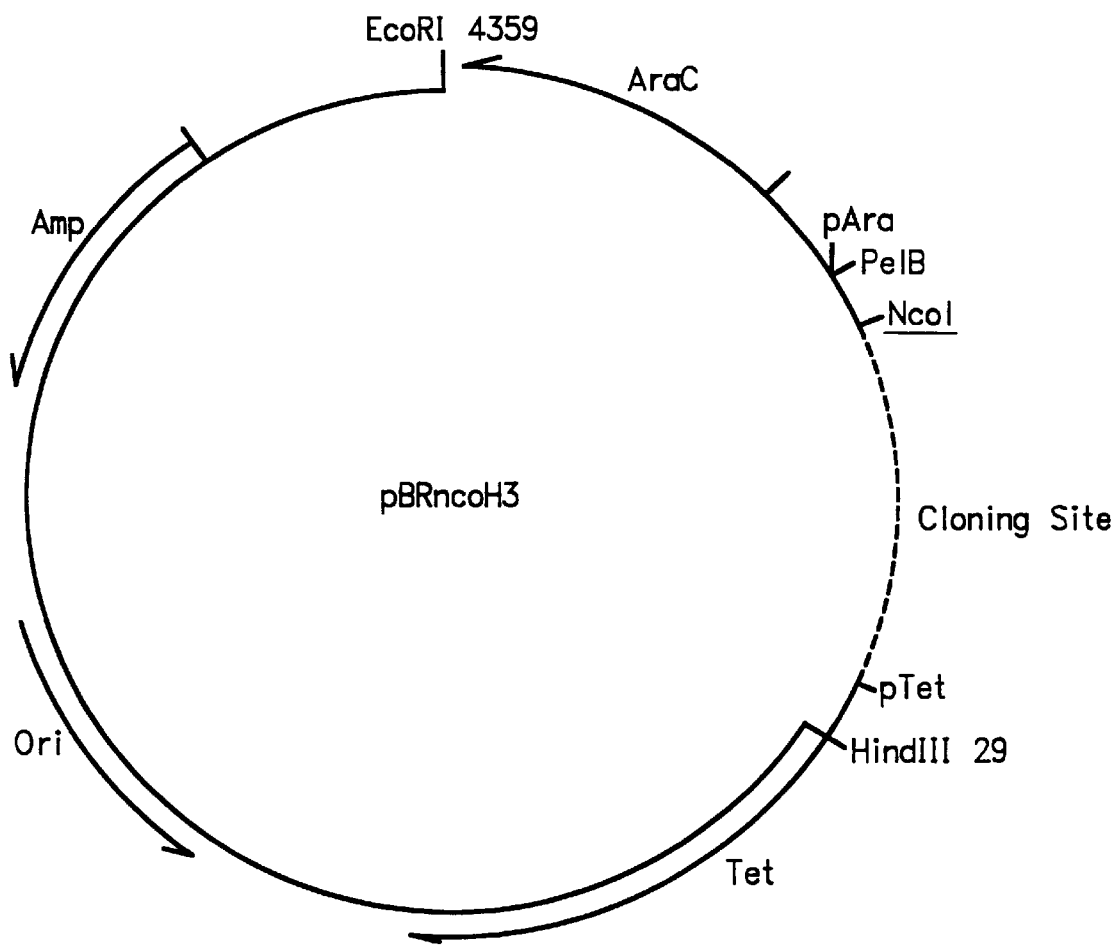

FIG. 7: Map of the vector pBRncoH3.

DEFINITIONS

Specific binding between an antibody or other binding agent and an antigen means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The basic antibody structural unit is known to comprise a tetramer. Each tetramer is composed of two identical pairs of polypeptide chains, each pair having one "light" (about 25 kDa) and one "heavy" chain (about 50–70 Kda). The amino-terminal portion of each chain includes a variable region of about 100 to 110 or more amino acids primarily responsible for antigen recognition. The carboxyl-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989, 4th edition (1999), Paul William E., ed. Raven Press, N.Y.,(incorporated by reference in its entirety for all purposes). The term constant region is used to refer to both full-length natural constant regions and segments thereof, such as $C_H1$, hinge, $C_H^2$ and $C_H3$ or fragments thereof. Typically, segments of light and heavy chain constant regions in antibodies have sufficient length to contribute to interchain bonding between heavy and light chain.

The variable regions of each light/heavy chain pair form the antibody binding site. Thus, an intact antibody has two binding sites. Except in bifunctional or bispecific antibodies, the two binding sites are the same. The chains all exhibit the same general structure of four relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat, et al., supra. An alternative structural definition has been proposed by Chothia, et al., *J. Mol. Biol.* 196:901–917 (1987); *Nature* 342:878–883 (1989); and *J. Mol. Biol.* 186:651–663 (1989).

The term antibody is used to mean whole antibodies and binding fragments thereof. Binding fragments include single chain fragments, Fv fragments and Fab fragments The term Fab fragment is sometimes used in the art to mean the binding fragment resulting from papain cleavage of an intact antibody. The terms Fab' and F(ab')2 are sometimes used in the art to refer to binding fragments of intact antibodies generated by pepsin cleavage. Here, Fab is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the $C_H1$ domain of the constant region.

Chimeric antibodies are antibodies whose light and heavy chain genes have been constructed, typically by genetic engineering, from immunoglobulin gene segments belonging to different species. For example, the variable (V) segments of the genes from a mouse monoclonal antibody can be joined to human constant (C) segments, such as IgG1 and IgG4. A typical chimeric antibody is thus a hybrid protein consisting of the V or antigen-binding domain from a mouse antibody and a C or effector domain from a human antibody. Chimeric antibodies have the same or similar binding specificity and affinity as a mouse or other nonhuman antibody that provides the variable regions of the antibody.

An isolated species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods). A target is any molecule for which it is desired to isolate partners with specific binding affinity for the target.

Targets of interest include antibodies, including anti-idiotypic antibodies and autoantibodies present in autoimmune diseases, such as diabetes, multiple sclerosis and rheumatoid arthritis. Other targets of interest are growth factor receptors (e.g., FGFR, PDGFR, EFG, NGFR, and VEGF) and their ligands. Other targets are G-protein receptors and include substance K receptor, the angiotensin receptor, the α- and β-adrenergic receptors, the serotonin receptors, and PAF receptor. See, e.g., Gilman, *Ann. Rev. Biochem.* 56:625–649 (1987). Other targets include ion channels (e.g., calcium, sodium, potassium channels), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are adhesion proteins such as integrins, selecting, and immunoglobulin superfamily members (see Springer, *Nature* 346:425–433 (1990). Osborn, *Cell* 62:3 (1990); Hynes, *Cell* 69:11 (1992)). Other targets are cytokines, such as interleukins IL-1 through IL-13, tumor necrosis factors α & β, interferons α, β and γ, tumor growth factor Beta (TGF-β), colony stimulating factor (CSF) and granulocyte monocyte colony stimulating factor (GM-CSF). See Human Cytokines: Handbook for Basic & Clinical Research (Aggrawal et al. eds., Blackwell Scientific, Boston, Mass. 1991). Other targets are hormones, enzymes, and intracellular and intercellular messengers, such as, adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241. Some agents screened by the target merely bind to a target. Other agents agonize or antagonize the target.

Display library members having full-length polypeptide coding sequences have coding sequences the same length as that of the coding sequences originally inserted into a display vector before propagation of the vector.

The term phage is used to refer to both phage containing infective genomes and phage containing defective genomes that can be packaged only with a helper phage. Such phage are sometimes referred to as phagemids.

The term "human antibody" includes antibodies having variable and constant regions (if present) derived from human germline immunoglobulin sequences. Some human antibodies include amino acid residues not encoded by human germline immunoglobulin sequences (e.g., mutations introduced by random or site-specific mutagenesis in vitro or by somatic mutation in vivo).

DETAILED DESCRIPTION

I. General

The present invention is directed to inter alia two related but self-sufficient improvements in conventional display methods. The first improvement provides methods of enriching conventional display libraries for members displaying polypeptides capable of binding to a target. Although practice of the claimed methods is not dependent on an understanding of mechanism, the rationale for these methods is believed to be that affinity selection of library members to immobilized binding partners occurs predominantly or exclusively through formation of multivalent bonds between multiple copies of displayed polypeptides on a library member and immobilized binding partners. Accordingly, only members of a library displaying multiple copies of a polypeptide are capable of surviving affinity selection to immobilized binding partners. For example, conventional libraries of polypeptides fused to pVIII of a filamentous phage typically exhibit a Poisson distribution, in which most members display no copies of a polypeptide, a small proportion display one copy of a polypeptide, a still smaller proportion display two copies, and a still smaller proportion display three or more copies. It is believed that the methods of the present invention enrich for the small proportion of conventional display libraries displaying two or more copies of a polypeptide. It is this rare fraction of conventional libraries that is capable of being affinity selected by immobilized binding partners.

Enrichment can be achieved by the inclusion of a tag as a component of the fusion protein from which polypeptides are displayed. The tag can be any polypeptide with a known receptor showing high binding specificity for the tag. The same tag is included in each member of the library. Enrichment is effected by screening the library for affinity binding to an immobilized receptor for the tag. Only library members having two or more copies of the tag are capable of binding to the immobilized receptor. By implication, library members having two copies of the tag have two copies of the fusion protein containing the tag, and two copies of a polypeptide to be screened. The library members that bind to the receptor thus constitute the small subpopulation of library members displaying two or more polypeptides. The library members not binding to the receptor are the majority of library members which display fewer than two copies of a polypeptide (i.e., zero or one copy). These library members, which would nonspecifically bind to the immobilized target in subsequent steps without contributing any members capable of surviving affinity screening through specific binding of the displayed polypeptide, can thus be substantially eliminated.

The bound library members, which display multiple copies of polypeptide, can then be subject to one or more rounds of affinity screening to any immobilized target of interest. Because most library members that would otherwise contribute to nonspecific binding have been eliminated before affinity screening to the target, each round of affinity screening typically results in a greater enrichment for library members with affinity for the target than would be the case in conventional methods. The greater degree of enrichment per round of screening allows adequate screening to be accomplished in fewer rounds and/or a greater proportion of the repertoire of specifically binding library members to be identified.

So efficient are the selection methods of the invention that they result in diverse populations in which the vast majority of members retaining full-length coding sequences encode polypeptides having specific affinity for the target. These polypeptides may differ in fine binding specificity within the target and binding affinity for the target.

A second aspect in which the invention represents a substantial departure from conventional methods resides in the subcloning of nucleic acids encoding displayed polypeptides of enriched libraries from a display vector to an expression vector without clonal isolation of individual members. The utility of transferring populations of coding sequences from a display vector to an expression vector without clonal isolation is realizable because the enriched libraries contain a high proportion of members having the desired binding specificity as described above.

Subcloning is achieved by excising or amplifying nucleic acids encoding polypeptides from the enriched library. The nucleic acids are then preferably size-fractionated on a gel and only full-length sequences are retained. The full-length sequences are inserted into an expression vector in operable linkage to appropriate regulatory sequences to ensure their expression. The modified expression vector is then introduced into appropriate host cells and expressed. Expression results in a population of polypeptides having specific affinity for the desired target. The population of polypeptides can be purified from the host cells by conventional methods. The population of polypeptides typically has substantially the same members in substantially the same proportions as were encoded by the enriched display library. As in the display library, the polypeptides typically differ in fine binding specificity, and binding affinity for the chosen target.

The populations of polypeptides can be used as diagnostic and therapeutic reagents. For example, if the target is a viral antigen, the polypeptides can be used to assay the presence of the virus in tissue samples. If the target is a tumor antigen, the polypeptides can be used as a therapeutic reagent to deliver a toxic substance to cells bearing the tumor antigen. The use of a polyclonal preparation has advantages over a monoclonal reagent in both of these types of applications. For example, the diverse fine binding specificity of members of a population often allows the population to bind to several variant forms of target (e.g., species variants, escape mutant forms) to which a monoclonal reagent may be unable to bind.

II. Display Libraries

A. Display Packages

A display package, sometimes referred to as a replicable genetic package, is a screenable unit comprising a polypeptide to be screened linked to a nucleic acid encoding the polypeptide. The nucleic acid should be replicable either in vivo (e.g., as a vector), optionally in conjunction with host proteins or a helper virus, or in vitro (e.g., by PCR). Cells, spores or viruses are examples of display packages. These display packages can be eukaryotic or prokaryotic. A display library is formed by. introducing nucleic acids encoding exogenous polypeptides to be displayed into the genome of the display package to form a fusion protein with an endogenous protein that is normally expressed from the outer surface of the replicable genetic package. Expression of the fusion protein, transport to the outer surface and assembly results in display of exogenous polypeptides from the outer surface of the genetic package.

A further type of display package comprises a polypeptide bound to a nucleic acid encoding the polypeptide. Such an arrangement can be achieved in several ways. U.S. Pat. No. 5,733,731 describe a method in which a plasmid is engineered to expression a fusion protein comprising a DNA binding polypeptide and a polypeptide to be screened. After expression the fusion protein binds to the vector encoding it though the DNA binding polypeptide component. Vectors displaying fusion proteins are screened for binding to a target, and vectors recovered for further rounds of screening or characterization. In another method, polypeptides are screened as components of display package comprising a polypeptide being screened, and mRNA encoding the polypeptide, and a ribosome holding together the mRNA and polypeptide(see Hanes & Pluckthun, PNAS 94, 4937–4942 (1997); Hanes et al., PNAS 95, 14130–14135 (1998); Hanes etal., FEBS Let. 450, 105–110 (1999); U.S. Pat. No. 5,922,545). mRNA of selected complexes is amplified by reverse transcription and PCR and in vitro transcription, and subject to further screening linked to a ribosome and protein translated from the mRNA. In another method, RNA is fused to a polypeptide encoded by the RNA for screening (Roberts & Szostak, PNAS 94, 12297–12302 (1997), Nemoto et al., FEBS Letters 414, 405–408 (1997). RNA from complexes surviving screening is amplified by reverse transcription PCR and in vitro transcription.

The genetic packages most frequently used for display libraries are bacteriophage, particularly filamentous phage, and especially phage M113, Fd and F1. Most work has inserted libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). Such a fusion protein comprises a signal sequence, usually from a secreted protein other than the phage coat protein, a polypeptide to be displayed and either the gene III or gene VIII protein or a fragment thereof. Exogenous coding sequences are often inserted at or near the N-terminus of gene III or gene VIII although other insertion sites are possible. Some filamentous phage vectors have been engineered to produce a second copy of either gene III or gene VIII. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation, exogenous polypeptide sequences are cloned into phagemid vectors which encode a phage coat protein and phage packaging sequences but which are not capable of replication. Phagemids are transfected into cells and packaged by infection with helper phage. Use of phagemid system also has the effect of diluting fusion proteins formed from coat protein and displayed polypeptide with wild type copies of coat protein expressed from the helper phage. See, e.g., Garrard, WO 92/09690.

Eukaryotic viruses can be used to display polypeptides in an analogous manner. For example, display of human heregulin fused to gp70 of Moloney murine leukemia virus has been reported by Han, et al., *Proc. Natl. Acad. Sci. USA* 92:9747–9751 (1995). Spores can also be used as replicable genetic packages. In this case, polypeptides are displayed from the outer surface of the spore. For example, spores from *B. subtilis* have been reported to be suitable. Sequences of coat proteins of these spores are provided by Donovan, et al., *J. Mol. Biol.* 196:1–10 (1987). Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outer surface proteins are discussed by Ladner, et al., U.S. Pat. No. 5,571,698, and Georgiou, et al., *Nature Biotechnology* 15:29–34 (1997) and references cited therein. For example, the lamB protein of *E. coli* is suitable.

B. Displayed Polypeptides

Polypeptides typically displayed from replicable genetic packages fall into a number of broad categories. One category is libraries of short random or semi random peptides. See, e.g., Cwirla et al., supra. The strategy here is to produce libraries of short peptides in which some or all of the positions are systematically varied for the different amino acids. Random peptide coding sequences can be formed by the cloning and expression of randomly-generated mixtures of oligonucleotides is possible in the appropriate recombinant vectors. See, e.g., Oliphant, et al., *Gene* 44:177–183 (1986)

A second category of library comprises variants of a starting framework protein. See Ladner, et al., supra. In this approach, a starting polypeptide which may be of substantial length is chosen and only selected positions are varied. The nucleic acid encoding the starting polypeptide can be mutagenized by, for example, insertion of mutagenic cassette(s) or error-prone PCR.

A third category of library consists of antibody libraries. Antibody libraries can be single or double chain. Single chain antibody libraries can comprise the heavy or light chain of an antibody alone or the variable domain thereof. However, more typically, the members of single-chain antibody libraries are formed from a fusion of heavy and light chain variable domains separated by a peptide spacer within a single contiguous protein. See e.g., Ladner, et al., WO 88/06630; McCafferty, et al., WO 92/01047. Double-chain antibodies arc formed by noncovalent association of heavy and light chains or binding fragments thereof. Double chain antibodies can also form by association of two single chain antibodies, each single chain antibody comprising a heavy chain variable domain, a linker and a light chain variable domain. In such antibodies, known as diabodies, the heavy chain of one single-chain antibody binds to the light chain of the other and vice versa, thus forming two identical antigen binding sites (see Hollinger et al., *Proc. Natl. Acad. Sci. USA* 90, 6444–6448 (1993) and Carter & Merchan, *Curr. Op. Biotech.* 8, 449–454 (1997). Thus, phage displaying single chain antibodies can form diabodies by association of two single chain antibodies as a diabody.

The diversity of antibody libraries can arise from obtaining antibody-encoding sequences from a natural source, such as a nonclonal population of immunized or unimmunized B cells. Alternatively, or additionally, diversity can be introduced by artificial mutagenesis as discussed for other proteins.

Nucleic acids encoding polypeptides to be displayed optionally flanked by spacers are inserted into the genome of a replicable genetic package as discussed above by standard recombinant DNA techniques (see generally, Sambrook, et al., Molecular Cloning, A Laboratory Manual, 2d ed., Cold Spring Harbor Laboratory Press, Cold Spring Harbor, N.Y., 1989, incorporated by reference herein). The nucleic acids are ultimately expressed as polypeptides (with or without spacer or framework residues) fused to all or part of the an outer surface protein of the replicable package. Libraries often have sizes of about $10^3$, $10^4$, $10^6$, $10^7$, $10^8$ or more members.

C. Double-Chain Antibody Display Libraries

Double-chain antibody display libraries represent a species of the replicable genetic display libraries discussed above. Production of such libraries is described by, e.g., Dower, U.S. Pat. No. 5,427,908; Huse WO 92/06204; Huse, in Antibody Engineering, (Freeman 1992), Ch. 5; Kang, WO 92/18619; Winter, WO 92/20791; McCafferty, WO 92/01047; Hoogenboom WO 93/06213; Winter, et al., *Annu. Rev. Immunol.* 12:433–455 (1994); Hoogenboom, et al., *Immunological Reviews* 130:41–68 (1992); Soderlind, et al., *Immunological Reviews* 130:109–124 (1992). In double-chain antibody libraries, one antibody chain is fused to a phage coat protein, as is the case in single chain libraries. The partner antibody chain is complexed with the first antibody chain, but the partner is not directly linked to a phage coat protein. Either the heavy or light chain can be the chain fused to the coat protein. Whichever chain is not fused to the coat protein is the partner chain. This arrangement is typically achieved by incorporating nucleic acid segments encoding one antibody chain gene into either gIII or gVIII of a phage display vector to form a fusion protein comprising a signal sequence, an antibody chain, and a phage coat protein. Nucleic acid segments encoding the partner antibody chain can be inserted into the same vector as those encoding the first antibody chain. Optionally, heavy and light chains can be inserted into the same display vector linked to the same promoter and transcribed as a polycistronic message. Alternatively, nucleic acids encoding the partner antibody chain can be inserted into a separate vector (which may or may not be a phage vector). In this case, the two vectors are expressed in the same cell (see WO 92/20791). The sequences encoding the partner chain are inserted such that the partner chain is linked to a signal sequence, but is not fused to a phage coat protein. Both antibody chains are expressed and exported to the periplasm of the cell where they assemble and are incorporated into phage particles.

Antibody encoding sequences can be obtained from lymphatic cells of a human or nonhuman animal. Often the cells have been immunized, in which case immunization can be performed in vivo before harvesting cells, or in vitro after harvesting cells, or both. Spleen cells of an immunized animal are a preferred source material. Immunization of humans is only possible with certain antigens. The number of different H chain genes and L chain genes in a spleen from an immunized animal is about $10^6$, which can be assembled in $10^{12}$ potential combinations.

Rearranged immunoglobulin genes can be cloned from genomic DNA or mRNA. For the latter, mRNA is extracted from the cells and cDNA is prepared using reverse transcriptase and poly dT oligonucleotide primers. Primers for cloning antibody encoding sequences are discussed by Larrick, et al., *Bio/Technology* 7:934 (1989), Danielsson & Borrebaceick, in Antibody Engineering: A Practical Guide (Freeman, N.Y., 1992), p.89 and Huse, id. at Ch. 5.

Repertoires of antibody fragments have been constructed by combining amplified $V_H$ and $V_L$ sequences together in several ways. Light and heavy chains can be inserted into different vectors and the vectors combined in vitro (Hogrefe, et al., *Gene* 128:119–126 (1993)) or in vivo (Waterhouse, et al., *Nucl. Acids. Res.* :2265–66 (1993)). Alternatively, the light and heavy chains can be cloned sequentially into the same vector (Barbas, et al., *Proc. Natl. Acad. Sci. USA* 88: 7987–82 (1991)) or assembled together by PCR and then inserted into a vector (Clackson, et al., *Nature* 352:624–28 (1991)). Repertoires of heavy chains can be also be combined with a single light chain or vice versa. Hoogenboom, et al., *J. Mol. Biol.* 227: 381–88 (1992).

Typically, segments encoding heavy and light antibody chains are subcloned from separate populations of heavy and light chains resulting in random association of a pair of heavy and light chains from the populations in each vector. Thus, modified vectors typically contain combinations of heavy and light chain variable region not found in the same lymphatic cell in nature. Some of these combinations typically survive the selection process and also exist in the polyclonal libraries described below.

Some exemplary vectors and procedures for cloning populations of heavy chain and light chain encoding sequences have been described by Huse, WO 92/06204. Diverse populations of sequences encoding $H_c$ polypeptides are cloned into M13IX30 and sequences encoding $L_c$ polypeptides are cloned into M13IX11. The populations are inserted between the XhoI-SeeI or StuI restriction enzyme sites in M13IX30 and between the SacI-XbaI or EcoRV sites in M13IX11 (FIGS. 1A and B of Huse, respectively). Both vectors contain two pairs of MluI-HindIII restriction enzyme sites (FIGS. 1A and B of Huse) for joining together the $H_c$ and $L_c$ encoding sequences and their associated vector sequences. The two pairs are symmetrically orientated about the cloning site so that only the vector proteins containing the sequences to be expressed are exactly combined into a single vector.

Others exemplary vectors and procedures for cloning antibody chains into filamentous phage are described in the present Examples.

III. Enrichment for Polyvalent Display Members

A. Theory of the method

That members of a library displaying multiple copies of a polypeptide are comparatively rare in display libraries is a finding apparently at variance with some early reports in the field. See, e.g., Cwirla et al., supra. Most work on display libraries has been done by inserting nucleic acid libraries into pIII or pVIII of filamentous phage. Because pIII is present in 4 or 5 copies per phage and pVIII is present in several hundred copies per phage, some early reports assumed that foreign polypeptides would be displayed in corresponding numbers per phage. However, more recent work has made clear that the actual number of copies of polypeptide displayed per phage is well below theoretical expectations, perhaps due to proteolytic cleavage of polypeptides. Winter, et al., *Ann. Rev. Immunol.* 12:433–55 (1994). Further, vector systems used for phage display often encode two copies of a phage coat protein, one of which is a wild type protein and the other of which forms a fusion protein with exogenous polypeptides to be displayed. Both copies are expressed and the wild type coat protein effectively dilutes the representation of the fusion protein in the phage coat.

A typical ratio of displayed Fabs per phage, when Fabs are expressed from pVIII of a filamentous phage is about 0.2. The probability, Pr(y), of y Fabs being expressed on a phage particle if the average frequency of expression per phage is n is given by the Poisson probability distribution $$Pr(y)=e^{-n}n^y/y!$$

For a frequency of 0.2 Fabs per phage, the probabilities for the expression of 0, 1, 2, and 3 Fabs per phage are 0.82, 0.16, 0.016, and 0.001 1. The proportion of phage particle displaying two or more Fabs is therefore only 0.017.

The low representation of members displaying more than one Fab fragment in a phage display library can be related to the present inventors' result that only a small percentage of such library members are capable of surviving affinity selection to immobilized binding partners. A library was constructed in which all members encoded the same Fab fragment which was known to have a high binding affinity for a particular target. It was found that even under the mildest separation conditions for removal of free from bound phage, it was not possible to bind more than about 0.004 of the total phage. This proportion is the same order of magnitude as the proportion of phage displaying at least two Fab fragments, suggesting that phage must display at least two Fab fragments to bind to immobilized target. Probably shear forces dissociate phage displaying only a single Fab fragment from the solid phase. Therefore, at least two binding events are necessary for a phage-Fab library member to be bound to immobilized target with sufficient avidity to enable separation of the bound from the free phage. It is expected that similar constraints apply in other forms of display library.

The strategy of the present invention is to enrich for library members displaying more than one polypeptide before the library is contacted with a screening target. Library members lacking two or more polypeptides, which are incapable of surviving affinity selection via binding through displayed polypeptides to any immobilized screening target, but which nevertheless can survive affinity selection by formation of multiple nonspecific bonds to such a target or its support, are thus substantially eliminated before screening of the library to the target is performed.

B. Tags and Receptors

The above strategy is effected by the use of paired tags and receptors. A tag can any peptide sequence that is common to different members of the library, heterologous to the replicable genetic package, and fused to a polypeptide displayed from the replicable genetic package. For example, a tag can be a synthetic peptide sequence, a constant region of an antibody. In some methods, single chain antibodies are displayed in which only the light or heavy chain variable region but not both varies between members. In such situations, among others, the variable region that is the same in different members can be used as a tag. Suitable tag-receptor combinations include epitope and antibody; for example, many high affinity hexapeptide ligands are known for the anti-dynorphin mAb 32.39, (see Barrett et al, *Neuropeptides* 6:113–120 (1985) and Cull et al., *Proc. Nat'l. Acad. Sci. USA* 89:1865–1869 (1992)) and a variety of short peptides are known to bind the MAb 3E7 (Schatz, *Biotechnology* 11:1138–43 (1993)). Another combination of tag and antibody is described by Blanar & Rutter, *Science* 256:1014–1018 (1992).

Another example of a tag-receptor pair is the FLAG™ system (Kodak). The FLAG™ molecular tag consists of an eight amino acid FLAG peptide marker that is linked to the target binding moiety. A 24 base pair segment containing a FLAG coding sequence can be inserted adjacent to a nucleotide sequence that codes for the displayed polypeptide. The FLAG peptide includes an enterokinase recognition site that corresponds to the carboxyl-terminal five amino acids. Capture moieties suitable for use with the FLAG peptide marker include antibodies Anti-FLAG M1, M2 and M5, which are commercially available.

Still other combinations of peptides and antibodies can be identified by conventional phage display methods. Further suitable combinations of peptide sequence and receptor include polyhistidine and metal chelate ligands containing $Ni^{2+}$ immobilized on agarose (see Hochuli in Genetic Engineering: Principles and Methods (ed. JK Setlow, Plenum Press, NY), Ch. 18, pp. 87–96 and maltose binding protein (Maina, et al., *Gene* 74:365–373 (1988)).

Receptors are often labeled with biotin allowing the receptors to be immobilized to an avidin-coated support. Biotin labeling can be performed using the biotinylating enzyme, BirA (see, e.g., Schatz, *Biotechnology* 11:1138–43 (1993)).

A nucleic acid sequence encoding a tag is inserted into a display vector in such a manner that the tag is expressed as part of the fusion protein containing the polypeptide to be displayed and an outer surface protein of the replicable genetic package. The relative ordering of these components is not critical provided that the tag and polypeptide to be displayed are both exposed on the outer surface of the package. For example, the tag can be placed between the outer surface protein and the displayed polypeptide or at or near the exposed end of the fusion protein.

In replicable genetic packages displaying Fabs, a tag can be fused to either the heavy or the light Fab chain, irrespective which chain is linked to a phage coat protein. Optionally, two different tags can used one fused to each of the heavy and light chains. One tag is usually positioned between the phage coat protein and antibody chain linked thereto, and the other tag is positioned at either the N- or C-terminus of the partner chain.

C. Selection of Polyvalent Members

Selection of polyvalent library members is performed by contacting the library with the receptor for the tag component of library members. Usually, the library is contacted with the receptor immobilized to a solid phase and binding of library members through their tag to the receptor is allowed to reach equilibrium. The complexed receptor and library members are then brought out of solution by addition of a solid phase to which the receptor bears affinity (e.g., an avidin-labeled solid phase can be used to immobilize biotin-labeled receptors). Alternatively, the library can be contacted with receptor in solution and the receptor subsequently immobilized. The concentration of receptor should usually be at or above the Kd of the tag/receptor during solution phase binding so that most displayed tags bind to a receptor at equilibrium. When the receptor-library members are contacted with the solid phase only the library members linked to receptor through at least two displayed tags remain bound to the solid phase following separation of the solid phase from library members in solution. Library members linked to receptor through a single tag are presumably sheared from the solid phase during separation and washing of the solid phase. After removal of unbound library members, bound library members can be dissociated from the receptor and solid phase by a change in ionic strength or pH, or addition of a substance that competes with the tag for binding to the receptor. For example, binding of metal chelate ligands immobilized on agarose and containing $Ni^{2+}$ to a hexahistidine sequence is easily reversed by adding imidazole to the solution to compete for binding of the metal chelate ligand. Antibody-peptide binding can often be dissociated by raising the pH to 10.5 or higher.

The average number of polypeptides per library member selected by this method is affected by a number of factors. Decreasing the concentration of receptor during solution-phase binding has the effect of increasing the average number of polypeptides in selected library members. An increase in the stringency of the washing conditions also increases the average number of polypeptides per selected library member. The physical relationship between library members and the solid phase can also be manipulated to increase the average number of polypeptides per library member. For example, if discrete particles are used as the solid phase, decreasing the size of the particles increases the steric constraints of binding and should require a higher density of polypeptides displayed per library member.

For Fab libraries having two tags, one linked to each antibody chain, two similar rounds of selection can be performed, with the products of one round becoming the starting materials for the second round. The first round of selection is performed with a receptor to the first tag, and the second round with a receptor to the second tag. Selecting for both tags enriches for library members displaying two copies of both heavy and light antibody chains (i.e., two Fab fragments).

Although the theory underlying the above methods of polyvalent enrichment is believed to be correct, the practice of the invention is in no way dependent on the correctness of this theory. The data presented in the Examples show that prescreening a display library for members binding to a tag, followed by screening those members for binding to a target results in a higher degree of enrichment for members with affinity for a target than if the method is performed without the prescreening step. Thus, the method can be practiced as described, and achieve the desired result of highly enriched libraries without any understanding of the underlying mechanism.

D. Selection For Affinity to Target

Library members enriched for polyvalent display of Fabs or other polypeptides are screened for binding to a target. The target can be any molecule of interest for which it is desired to identify binding partners. The target should lack specific binding affinity for the tag(s), because in this step it is the displayed polypeptides being screened, and not the tags that bind to the target. The screening procedure at this step is closely analogous to that in the previous step except that the affinity reagent is a target of interest rather than a receptor to a tag. The enriched library members are contacted with the target which is usually labeled (e.g., with biotin) in such a manner that allows its immobilization. Binding is allowed to proceed to equilibrium and then target is brought out of solution by contacting with the solid phase in a process known as panning (Parmley & Smith, *Gene* 73:305–318 (1988)). Library members that remain bound to the solid phase throughout the selection process do so by virtue of polyvalent bonds between them and immobilized target molecules. Unbound library members are washed away from the solid phase.

Usually, library members are subject to amplification before performing a subsequent round of screening. Often, bound library members can be amplified without dissociating them from the support. For example, gene VIII phage library members immobilized to beads, can be amplified by immersing the beads in a culture of *E. coli*. Likewise, bacterial display libraries can be amplified by adding growth media to bound library members. Alternatively, bound library members can be dissociated from the solid phase (e.g., by change of ionic strength or pH) before performing subsequent selection, amplification or propagation.

After affinity selection, bound library members are now enriched for two features: multivalent display of polypeptides and display of polypeptides having specific affinity for the target of interest. However, after subsequent amplification, to produce a secondary library, the secondary library remains enriched for display of polypeptides having specific affinity for the target, but, as a result of amplification, is no longer enriched for polyvalent display of polypeptides. Thus, a second cycle of polyvalent enrichment can then be performed, followed by a second cycle of affinity enrichment to the screening target. Further cycles of affinity enrichment to the screening target, optionally, alternating with amplification and enrichment for polyvalent display can then be performed, until a desired degree of enrichment has been achieved.

In a variation, affinity screening to a target is performed in competition with a compound that resembles but is not identical to the target. Such screening preferentially selects for library members that bind to a target epitope not present on the compound. In a further variation, bound library members can be dissociated from the solid phase in competition with a compound having known crossreactivity with a target for an antigen. Library members having the same or similar binding specificity as the known compound relative to the target are preferentially eluted. Library members with affinity for the target through an epitope distinct from that recognized by the compound remain bound to the solid phase.

Discrimination in selecting between polypeptides of different monovalent affinities for the target is affected by the valency of library members and the concentration of target during the solution phase binding. Assuming a minimum of i labeled target molecules must be bound to a library member to immobilize it on a solid phase, then the probability of immobilization can be calculated for a library member displaying n polypeptides. From the law of mass action, the bound/total polypeptide fraction, F, is $K[targ]/(1+K[targ])$, where $[targ]$ is the total target concentration in solution. Thus, the probability that i or more displayed polypeptides per library member are bound by the labeled target ligand is given by the binomial probability distribution:

$$\sum_n n!/[y!(n-y)!]F^y(1-F)^{n-y}$$
$$y=i$$

As the probability is a function of K and [target], multivalent display members each having a monovalent affinity, K, for the target can be selected by varying the concentration of target. The probabilities of solid-phase immobilization for i=1, 2, or 3, with library members exhibiting monovalent affinities of 0.1/[Ag], 1/[Ag], and 10/[Ag], and displaying n polypeptides per member are:

| n | K = 0.1/[targ] | K = 1/[targ] | K = 10/[targ] |
|---|---|---|---|
| Probability of Immobilization (i = 1) | | | |
| 1 | 0.09 | 0.5 | 0.91 |
| 2 | 0.17 | 0.75 | 0.99 |
| 3 | 0.25 | 0.875 | |
| 4 | 0.32 | 0.94 | |
| 5 | 0.38 | 0.97 | |
| 6 | 0.44 | 0.98 | |
| 7 | 0.49 | 0.99 | |
| 8 | 0.53 | | |
| 9 | 0.58 | | |
| 10 | 0.61 | | |
| 20 | 0.85 | | |
| 50 | 0.99 | | |
| Probability of Immobilization (i = 2) | | | |
| 2 | 0.008 | 0.25 | 0.83 |
| 3 | 0.023 | 0.50 | 0.977 |
| 4 | 0.043 | 0.69 | 0.997 |
| 5 | 0.069 | 0.81 | |
| 6 | 0.097 | 0.89 | |
| 7 | 0.128 | 0.94 | |
| 8 | 0.160 | 0.965 | |
| 9 | 0.194 | 0.98 | |
| 20 | 0.55 | | |
| 50 | 0.95 | | |
| Probability of Immobilization (i = 3) | | | |
| 3 | 0.00075 | 0.125 | 0.75 |
| 4 | 0.0028 | 0.31 | 0.96 |
| 5 | 0.0065 | 0.50 | 0.99 |
| 6 | 0.012 | 0.66 | |
| 7 | 0.02 | 0.77 | |
| 8 | 0.03 | 0.855 | |
| 9 | 0.0415 | 0.91 | |
| 10 | 0.055 | 0.945 | |
| 12 | 0.089 | 0.98 | |
| 14 | 0.128 | 0.99 | |
| 20 | 0.27 | | |
| 50 | 0.84 | | |

The above tables show that the discrimination between immobilizing polypeptides of different monovalent binding affinities is affected by the valency of library members (n) and by the concentration of target for the solution binding phase. Discrimination is maximized when n (number of polypeptides displayed per phage) is equal to i (minimum valency required for solid phase binding). Discrimination is also increased by lowering the concentration of target during the solution phase binding. Usually, the target concentration is around the Kd of the polypeptides sought to be isolated. Target concentration of $10^{-8}$–$10^{-10}$ M are typical.

Enriched libraries produced by the above methods are characterized by a high proportion of members encoding polypeptides having specific affinity for the target. For example, at least 10, 25, 50, 75, 90, 95, or 99% of members encode polypeptides having specific affinity for the target. In libraries of double chain antibodies, a pair of segments encoding heavy and light chains of an antibody is considered a library member. The exact percentage of members having affinity for the target depends whether the library has been amplified following selection, because amplification increases the representation of genetic deletions. However, among members with full-length polypeptide coding sequences, the proportion encoding polypeptides with specific affinity for the target is very high (e.g., at least 50, 75, 90, 95 or 99%). Not all of the library members that encode a polypeptide with specific affinity for the target necessarily display the polypeptide. For example, in a library in which 95% of members with full-length coding sequences encode polypeptides with specific affinity for the target, usually fewer than half actually display the polypeptide. Usually, such libraries have at least 4, 10, 20, 50, 100, 1000, 10,000 or 100,000 different coding sequences. Usually, the representation of any one such coding sequences is no more than 50%, 25% or 10% of the total coding sequences in the library.

IV. Polyclonal Libraries

A. Production

The nucleic acid sequences encoding displayed polypeptides such as are produced by the above methods can be subcloned directly into an expression vector without clonal isolation and testing of individual members. Generally, the sequence encoding the outer surface protein of the display vector fused to displayed polypeptides is not excised or amplified in this process. The nucleic acids can be excised by restriction digestion of flanking sequences or can be amplified by PCR using primers to sites flanking the coding sequences. See generally PCR Technology: Principles and Applications for DNA Amplification (ed. H.A. Erlich, Freeman Press, NY, N.Y., 1992); PCR Protocols: A Guide to Methods and Applications (eds. Innis, et al., Academic Press, San Diego, Calif., 1990); Mattila, et al., *Nucleic Acids Res.* 19:967 (1991); Eckert, et al., *PCR Methods and Applications* 1:17 (1991); PCR (eds. McPherson et al., IRL Press, Oxford). PCR primers can contain a marker sequence that allows positive selection of amplified fragments when introduced into an expression vector. PCR primers can also contain restriction sites to allow cloning into an expression vector, although this is not necessary. For Fab libraries, if heavy and light chains are inserted adjacent or proximate to each other in a display vector, the two chains can be amplified or excised together. For some Fab libraries, only the variable domains of antibody chain(s) are excised or amplified. If the heavy or light chains of a Fab library are excised or amplified separately, they can subsequently be inserted into the same or different expression vectors.

Having excised or amplified fragments encoding displayed polypeptides, the fragments are usually size-purified on an agarose gel or sucrose gradient. Typically, the fragments run as a single sharp full-length band with a smear at lower molecular corresponding to various deleted forms of coding sequence. The band corresponding to full-length coding sequences is removed from the gel or gradient and these sequences are used in subsequent steps.

The next step is to join the nucleic acids encoding full-length coding sequences to an expression vector thereby creating a population of modified forms of the expression vector bearing different inserts. This can be done by conventional ligation of cleaved expression vector with a mixture of inserts cleaved to have compatible ends. Alternatively, the use of restriction enzymes on insert DNA can be avoided. This method of cloning is beneficial because naturally encoded restriction enzyme sites may be present within insert sequences, thus, causing destruction of the sequence when treated with a restriction enzyme. For cloning without restricting, a mixed population of inserts and linearized vector sequences are treated briefly with a 3' to 5' exonuclease such as T4 DNA polymerase or exonuclease III. See Sambrook, et al., Molecular Cloning, A Laboratory Manual (2nd Ed., CSHP, New York 1989). The protruding 5' termini of the insert generated by digestion are complementary to single-stranded overhangs generated by digestion of the vector. The overhangs are annealed, and the re-annealed vector transfected into recipient host cells. The same result can be accomplished using 5' to 3' exonucleases rather than a 3' to 5' exonuclease.

Preferably, ligation of inserts to expression vector is performed under conditions that allow selection against re-annealed vector and uncut vector. A number of vectors containing conditional lethal genes that allow selection against re-annealed vector under nonpermissive conditions are known. See, e.g., Conley & Saunders, *Mol. Gen. Genet.* 194:211–218 (1984). These vectors effectively allow positive selection for vectors having received inserts. Selection can also be accomplished by cleaving an expression vector in such a way that a portion of a positive selection marker (e.g., antibiotic resistance) is deleted. The missing portion is then supplied by full-length inserts. The portion can be introduced at the 3' end of polypeptide coding sequences in the display vector, or can be included in a primer used for amplification of the insert. An exemplary selection scheme, in which inserts supply a portion of a tetracycline-resistance gene promoter deleted by HindIII cleavage of a pBR-derivative vector, is described in Example 17.

The choice of expression vector depends on the intended host cells in which the vector is to be expressed. Typically, the vector includes a promoter and other regulatory sequences in operable linkage to the inserted coding sequences that ensure the expression of the latter. Use of an inducible promoter is advantageous to prevent expression of inserted sequences except under inducing conditions. Inducible promoters include arabinose, lacZ, metallothionein promoter or a heat shock promoter. Cultures of transformed organisms can be expanded under noninducing conditions without biasing the population for coding sequences whose expression products are better tolerated by the host cells. The vector may also provide a secretion signal sequence position to form a fusion protein with polypeptides encoded by inserted sequences, although often inserted polypeptides are linked to a signal sequences before inclusion in the vector. Vectors to be used to receive sequences encoding antibody light and heavy chain variable domains sometimes encode constant regions or parts thereof that can be expressed as fusion proteins with inserted chains thereby leading to production of intact antibodies or fragments thereof.

*E. coli* is one prokaryotic host useful particularly for cloning the polynucleotides of the present invention. Other microbial hosts suitable for use include bacilli, such as *Bacillus subtilis*, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast, are also used for expression. Saccharomyces is a preferred host, with suitable vectors having expression control sequences, such as promoters, including 3-phosphoglycerate kinase or other glycolytic enzymes, and an origin of replication, termination sequences and the like as desired. Insect cells in combination with baculovirus vectors can also be used.

Mammalian tissue cell culture can also be used to express and produce the polypeptides of the present invention (see Winnacker, From Genes to Clones (VCH Publishers, N.Y., N.Y., 1987). A number of suitable host cell lines capable of secreting intact immunoglobulins have been developed including the CHO cell lines, various Cos cell lines, HeLa cells, myeloma cell lines, transformed B-cells and hybridomas. Expression vectors for these cells can include expression control sequences, such as an origin of replication, a promoter, and an enhancer (Queen, et al., *Immunol. Rev.* 89:49–68 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, or cytomegalovirus.

Methods for introducing vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra).

Once expressed, collections of antibodies or other polypeptides are purified from culture media and host cells. Usually, polypeptides are expressed with signal sequences and are thus released to the culture media. However, if polypeptides are not naturally secreted by host cells, the polypeptides can be released by treatment with mild detergent. Polypeptides can then be purified by conventional methods including ammonium sulfate precipitation, affinity chromatography to immobilized target, column chromatography, gel electrophoresis and the like (see generally Scopes, Protein Purification (Springer-Verlag, N.Y., 1982)).

B. Characteristics of Libraries

The above methods result in novel libraries of nucleic acid sequences encoding polypeptides having specific affinity for a chosen target. The libraries of nucleic acids typically have at least 5, 10, 20, 50, 100, 1000, $10^4$ or $10^5$ different members. Usually, no single member constitutes more than 25 or 50% of the total sequences in the library. Typically, at least 25, 50%, 75, 90, 95, 99 or 99.9% of library members encode polypeptides with specific affinity for the target molecules. In the case of double chain antibody libraries, a pair of nucleic acid segments encoding heavy and light chains respectively is considered a library member. The nucleic acid libraries can exist in free form, as components of any vector or transfected as a component of a vector into host cells.

The nucleic acid libraries can be expressed to generate polyclonal libraries of antibodies or other polypeptides having specific affinity for a target. The composition of such libraries is determined from the composition of the nucleotide libraries. Thus, such libraries typically have at least 5, 10, 20, 50, 100, 1000, $10^4$ or $10^5$ members with different amino acid composition. Usually, no single member constitutes more than 25 or 50% of the total polypeptides in the library. The percentage of polypeptides in a polypeptide library having specific affinity for a target is typically lower than the percentage of corresponding nucleic acids encoding the peptides. The difference is due to the fact that not all polypeptides fold into a structure appropriate for binding despite having the appropriate primary amino acid sequence to support appropriate folding. In some libraries, at least 25, 50, 75, 90, 95, 99 or 99.9% of polypeptides have specific affinity for the target molecules. Again, in libraries of multi-chain antibodies, each antibody (such as a Fab or intact antibody) is considered a library member. The different polypeptides differ from each other in terms of fine binding specificity and affinity for the target. Some such libraries comprise members binding to different epitopes on the same antigen. Some such libraries comprises at least two members that bind to the same antigen without competing with each other.

V. Polyclonal Chimeric Antibody Libraries

In a variation of the procedures described above, the invention further provides libraries of polyclonal chimeric antibodies, and libraries of the DNA segments encoding the same. A chimeric antibody comprises at least one chimeric antibody chain, meaning that the antibody has a variable region from a first species, and a constant region from a second species. Such libraries share the property of low immunogenicity of chimeric monoclonals described by Cabilly U.S. Pat. No. 4,816,567, but offer advantages in terms of including antibodies that bind to multiple epitopes within an antigen in a single preparation. Some chimeric antibodies, such as Fab fragments, have a chimeric heavy chain and a chimeric light chain. The chimeric light chain comprises a light chain variable region from a first species, and a constant region from a second species. Likewise the chimeric heavy chain comprises a heavy chain variable region from a first species, and a heavy chain constant region from a second species. An intact chimeric antibody comprises two copies of a chimeric light chain and two copies of a chimeric heavy chain.

The variable regions of such antibodies are typically obtained from a nonhuman species, such as mouse, rat, rabbit, guinea pig, cow, horse, sheep, vulcher, monkey or chimpanzee. The constant regions are typically human for chimerics intended for use in humans or from the animal species of intended use for veterinary applications. In a Fab fragment, the heavy chain constant region usually comprises a $C_H1$ region, and optionally, part or all of a hinge region, and the light chain constant region is an intact light chain constant region, such as $C_K$ or $C_\lambda$. In an intact antibody, the heavy chain constant region typically includes $C_H1$, hinge, $C_H2$, and $C_H3$ regions, and the light chain an intact $C_K$ or $C_\lambda$, light chain. Typically, the constant regions in chimeric antibodies are naturally occurring human constant regions; a few conservative substitutions can be tolerated although are not preferred. Likewise, the variable regions are usually natural variable regions of a nonhuman species, although additional variation can be introduced by induced mutations of such sequences. Choice of constant region isotype depends in part on whether complement-dependent cytotoxicity is required. For example, human isotypes IgG1 and IgG4 support such cytotoxicity whereas IgG2 and IgG3 do not.

The libraries of chimeric antibodies provided by the invention show the same diversity and composition as the polyclonal libraries described above. For example, a library of chimeric antibodies typically have at least 5, 10, 20, 50, 100, 1000, $10^4$ or $10^5$ members with different amino acid composition. Usually, no single member constitutes more than 25 or 50% of the total antibodies in the library. In some libraries, at least 25, 50, 75, 90, 95, 99 or 99.9% of antibodies have specific affinity for the target molecules. Again, in libraries of multi-chain chimeric antibodies, each stable combination of antibody chains (such as a Fab or intact antibody) is considered a library member. Likewise, libraries of nucleic acids typically have at least 5, 10, 20, 50, 100, 1000, $10^4$ or $10^5$ different members. Usually, no single member constitutes more than 25 or 50% of the total sequences in the library. Typically, at least 75, 90, 95, 99 or 99.9% of library members encode antibodies with specific affinity for the target molecules. In the case of double chain antibody libraries, including libraries of diabodies, a pair of nucleic acid segments encoding heavy and light chains respectively is considered a library member.

Some libraries of double chain chimeric antibodies comprises members having randomly associated heavy and light chains resulting from random combination of heavy and light chain antibody populations when subcloning into the replicable genetic package. Some libraries of chimeric antibodies contain members having specificity for distinct epitopes on a common target, such members binding to the same target but not in competition with each other.

Libraries of chimeric antibodies can be produced by any of several variations on the basic cloning and selection strategy described above. In one variation, the phage vector or other replicable genetic package used for screening antibodies is genetically modified to express heavy and light chain constant regions in frame with inserted heavy and light chain variable regions. For example, the vector can be modifed to encode a human $C_H1$ region in frame with an inserted heavy chain variable region and an intact human light chain constant region, such as kappa or lambda, in frame with an inserted light chain variable region. In such an arrangement, replicable genetic packages are capable of expressing and displaying chimeric Fab fragments comprising nonhuman variable regions and human constant regions. Libraries of replicable genetic packages displaying chimeric Fab fragments are enriched for polyvalent members by binding of a tag to a receptor as described above, and then screened for binding to a target. Optionally, additional cycles of polvalent enrichment and screening to a target are performed until a high percentage of library members encode antibodies with affinity for the target. The DNA encoding heavy and light chimeric chains, including both constant and variable regions, can then be excised as a unit from such vectors, and subcloned en masse (i.e., as a mixture of sequences encoding different antibodies) into multiple copies of an expression vector, using the same subcloning procedures described above. The resulting population of expression vectors then encodes and expresses a population of chimeric Fab fragments.

In another variation, a library of replicable genetic packages encoding chimeric Fab fragments is screened as described above. Further, sequences encoding heavy and light chimeric chains are subcloned en masse into an expression vector as above. However, the expression vector is designed to encode an additional segment of the human heavy chain constant region (typically, hinge, $C_H2$ and $C_H3$) regions in-frame with the segment of the chimeric heavy chain present in the Fab fragment. The resulting population of modified vectors expresses a population of intact antibodies. Of course, many minor variations are possible as to precisely which segment of the human heavy chain constant region is supplied by the replicable genetic package and which by the expression vector. For example, the replicable genetic package can be designed to include a $C_H1$ region, and some or all of the hinge region. In this case, the expression vector is designed to supply the residual portion of the hinge region (if any) and the $C_H2$ and $C_H3$ regions for expression of intact antibodies.

In a further variation, antibody chains are initially screened in a replicable genetic package in nonchimeric form, and human constant regions are supplied by subcloning into a second replicable genetic package. As an example, mouse Fab fragments containing both variable regions and constant regions from a mouse, can be displayed from a variable genetic package and screened as described above. A subpopulation of vectors expressing mouse Fabs with affinity for a target is isolated. The heavy and light chain variable regions from these vectors are then separately isolated and recloned into a second vector, which provides light and heavy chain constant regions in-frame with incorporated light and heavy chain mouse variable regions. Typically, the recloning is performed en masse resulting in random association of heavy and light chains in the second vector. Thus, the second vector is typically a replicable genetic package allowing display of antibodies and rescreening. Following rescreening, chimeric heavy and light chain are subcloned as a unit en masse from the replicable genetic package to an expression vector, optionally modified to contain an additional segment of the human heavy chain constant region. The resulting population of modified expression vectors express chimeric Fab fragments or intact antibodies as described above.

In a further variation, antibodies are initially screened as single-chain antibodies comprising a heavy chain variable region, a spacer and a light chain variable region. Heavy and light chains from replicable genetic packages surviving selection are then separately isolated and subcloned into a second vector, which provides human heavy and light chain constant regions as described above. Such subcloning results in random association of heavy and light chains, so typically the second vector is also a replicable genetic package allowing rescreening. Following rescreening, chimeric heavy and light chain are subcloned as a unit en masse from the replicable genetic package to an expression vector, optionally modified to contain an additional segment of the human heavy chain constant region. The resulting population of modified expression vectors again express chimeric Fab fragments or intact antibodies.

In a further variation, a library of nonhuman heavy chains or nonhuman light chains (but not both) is subcloned into a replicable genetic package for screening. The library can be screened as single chain antibodies, or in combination with a partner chain encoded by a second replicon. In such methods, the antibody chain encoded by the replicable genetic package can be linked to either a mouse or human constant region. Typically, the antibody chain is linked to the same type of constant region as the partner chain encoded by the second replicon (if present). Following screening and selection of the library, antibody chains surviving selection are subcloned en masses into an expression vector. If the antibody chains are screened linked to a human constant region, this constant region is typically transferred to the expression vector as a unit with the antibody variable region. Optionally, the expression vector can supply a further segment of a human constant region expressed in frame with that already linked to antibody chains being cloned into the vector. If antibody chains were screened in combination with a partner antibody chain encoded by a second replicon, the expression vector typically encodes the variable region of the partner antibody chain in frame with a human constant region. Accordingly, the expression vector expressing chimeric antibodies comprises chimeric antibody chains originally encoded by the replicable genetic package complexed with chimeric partner chains. Such an expression vector can express either Fab fragments or intact antibodies depending on how much of the human heavy chain constant region is present.

VII. Diagnostic and Therapeutics Uses

The use of polyclonal antibodies in diagnostics and therapeutics has been limited by the inability to generate preparations that have a well-defined affinity and specificity. Monoclonal antibodies developed using hybridoma technology do have well-defined specificity and affinity, but the selection process is often long and tedious. Further, a single monoclonal antibody often does not meet all of the desired specificity requirements. Formation of polyclonal mixtures by isolation, and characterization of individual monoclonal antibodies, which are then mixed would be time consuming process which would increase in proportion to the number of monoclonals included in the mixture and become prohibitive for substantial numbers of monoclonal antibodies. The polyclonal libraries of antibodies and other polypeptides having specificity for a given target produced by the present methods avoid these difficulties, and provide reagents that are useful in many therapeutic and diagnostic applications.

The use of polyclonal mixtures has a number of advantages with respect to compositions made of one monoclonal antibody. By binding to multiple sites on a target, polyclonal antibodies or other polypeptides can generate a stronger signal (for diagnostics) or greater blocking/inhibition/cytotoxicity (for therapeutics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto.

Polyclonal preparations of antibodies and other polypeptides can be incorporated into compositions for diagnostic or treatment use (both prophylactic and therapeutic). The preferred form depends on the intended mode of administration and diagnostic or therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. See Remington's Pharmaceutical Science (15th ed., Mack Publishing Company, Easton, Pa., 1980). Compositions intended for in vivo use are usually sterile. Compositions for parental administration are sterile, substantially isotonic and made under GMP condition.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. Cell lines producing antibodies CD.TXA.1.PC (ATCC 98388, Apr. 3, 1997), CD.43.9 (ATCC 98390, Apr. 3, 1997), CD.43.5.PC (ATCC 98389, Apr. 3, 1997) and 7F11 (HB-12443, Dec. 5, 1997) have been deposited at the American Type Culture Collection, Rockville, Md. under the Budapest Treaty on the dates indicated and given the accession numbers indicated. The deposits will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

EXAMPLES

Example 1

Immunization of Mice with Antigens and Purification of RNA from Mouse Spleens Mice were immunized by the following method based on experience of the timing of spleen harvest for optimal recovery of mRNA coding for antibody. Two species of mice were used: Balb/c (Charles River Laboratories, Wilmington, Mass.) and A/J (Jackson Laboratories, Bar Harbor, Me.). Each of ten mice were immunized intraperitoneally with antigen using 50 μg protein in Freund's complete adjuvant on day 0, and day 28. Tests bleeds of mice were obtained through puncture of the retro-orbital sinus. If, by testing the titers, they were deemed high by ELISA using biotinylated antigen immobilized via streptavidin, the mice were boosted with 50 μg of protein on day 70, 71 and 72, with subsequent sacrifice and splenectomy on day 77. If titers of antibody were not deemed satisfactory, mice were boosted with 50 μg antigen on day 56 and a test bleed taken on day 63. If satisfactory titers were obtained, the animals were boosted with 50 μg of antigen on day 98, 99, and 100 and the spleens harvested on day 105. Typically, a test bleed dilution of 1:3200 or more resulted in a half maximal ELISA response to be considered satisfactory.

The spleens were harvested in a laminar flow hood and transferred to a petri dish, trimming off and discarding fat and connective tissue. The spleen was, working quickly, macerated with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension was pulled through an 18 gauge needle until viscous and all cells were lysed, then transferred to a microcentrifuge tube. The petri dish was washed with 100 μl of solution D to recover any remaining spleen, and this was transferred to the tube. The suspension was then pulled through a 22 gauge needle an additional 5–10 times. The sample was divided evenly between two microcentrifuge tubes and the following added in order, with mixing by inversion after each addition: 100 μl 2 M sodium acetate (pH 4.0), 1.0 ml water-saturated phenol (Fisher Scientific, Pittsburgh, Pa.), 200 μl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol/chloroform/isoamyl alcohol (50:49:1) was added, and the tube was vortexed for ten seconds. After a 15 min incubation on ice, the sample was centrifuged for 20 min at 2–8° C., and the aqueous phase was transferred to a fresh tube and precipitated with an equal volume of isopropanol at –20° C. for a minimum of 30 min. Following centrifugation at 14,000 rpm for 20 min at 4° C., the supernatant was aspirated away, the tubes briefly spun and all traces of liquid removed. The RNA pellets were each dissolved in 300 μl of solution D, combined, and precipitated with an equal volume of isopropanol at –20° C. for a minimum of 30 min. The sample was centrifuged 14,000 rpm for 20 min at 4° C., the supernatant aspirated as before, and the sample rinsed with 100 μl of ice-cold 70% ethanol. The sample was again centrifuged 14,000 rpm for 20 min at 4° C., the 70% ethanol solution aspirated, and the RNA pellet dried in vacuo. The pellet was resuspended in 100 μl of sterile distilled water. The concentration was determined by $A_{260}$ using an absorbance of 1.0 for a concentration of 40 μg/ml. The RNA was stored at –80° C.

Example 2

Preparation of Complementary DNA (cDNA)

The total RNA purified as described above was used directly as template or cDNA. RNA (50 μg) was diluted to 100 μL with sterile water, and 10 μL–130 μg/μL oligo $dT_{12}$ (synthesized on Applied Biosystems Model 392 DNA synthesizer at Biosite Diagnostics) was added. The sample was heated for 10 min at 70° C., then cooled on ice. 40 μL 5×first strand buffer was added (Gibco/BRL, Gaithersburg, Md.), 20 μL 0.1 M dithiothreitol (Gibco/BRL, Gaithersburg, Md.), 10 μL 20 mM deoxynucleoside triphosphates (dNTP's, Boehringer Mannheim, Indianapolis, Ind.), and 10 μL water on ice. The sample was then incubated at 37° C. for 2 min. 10 μL reverse transcriptase (Superscript™ II, Gibco/BRL, Gaithersburg, Md.) was added and incubation was continued at 37° C. for 1 hr. The cDNA products were used directly for polymerase chain reaction (PCR).

Example 3

Amplification of cDNA by PCR

To amplify substantially all of the H and L chain genes using PCR, primers were chosen that corresponded to substantially all published sequences. Because the nucleotide sequences of the amino terminals of H and L contain considerable diversity, 33 oligonucleotides were synthesized to serve as 5' primers for the H chains (FIG. 1), and 29 oligonucleotides were synthesized to serve as 5' primers for the kappa L chains (FIG. 2). The 5' primers were made according to the following criteria. First, the second and fourth amino acids of the L chain and the second amino acid of the heavy chain were conserved. Mismatches that changed the amino acid sequence of the antibody were allowed in any other position. Second, a 20 nucleotide sequence complementary to the M13 uracil template was synthesized on the 5' side of each primer. This sequence is different between the H and L chain primers, corresponding to 20 nucleotides on the 3' side of the pelB signal sequence for L chain primers and the alkaline phosphatase signal sequence for H chain primers. The constant region nucleotide sequences required only one 3' primer each to the H chains and the kappa L chains (FIG. 2). Amplification by PCR was performed separately for each pair of 5' and 3' primers. A 50 μL reaction was performed for each primer pair with 50 pmol of 5' primer, 50 pmol of 3' primer, 0.25 μL Taq DNA Polymerase (5 units/μL, Boehringer Mannheim, Indianapolis, Ind.), 3 μL cDNA (described in Example 2), 5 μL 2 mM dNTP's, 5 μL 10×Taq DNA polymerase buffer with MgC12 (Boehringer Mannheim, Indianapolis, Ind.), and $H_2O$ to 50 μL. Amplification was done using a GeneAmp™ 9600 thermal cycler (Perkin Elmer, Foster City, Calif.) with the following program: 94° C. for 1 min; 30 cycles of 94° C. for 20 sec, 55° C. for 30 sec, and 72° C. for 30 sec; 72° C. for 6 min; 4° C.

The dsDNA products of the PCR process were then subjected to asymmetric PCR using only 3' primer to generate substantially only the anti-sense strand of the target genes. A 100 µL reaction was done for each dsDNA product with 200 pmol of 3' primer, 2 µL of ds-DNA product, 0.5 µL Taq DNA Polymerase, 10 µL 2 mM dNTP's, 10 µL 10×Taq DNA polymerase buffer with $MgCl_2$ (Boehringer Mannheim, Indianapolis, Ind.), and $H_2O$ to 100 µL. The same PCR program as that described above was used to amplify the single-stranded (ss)-DNA.

Example 4

Purification of ss-DNA by High Performance Liquid Chromatography and Kinasing ss-DNA The H chain ss-PCR products and the L chain ss-PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14,000 rpm for 10 min at 2–8° C. The supernatant was carefully aspirated, and the tubes were briefly spun a 2nd time. The last drop of supernatant was removed with a pipet. The DNA was dried in vacuo for 10 min on medium heat. The H chain products were pooled in 210 µL water and the L chain products were pooled separately in 210 µL water. The ss-DNA was purified by high performance liquid chromatography (HPLC) using a Hewlett Packard 1090 HPLC and a Gen-Pak™ FAX anion exchange column (Millipore Corp., Milford, Mass.). The gradient used to purify the ss-DNA is shown in Table 1, and the oven temperature was at 60° C. Absorbance was monitored at 260 nm. The ss-DNA eluted from the HPLC was collected in 0.5 min fractions. Fractions containing ss-DNA were ethanol precipitated, pelleted and dried as described above. The dried DNA pellets were pooled in 200 µL sterile water.

TABLE 1

HPLC gradient for purification of ss-DNA

| Time (min) | % A | % B | % C | Flow (mL/min) |
| --- | --- | --- | --- | --- |
| 0 | 70 | 30 | 0 | 0.75 |
| 2 | 40 | 60 | 0 | 0.75 |
| 32 | 15 | 85 | 0 | 0.75 |
| 35 | 0 | 100 | 0 | 0.75 |
| 40 | 0 | 100 | 0 | 0.75 |
| 41 | 0 | 0 | 100 | 0.75 |
| 45 | 0 | 0 | 100 | 0.75 |
| 46 | 0 | 100 | 0 | 0.75 |
| 51 | 0 | 100 | 0 | 0.75 |
| 52 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The ss-DNA was kinased on the 5' end in preparation for mutagenesis (Example 7). 24 µL 10×kinase buffer (United States Biochemical, Cleveland, Ohio), 10.4 µL 10 mM adenosine-5'-triphosphate (Boehringer Mannheim, Indianapolis, Ind.), and 2 µL polynucleotide kinase (30 units/µL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio)-chloroform-isoamyl alcohol (50:49:1) and one extraction with chloroform:isoamyl alcohol (49:1). After the extractions, the DNA was ethanol precipitated and pelleted as described above. The DNA pellets were dried, then dissolved in 50 µL sterile water. The concentration was determined by measuring the absorbance of an aliquot of the DNA at 260 nm using 33 µg/mL for an absorbance of 1.0. Samples were stored at −20° C.

Example 5

Antibody Phage Display Vector

The antibody phage display vector for cloning antibodies was derived from an M13 vector supplied by Ixsys, designated 668-4. The vector 668-4 contained the DNA sequences encoding the heavy and light chains of a mouse monoclonal Fab fragment inserted into a vector described by Huse, WO 92/06024. The vector had a Lac promoter, a pelB signal sequence fused to the 5' side of the L chain variable region of the mouse antibody, the entire kappa chain of the mouse antibody, an alkaline phosphatase signal sequence at the 5' end of the H chain variable region of the mouse antibody, the entire variable region and the first constant region of the H chain, and 5 codons of the hinge region of an IgG1 H chain. A decapeptide sequence was at the 3' end of the H chain hinge region and an amber stop codon separated the decapeptide sequence from the pseudo-gene VIII sequence. The amber stop allowed expression of H chain fusion proteins with the gene VIII protein in *E. coli* suppressor strains such as XL1 blue (Stratagene, San Diego, Calif.), but not in nonsuppressor cell strains such as MK30 (Boehringer Mannheim, Indianapolis, Ind.) (see FIG. 3A).

To make the first derivative cloning vector, deletions were made in the variable regions of the H chain and the L chain by oligonucleotide directed mutagenesis of a uracil template (Kunkel, *Proc. Natl. Acad. Sci. USA* 82:488 (1985); Kunkel, et al., *Methods. Enzymol.* 154:367 (1987)). These mutations deleted the region of each chain from the 5' end of CDR1 to the 3' end of CDR3, and the mutations added a DNA sequence where protein translation would stop (see FIG. 4 for mutagenesis oligonucleotides). This prevented the expression of H or L chain constant regions in clones without an insert, thereby allowing plaques to be screened for the presence of insert. The resulting cloning vector was called BS11.

Figure 3:
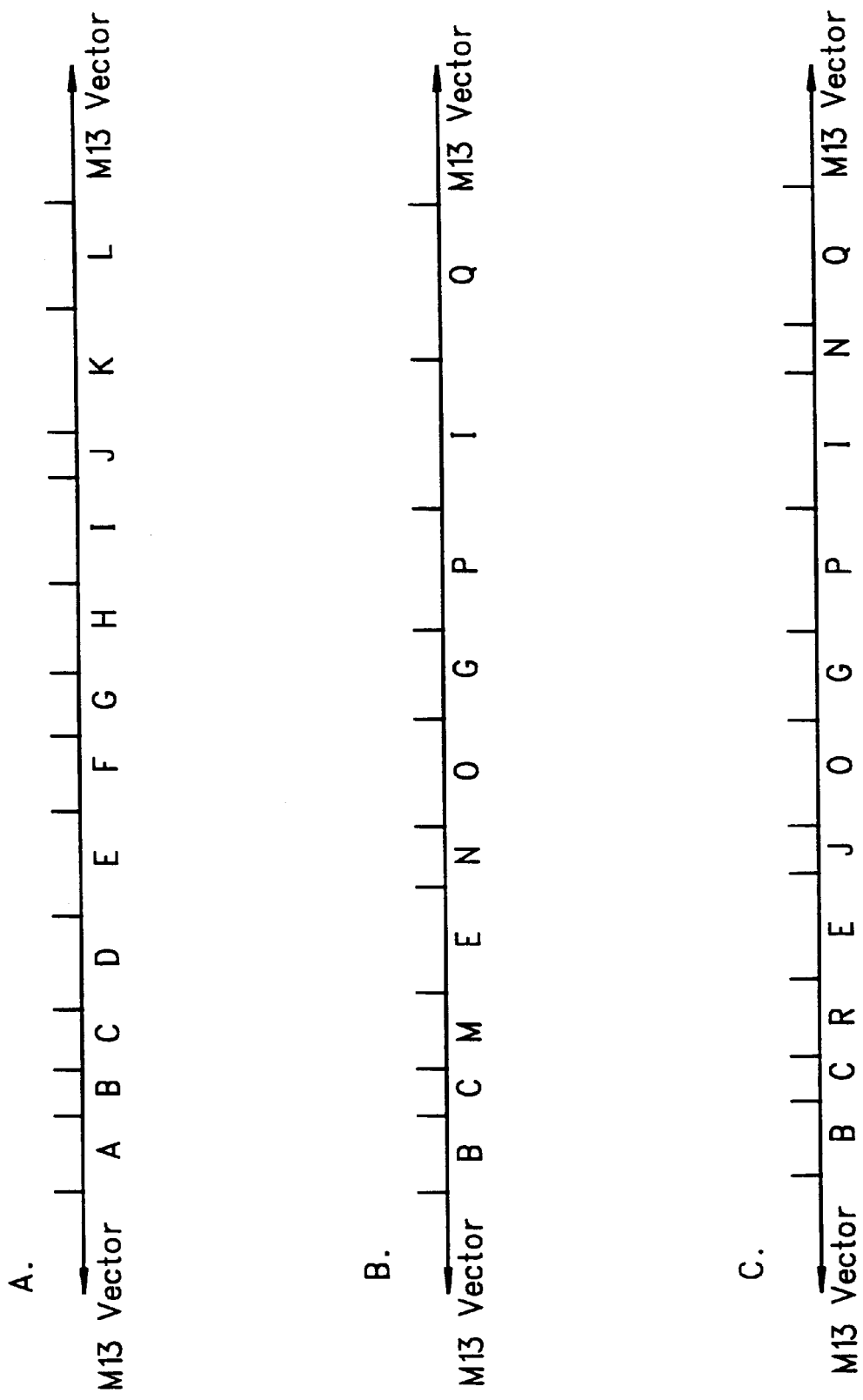
FIG. 3: Vectors used for cloning antibodies.

Many changes were made to BS11 to generate the cloning vector used in the present screening methods. The amber stop codon between the heavy chain and the pseudo gene VIII sequence was removed so that every heavy chain was expressed as a fusion protein with the gene VIII protein. This increased the copy number of the antibodies on the phage relative to BS11. A HindIII restriction enzyme site in the sequence between the 3' end of the L chain and the 5' end of the alkaline phosphatase signal sequence was deleted so antibodies could be subcloned into a pBR322 derivative (Example 21). The interchain cysteine residues at the carboxyl-terminus of the L and H chains were changed to serine residues. This increased the level of expression of the antibodies and the copy number of the antibodies on the phage without affecting antibody stability. Nonessential DNA sequences on the 5' side of the lac promoter and on the 3' side of the pseudo gene VIII sequence were deleted to reduce the size of the M13 vector and the potential for rearrangement. A transcriptional stop DNA sequence was added to the vector at the L chain cloning site in addition to the translational stop so that phage with only heavy chain proteins on their surface, which might bind nonspecifically in panning, could not be made. Finally, DNA sequences for protein tags were added to different vectors to allow enrichment for polyvalent phage by metal chelate chromatography (polyhistidine sequence) or by affinity purification using a decapeptide tag and a magnetic latex having an immobilized antibody that binds the decapeptide tag. The vector BS39 had a polyhistidine sequence at the 3' end of the kappa chain with no tag at the end of the heavy chain (FIG. 3B) BS45 had a polyhistidine sequence between the end of the heavy chain constant region and the pseudo-gene VIII sequence, and a decapeptide sequence at the 3' end of the kappa chain constant region (FIG. 3C).

Example 6

Preparation of Uracil Templates Used in Generation of Spleen Antibody Phage Libraries 1 mL of *E. coli* CJ236 (BioRAD, Hercules, Calif.) overnight culture was added to 50 ml 2×YT in a 250 mL baffled shake flask. The culture was grown at 37° C. to $OD_{600}$=0.6, inoculated with 10 µl of a 1/100 dilution of vector phage stock and growth continued for 6 hr. Approximately 40 mL of the culture was centrifuged at 12,000 rpm for 15 minutes at 4° C. The supernatant (30 mL) was transferred to a fresh centrifuge tube and incubated at room temperature for 15 minutes after the addition of 15 µl of 10 mg/ml RnaseA (Boehringer Mannheim, Indianapolis, Ind.). The phage were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12,000 rpm for 15 min at 2–8° C. The supernatant was carefully discarded, and the tube was briefly spun to remove all traces of supernatant. The pellet was resuspended in 400 µl of high salt buffer (300 mM NaCl, 100 mM Tris pH 8.0, 1 mM EDTA), and transferred to a 1.5 mL tube. The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14,000 rpm for 10 min at 4° C., the pellet washed once with cold 70% ethanol, and dried in vacuo. The uracil template DNA was dissolved in 30 µl sterile water and the concentration determined by $A_{260}$ using an absorbance of 1.0 for a concentration of 40 µg/ml. The template was diluted to 250 ng/µl with sterile water, aliquoted, and stored at −20° C.

Example 7

Mutagenesis of Uracil Template with ss-DNA and Electroporation into *E. coli* to Generate Antibody Phage Libraries Antibody phage-display libraries were generated by simultaneously introducing single-stranded heavy and light chain genes onto a phage-display vector uracil template. A typical mutagenesis was performed on a 2 µg scale by mixing the following in a 0.2 mL PCR reaction tube: 8 µl of (250 ng/µl) uracil template (examples 5 and 6), 8 µl of 10×annealing buffer (200 mM Tris pH 7.0, 20 mM $MgCl_2$, 500 mM NaCl), 3.33 µl of kinased single-stranded heavy chain insert (100 ng/µl), 3.1 µl of kinased single-stranded light chain insert (100 ng/ml), and sterile water to 80 µl. DNA was annealed in a GeneAmp® 9600 thermal cycler using the following thermal profile: 20 sec at 94° C., 85° C. for 60 sec, 85° C. to 55° C. ramp over 30 min, hold at 15 min. The DNA was transferred to ice after the program finished. The extension/ligation was carried out by adding 8 µl of 10×synthesis buffer (5 mM each dNTP, 10 mM ATP, 100 nM Tris pH 7.4, 50 mM $MgCl_2$, 20 mM DTT), 8 µl T4 DNA ligase (1 U/µl, Boehringer Mannheim, Indianapolis, Ind.), 8 µl diluted T7 DNA polymerase (1 U/µl, New England BioLabs, Beverly, Mass.) and incubating at 37° C. for 30 min. The reaction was stopped with 300 µl of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 µl of sterile water. 1 µl mutagenesis DNA was (500 ng) was transferred into 40 µl electrocompetent *E. coli* DH12S (Gibco/BRL, Gaithersburg, Md.) using the electroporation conditions in Example 8. The transformed cells were mixed with 1.0 mL 2×YT broth (Sambrook, et al., supra) and transferred to 15 mL sterile culture tubes. The first round antibody phage was made by shaking the cultures overnight at 23° C. and 300 rpm. The efficiency of the electroporation was measured by plating 10 µl of $10^{-3}$ and $10^{-4}$ dilutions of the cultures on LB agar plates (see Example 12). These plates were incubated overnight at 37° C. The efficiency was determined by multiplying the number of plaques on the $10^{-3}$ dilution plate by $10^5$ or multiplying the number of plaques on the $10^{-4}$ dilution plate by $10^6$. The overnight cultures from the electroporations were transferred to 1.5 ml tubes, and the cells were pelleted by centrifuging at 14,000 rpm for 5 min. The supernatant, which is the first round of antibody phage, was then transferred to 15 mL sterile centrifuge tubes with plug seal caps.

Example 8

Transformation of *E. coli* by Electroporation

The electrocompetent *E. coli* cells were thawed on ice. DNA was mixed with 20–40 µL electrocompetent cells by gently pipetting the cells up and down 2–3 times, being careful not to introduce air-bubbles. The cells were transferred to a Gene Pulser cuvette (0.2 cm gap, BioRAD, Hercules, Calif.) that had been cooled on ice, again being careful not to introduce an air-bubble in the transfer. The cuvette was placed in the *E. coli* Pulser (BioRAD, Hercules, Calif.) and electroporated with the voltage set at 1.88 kV according to the manufacturer's recommendation. The transformed sample was immediately diluted to 1 ml with 2×YT broth and processed as procedures dictate.

Example 9

Preparation of Biotinylated Antigens and Antibodies

Protein antigens or antibodies were dialyzed against a minimum of 100 volumes of 20 mM borate, 150 mM NaCl, pH 8 (BBS) at 2–8° C. for at least 4 hr. The buffer was changed at least once prior to biotinylation. Protein antigens or antibodies were reacted with biotin-XX-NHS ester (Molecular Probes, Eugene, Oreg., stock solution at 40 mM in dimethylformamide) at a final concentration of 1 mM for 1 hr at room temperature. After 1 hr, the protein antigens or antibodies were extensively dialyzed into BBS to remove unreacted small molecules.

Example 10

Preparation of Alkaline Phosphatase-antigen Conjugates

Alkaline phosphatase (AP, Calzyme Laboratories, San Luis Obispo, Calif.) was placed into dialysis versus a minimum of 100 volumes of column buffer (50 mM potassium phosphate, 10 mM borate, 150 mM NaCl, 1 mM $MgSO_4$, pH 7.0) at 2–8° C. for at least four hr. The buffer was changed at least twice prior to use of the AP. When the AP was removed from dialysis and brought to room temperature, the concentration was determined by absorbance at 280 nm using an absorbance of 0.77 for a 1 mg/mL solution. The AP was diluted to 5 mg/mL with column buffer. The reaction of AP and succinimidyl 4-(N-maleimidomethyl) cyclohexane-1-carboxylate (SMCC, Pierce Chemical Co., Rockford, Ill.) was carried out using a 20:1 ratio of SMCC:AP. SMCC was dissolved in acetonitrile at 20 mg/mL and diluted by a factor of 84 when added to AP while vortexing or rapidly stirring. The solution was allowed to stand at room temperature for 90 min before the unreacted SMCC and low molecular weight reaction products were separated from the AP using gel filtration chromatography (G50 Fine, Pharmacia Biotech, Piscataway, N.J.) in a column equilibrated with column buffer.

Protein antigen was dialyzed versus a minimum of 100 volumes of 20 mM potassium phosphate, 4 mM borate, 150 mM NaCl, pH 7.0 at 2–8° C. for at least four hr. The buffer was changed at least twice prior to use of the antigen. The amount of antigen was quantitated by absorbance at 280 nm. The extinction coefficient for creatine kinase MB subunits (CKMB, Scripps Laboratories, San Diego, Calif.) was 0.88 mL/mg-cm, Clostridium difficile toxin A (Tech Lab, Blacksburg, Va.) was 1.29 mL/mg-cm, and Clostridium difficile glutamate dehydrogenase (Example 19) was 1.45 mL/mg-cm. The reaction of antigen and N-succinimidyl 3-[2-pyridyldithio]propionate (SPDP, Pierce Chemical Co., Rockford, Ill.) was carried out using a 20:1 molar ratio of SPDP:antigen. SPDP was dissolved in dimethylformamide at 40 mM and diluted into the antigen solution while vortexing. The solution was allowed to stand at room temperature for 90 min, at which time the reaction was quenched by adding taurine (Aldrich Chemical Co., Milwaukee, Wis.) to a final concentration of 20 mM for 5 min. Dithiothreitol (Fisher Scientific, Pittsburgh, Pa.) was added to the protein at a final concentration of 1 mM for 30 min. The low molecular weight reaction products were separated from the antigen using gel filtration chromatography in a column equilibrated in 50 mM potassium phosphate, 10 mM borate, 150 mM NaCl, 0.1 mM ethylene diamine tetraacetic acid (EDTA, Fisher Scientific, Pittsburgh, Pa.), pH 7.0.

The AP and antigen were mixed together in an equimolar ratio. The reaction was allowed to proceed at room temperature for 2 hr. The conjugate was diluted to 0.1 mg/mL with block containing 1% bovine serum albumin (from 30% BSA, Bayer, Kankakee, Ill.), 10 mM Tris, 150 mM NaCl, 1 mM $MgCl_2$, 0.1 mM $ZnCl_2$, 0.1% polyvinyl alcohol (80% hydrolyzed, Aldrich Chemical Co., Milwaukee, Wis.), pH 8.0.

Example 11

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet. While still in the magnet, the liquid was carefully removed with a 10 mL sterile pipet. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 150 mM NaCl, 20 mg/mL BSA, 0.1% Tween 20 (Fisher Scientific, Pittsburgh, Pa.), pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 mL sterile pipet as described above. The magnetic latex was resuspended in 10 mL of panning buffer to begin the second wash. The magnetic latex was washed a total of 3 times with panning buffer. After the final wash, the latex was resuspended in panning buffer to the initial aliquot volume.

Example 12

Plating M13 Phage or Cells Transformed with Antibody Phage-display Vector Mutagenesis Reaction The phage samples were added to 200 μL of an overnight culture of E. coli XL1-Blue when plating on 100 mm LB agar plates or to 600 μL of overnight cells when plating on 150 mm plates in sterile 15 ml culture tubes. After adding LB top agar (3 mL for 100 mm plates or 9 mL for 150 mm plates, top agar stored at 55° C., Appendix A1, Molecular Cloning, A Laboratory Manual, (1989) Sambrook. J), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

Example 13

Develop Nitrocellulose Filters with Alkaline Phosphatase Conjugates

After overnight incubation of the nitrocellulose filters on LB agar plates, the filters were carefully removed from the plates with membrane forceps and incubated for 2 hr in either casein block (block with 1% casein (Hammersten grade, Research Organics, Cleveland, Ohio)), when using antigen-AP conjugates or block when using goat anti-mouse kappa-AP (Southern Biotechnology Associates, Inc, Birmingham, Ala.). After 2 hr, the filters were incubated with the AP conjugate for 2–4 hr. Antigen-AP conjugates were diluted into casein block at a final concentration of 1 μg/mL and goat anti-mouse kappa-AP conjugates were diluted into block at a final concentration of 1 μg/mL. Filters were washed 3 times with 40 mM TRIS, 150 mM NaCl, 0.05% Tween 20, pH 7.5 (TBST) (Fisher Chemical, Pittsburgh, Pa.) for 5 min each. After the final wash, the filters were developed in a solution containing 0.2 M 2-amino-2-methyl-1-propanol (JBL Scientific, San Luis Obispo, Calif.), 0.5 M TRIS, 0.33 mg/mL nitro blue tetrazolium (Fisher Scientific, Pittsburgh, Pa.) and 0.166 mg/mL 5-bromo-4-chloro-3-indolyl-phosphate, p-toluidine salt.

Example 14

Enrichment of Polyclonal Phage to CKMB with No Tags on the Heavy Chain and a Polyhistidine Sequence on the Kappa Chain This example describes multiple rounds of screening of a phage library to the antigen creatine kinase MB (M and B designate muscle and brain subunits). Some of the rounds of screening to CKMB were alternated with rounds of enrichment for phage displaying multiple copies of antibodies. The percentage of phage displaying any light chain, and the percentage of phage displaying Fab fragments with specific affinity for CKMB was measured after each round of screening to CKMB.

The first round antibody phage was prepared as described above using BS39 uracil template. Two electroporations of mutagenesis DNA had efficiencies of $9.7 \times 10^7$ PFU and $8.3 \times 10^7$ PFU. The phage from both electroporations were combined and diluted to 3.2 ml with panning buffer. The phage was aliquoted into 2-1 mL aliquots in 15 mL disposable sterile centrifuge tubes with plug seal caps. CKMB-biotin (10 $\mu$L, $10^{-6}$ M stock concentration) was added to each phage aliquot. The phage samples were incubated overnight at 2–8° C.

After the incubation, the phage samples were panned with avidin magnetic latex. The equilibrated avidin magnetic latex (see Example 11), 200 $\mu$L latex per sample, was incubated with the phage for 10 min at room temperature. After 10 min, approximately 9 mL of panning buffer was added to each phage sample, and the magnetic latex was separated from the solution using a magnet. After 10 min in the magnet, the unbound phage was carefully removed with a 10 mL sterile pipet. The magnetic latex was then resuspended in 10 mL of panning buffer to begin the second wash. The latex was washed a total of 5 times as described above. For each wash, the tubes were in the magnet for 10 min to separate unbound phage from the magnetic latex. After the 5th wash, the magnetic latex was resuspended in 1 mL TBS and transferred to a 1.5 mL tube. Aliquots of the latex were taken at this point to plate on 100 mm LB agar plates as described above. The bulk of the magnetic latex (99%) was resuspended in 200 $\mu$L 2×YT and was plated on a 150 mm LB agar plate as described in Example 12. The 100 mm LB agar plates were incubated at 37° C. for 6–7 hr, then the plates were transferred to room temperature and nitrocellulose filters (pore size 0.45 $\mu$m, BA85 Protran, Schleicher and Schuell, Keene, N.H.) were overlayed onto the plaques. Plates with nitrocellulose filters were incubated overnight at room temperature. The 150 mm plates were used to amplify the phage binding to the magnetic latex to generate the next round of antibody phage. These plates were incubated at 37° C. for 4 hr, then overnight at 20° C.

After the overnight incubation, the antibody phage was eluted from the 150 mm plates, and the filters were developed with alkaline phosphatase-CKMB as described in Example 13. The antibody phage was eluted from the 150 mm plates by pipeting 8 mL 2YT media onto the lawn and gently shaking the plate at room temperature for 20 min. The phage were transferred to a 15 mL disposable sterile centrifuge tubes with plug seal cap and the debris from the LB plate was pelleted by centrifuging for 15 min at 3500 rpm. The 2nd round antibody phage was then transferred to a new tube.

To begin the 2nd round of panning, the antibody phage were titered by plating 10 $\mu$L of $10^{-7}$ and $10^{-8}$ dilutions of the phage on 100 mm LB agar plates. The plates were incubated at 37° C. for 6–7 hr, then the number of plaques on the plates were counted. Also, to monitor the percentage of kappa positives in the antibody phage, a nitrocellulose filter was overlayed onto the plate and incubated overnight at room temperature. The percentage of kappa positives is a measure of the proportion of phage displaying intact Fab fragments.

Both 2nd round antibody phage samples were pooled by diluting each ample into panning buffer at a final concentration of $5 \times 10^9$ PFU/mL to a final volume of 1 mL. (The titers of the antibody phage were about $2 \times 10^2$ PFU/mL and $1.7 \times 10^{12}$). CKMB-biotin (10 $\mu$L, $10^{-6}$ M stock concentration) was added to the phage and the phage was incubated at 2–8° C. overnight. The nitrocellulose filters on the antibody phage titer plates were developed with goat anti-mouse kappa AP as described in Example 13. The second round antibody phage was panned with avidin magnetic latex as described above. After washing the latex with panning buffer, the latex was resuspended in 1 mL TBS and transferred to a 1.5 mL tube. Aliquots of the latex were plated on 100 mm LB agar plates as described above to check functional positives, and the rest of the latex was plated on 150 mm LB agar plates to generate the 3rd round antibody phage. This general procedure of titering the antibody phage, diluting the phage into panning buffer and adding CKMB-biotin, incubating the phage at least 16 hr at 2–8° C., panning the phage with avidin magnetic latex, and plating the magnetic latex was followed through 10 rounds of panning. The only changes from that described above is the concentration of CKMB-biotin was lower to increase the affinity of bound antibodies, and the number of phage panned was between $10^{10}$ and $10^8$. The results of the filter lifts on the percentage of kappa positives in the antibody phage and the percentage of functional antibodies binding to the magnetic latex are shown in Table 2.

After the 10th round of panning to CKMB-biotin, the antibody phage were subject to a round of enrichment for polyvalent display. Enrichment was effected by binding of the hexahistidine tag fused to the displayed light chain to Ni NTA agarose (Qiagen Inc., Chatsworth, Calif.). The 11th round antibody phage (2.5 mL) were diluted into 2.5 mL panning buffer in a 15 mL disposable sterile centrifuge tube with plug seal cap. The Ni NTA was equilibrated into panning buffer using the following procedure. The resin (1 mL per phage sample) was diluted to 50 mL with panning buffer in a 50 mL disposable sterile centrifuge tube with plug seal cap and then was pelleted in an IEC centrifuge at 500 rpm for 1 min. The supernatant was carefully removed with a 50 mL disposable pipet, then the resin was again diluted to 50 mL with panning buffer for the second wash. The resin was washed in this manner a total of 4 times in order to equilibrate the resin in panning buffer. The equilibrated resin was then resuspended to its original volume with panning buffer. Equilibrated resin (1 mL) was then added to the phage, and the tube was gently rocked for 15 min. After 15 min, the resin was pelleted in an IEC centrifuge at 500 rpm for 1 min. The supernatant was gently removed with a 10 mL disposable pipet, and the resin was resuspended in 10 mL panning buffer for the first wash. The resin was pelleted as described above, the supernatant was removed, and the resin was resuspended a 2nd time in 10 mL panning buffer. This procedure was repeated for a total of 5 panning buffer washes. After the 5th wash was removed, the resin was resuspended in 1 mL of elution buffer (50 mM citrate, 150 mM NaCl, pH 4.0) and transferred to a 1.5 mL tube. The resin was gently rocked for 1 hr to elute the antibody phage. After 1 hr, the resin was pelleted (14,000 rpm in Eppendorf centrifuge for 5 min), and the phage was removed while being careful not to transfer any resin. In order to adjust the pH of the phage solution to 8, 50 µL of 1 M Tris, pH 8.3 and 46 µL of 1 M NaOH were added to the 1 mL phage sample. Also, 10 µL of 300 mg/mL bovine serum albumin (Bayer, Kankakee, Ill.) was added to the phage sample. The resulting phage solution (1 mL) was transferred to a 15 mL disposable sterile centrifuge tube with plug seal cap for the 11th round of panning with CKMB-biotin, as described above. As shown in Table 2, panning the antibody phage with Ni NTA prior to panning to CKMB significantly increased the percentage of CKMB functional positives binding to the avidin magnetic latex.

The 12th–14th rounds of panning were done as described above, where the antibody phage was bound to Ni NTA, eluted, and the eluted phage panned with CKMB-biotin. However, in round 13, unlabelled creatine kinase BB subunits (Scripps Laboratories, San Diego, Calif.) and creatine kinase MM subunits (Scripps Laboratories, San Diego, Calif.) were added to the phage eluted from the Ni NTA at 100-fold molar excess to the CKMB-biotin to select antibodies that specifically bind to CKMB without binding to CKMM or CKBB. The percentage of functional CKMB antibodies was 25 greater than 95% by round 13.

TABLE 2

Summary of kappa positives and CKMB functional positives at each round of panning

| antibody phage % kappa | round # | phage binding to avidin latex % functional |
|---|---|---|
| 202/253 (80%) | 1 | 0/32 (0%) |
| 175/234 (75%) | 2 | 0/129 (0%) |
| 87/120 (73%) | 3 | 4/79 (5.1%) |
| 81/165 (49%) | 4 | 35/409 (8.6%) |
| 149/342 (44%) | 5 | 5/31 (16%) |
| 40/192 (21%) | 6 | 30/400 (7.5%) |
| 1/54 (2%) | 7 | 6/54 (11%) |
| 6/106 (6%) | 8 | 4/46 (9%) |
| 35/93 (38%) | 9 | 19/551 (3%) |
| 14/191 (7%) | 10 | 18/400 (5%) |
| N/A | 11 | 349/553 (63%) |
| 96/100 (96%) | 12 | 232/290 (80%) |
| 31/31 (100%) | 13 | (>95%) |
| 147/149 (99%) | 14 | 400/405 (99%) |

Table 2 illustrates the importance of polyvalent enrichment for making phage libraries with a high proportion of phage displaying antibodies with specific affinity for the chosen target (functional positives). The percentage of phage with specific affinity for the selected target is zero after the first two rounds of panning but then increase to about ten percent before leveling off in subsequent rounds of panning through round ten. Then in rounds 11–14, which are performed concurrently with polyvalent enrichment, the percentage of functional positive phage increases to 99%. The rapid increase in functional positive phage in rounds 11–14, in which polyvalent enrichment is performed, compared with the plateau of about 10% achieved in rounds 1–10 without polyvalent enrichment illustrates the power of the present methods to achieve libraries with a high percent of functional positives.

The variation in percent kappa positives in different rounds of screening is also instructive. The percentage is initially high but decreases in the first ten rounds of screening (which are not performed concurrently with polyvalent enrichment). The decrease arises because kappa negative phage grow faster than kappa positive phage and are preferentially amplified between rounds of panning. In rounds 11–14, the percent of kappa positives increases to near 100%. The increase is due to polyvalent selection, which is effected by screening for phage displaying at least two kappa chains.

Example 15

Enrichment of Polyclonal Phage to *Clostridium Difficile* Toxin A with a Polyhistidine Tag on the Heavy Chain: Selection of an Epitope Specificity on Toxin A Different from a Reference Antibody The first round antibody phage was prepared as described in Example 7 using BS45 uracil template. Eight electroporations of mutagenesis DNA were performed yielding 8 different phage samples. To create more diversity in the polyclonal library, each phage sample was panned separately. The antibody phage (about 0.9 mL) from each electroporation was transferred to a 15 mL disposable sterile centrifuge tube with plug seal cap. BSA (30 μL 300 mg/mL solution) and 1 M Tris (50 μL, 1 M stock solution, pH 8.0) were added to each phage stock, followed by 10 μL $10^{-6}$ M toxin A-biotin. The antibody phage was allowed to come to equilibrium with the toxin A-biotin by incubating the phage at 2–8° C. overnight. After the incubation, the phage were panned with avidin magnetic latex as described above in Example 14, except only 4 panning buffer washes were performed instead of 5. The entire magnetic latex of each sample was plated on 150 mm LB plates to generate the 2nd round antibody phage. The 150 mm plates were incubated at 37° C. for 4 hr, then overnight at 20° C.

The 2nd round antibody phage were eluted from the 150 mm plates as described in Example 14 except 10 mL 2×YT was used to elute the phage instead of 8 mL. The second round of panning was set up by diluting 100 μL of each phage stock (8 total) into 900 μL panning buffer in 15 mL disposable sterile centrifuge tubes with plug seal cap. Toxin A-biotin (10 μL of $10^{-7}$ M) was added to each sample, and the phage were incubated overnight at 2–8° C. The antibody phage were not titered before panning as described in Example 14. The phage samples were panned with avidin magnetic latex following the overnight incubation. After washing the latexes with panning buffer, each latex was plated on 150 mm LB agar plates. The plates were incubated at 37° C. for 4 hr, then 20° C. overnight.

The 3rd round antibody phage were bound to Ni NTA resin and eluted prior to panning with toxin A-biotin. Each phage sample was bound to Ni NTA and washed with panning buffer as described in Example 14. After the final wash, the antibody phage was eluted by adding 0.8 mL 300 mM imidazole (Fisher Scientific, Pittsburgh, Pa.) in panning buffer to each sample, and rocking the tubes for 10 min at room temperature. The resin was pelleted by centrifuging the tubes at 14,000 rpm for 5 min at room temperature, and the phage were carefully transferred to new tubes. Each phage sample was diluted to about 1.1 mL with panning buffer, then 1 mL of each sample was transferred to 15 mL disposable sterile centrifuge tube with plug seal cap. Toxin A-biotin (10 μL of $10^{-7}$ M) was added to each sample, and the phage were incubated overnight at 2–8° C. After the overnight incubation, the phage were panned with avidin magnetic latex. After washing, each latex was resuspended in 1 mL panning buffer, and aliquots of each latex were plated on 100 mm LB agar plates to determine the percentage of kappa positives or functional positives. The majority of latex from each panning (99%) was plated on 150 mm LB agar plates to amplify the phage binding to the latex (see Example 14).

Two nitrocellulose filters from the 3rd round of panning were developed with goat anti-mouse kappa AP and had 83% and 85% positives. Six filters developed with toxin A-AP were all between 39–47% functional positive. At this point, 10 μL of $10^{-7}$ and 20 μL of $10^{-8}$ dilutions of each antibody phage stock were plated on 100 mm LB plates to determine the titers of each phage stock. The titers of the phage stocks were determined prior to pooling so that phage stocks with very high titers did not bias the antibody phage library. The titers (PFU/mL) were determined by counting the number of plaques on each plate and multiplying that number by $10^9$ ($10^{-7}$ dilution plate) or $5\times10^9$ ($10^{-8}$ dilution plate). Once the titers were determined, $2\times10^{11}$ PFU from each phage stock was pooled. The pooled phage (1.5 mL) was diluted to 5 mL with panning buffer, then the phage was panned with Ni NTA. The eluted phage was panned to toxin A in the presence of an antibody to toxin A, PCG4 (described U.S. Pat. No. 4,533,630), to screen for phage-antibodies to toxin A that have a different specificity than PCG4. The eluted phage was diluted to about 1.1 mL with panning buffer, and 1 mL was aliquoted into a 15mL tube. In a 1.5 mL tube, unlabeled toxin A (7.5 μL, $10^{-7}$ M) and biotinylated PCG4 (15 μL, $10^{-6}$ M) were mixed and incubated at room temperature for 15 min. A 20-fold molar excess of biotinylated antibody over toxin A was used so that no antibody phage could bind at the PCG4 epitope. The mixture of toxin A and biotinylated antibody (15 μL) was added to the 1 mL phage and incubated overnight at 2–8° C. The phage sample was panned with avidin magnetic latex as described in Example 14.

The process of panning the eluted antibody phage, binding and eluting the phage with Ni NTA, and panning the resulting eluted phage with biotinylated PCG4/toxin A was repeated 4 times. After the 5th round of selection, the polyclonal antibody phage stock complementary to PCG4 was 99% kappa positive and 98% had specific affinity for toxin A by plaque lift analysis.

Example 16

Cloning of *Clostridium difficile* Glutamate Dehydrogenase (the Target for Panning in Example 17)

PCR primers were made corresponding to the coding sequence at the 5'-end of glutamate dehydrogenase, and the coding sequence at the 3'-end of glutamate dehydrogenase, including six histidine codons inserted between the end of the coding sequence and the stop codon to assist in purification of the recombinant protein by metal-chelate chromatography, primers Q and R, respectively (Table 3). In addition, the 5' primer contains 20 base-pairs of vector sequence at its 5'-end corresponding to the 3'-end of the pBRnsiH3 vector. The 3' primer contains the 19 base-pairs of tet promoter removed by HindIII digestion, in addition to 20 base-pairs of vector sequence 3' to the HindIII site at its 5' end (Example 21).

The PCR amplification of the glutamate dehydrogenase gene insert was done on a 100 μl reaction scale containing 100 pmol of 5' primer (Q), 100 pmol of 3' primer (R), 2 units of Expand polymerase, 10 μl 2 mM dNTPs, 10 μl 10×Expand reaction buffer, 1 μl *C. difficile* genomic DNA (75 ng) as template, and water to 100 μl. The reaction was carried out in a Perkin-Elmer thermal cycler as described in Example 22. The PCR products were precipitated and fractionated by agarose gel electrophoresis and full-length products excised from the gel, purified, and resuspended in water (Example 21). The insert and NsiI/HindIII digested pBRnsiH3 vector were prepared for T4 exonuclease digestion by adding 1.0 μl of 10×Buffer A to 1.0 μg of DNA and bringing the final volume to 9 μl with water. The samples were digested for 4 min at 30° C. with 1 μl (1U/μl)of T4 DNA polymerase. The T4 DNA polymerase was heat inactivated by incubation at 70° C. for 10 min. The samples were cooled, briefly spun, and 70 ng of the digested insert added to 100 ng of digested pBRnsiH3 vector in a fresh microfuge tube. After the addition of 1 μl of 10×annealing buffer, the volume was brought to 10 μl with water and the mixture heated to 70° C. for 2 min and cooled over 20 min to room temperature. The annealed DNA was diluted one to four with distilled water and electroporated (Example 8) into 30 μl of electrocompetent *E. coli* strain, DH10B. The transformed cells were diluted to 1.0 ml with 2×YT broth and 10 μl, 100 μl and 300 μl plated on LB agar plates supplemented with tetracycline (10 μg/ml) and grown overnight at 37° C. Clones were picked and grown overnight in 2×YT (10 μg/ml tetracycline) at 37° C. The following day glycerol freezer stocks made for long term storage at −80° C. The glutamate dehydrogenase clone was grown and purified on a preparative scale as described in Example 24.

Example 17

Enrichment of Polyclonal Phage to *Clostridium difficile* Glutamate Dehydrogenase Using a Decapeptide Tag on the Kappa Chain The first round antibody phage was prepared as described in Example 7 using BS45 uracil template, which has a hexahistidine tag for polyvalent enrichment fused to the heavy chain of displayed Fabs. Twelve electroporations of mutagenesis DNA from 4 different spleens (3 electroporations from each spleen) yielded 12 different phage samples. Each phage sample was panned separately to create more diversity in the polyclonal library. The antibody phage (about 0.9 mL) from each electroporation was transferred to a 15 mL disposable sterile centrifuge tube with plug seal cap. BSA (30 μL of a 300 mg/mL solution) and 1 M Tris (50 μL, pH 8.0) were added to each phage stock, followed by 10 μL $10^{-7}$ M glutamate dehydrogenase-biotin (Example 16). The antibody phage was allowed to come to equilibrium with the glutamate dehydrogenase-biotin by incubating the phage at room temperature for 4 hr. After the incubation, the phage samples were panned with avidin magnetic latex as described in Example 14. The entire latex of each sample was plated on 150 mm LB agar plates to generate the 2nd round antibody phage (Example 14). The resulting phage were panned with glutamate dehydrogenase-avidin-magnetic latex as described for the first round of panning.

A procedure was developed to enrich the antibody phage using the decapeptide tag on the kappa chain and a monoclonal antibody magnetic latex that binds the decapeptide. Binding studies had previously shown that the decapeptide could be eluted from the monoclonal antibody 7F11 (see Example 25) at a relatively mild pH of 10.5–11. The third round antibody phage resulting from panning Ni NTA enriched 2nd round phage were bound to the 7F11 magnetic latex and eluted as described below. The 7F11 magnetic latex (2.5 mL) was equilibrated with panning buffer as described above for the avidin magnetic latex. Each phage stock (1 mL) was aliquoted into a 15 mL tube. The 7F11 magnetic latex (200 μL per phage sample) was incubated with phage for 10 min at room temperature. After 10 min, 9 mL of panning buffer was added, and the magnetic latex was separated from unbound phage by placing the tubes in a magnet for 10 min. The latexes were washed with 1 additional 10 mL panning buffer wash. Each latex was resuspended in 1 mL panning buffer and transferred to 1.5 mL tubes. The magnetic latex was separated from unbound phage by placing the tubes in a smaller magnet for 5 min, then the supernatant was carefully removed with a sterile pipet. Each latex was resuspended in 1 mL elution buffer (20 mM 3-(cyclohexylamino)propanesulfonic acid (United States Biochemical, Cleveland, Ohio), 150 mM NaCl, 20 mg/mL BSA, pH 10.5) and incubated at room temperature for 10 min. After 10 min, tubes were placed in the small magnet again for 5 min and the eluted phage was transferred to a new 1.5 mL tube. The phage samples were again placed in the magnet for 5 min to remove the last bit of latex that was transferred. Eluted phage was carefully removed into a new tube and 25 $\mu$L 3 M Tris, pH 6.8 was added to neutralize the phage. Panning with glutamate dehydrogenase-biotin was set up for each sample by mixing 900 $\mu$L 7F11/decapeptide enriched phage, 100 $\mu$L panning buffer, and 10 $\mu$L $10^{-7}$ M glutamate dehydrogenase-biotin and incubating overnight at 2–8° C. The phage was panned with avidin magnetic latex as described in Example 14.

One of the functional positive plaques was arbitrarily picked off an LB agar plate, and the antibody was subcloned into the expression vector described in Example 22. The monoclonal antibody was used as a reference to isolate polyclonal antibodies having different epitope specificity than the monoclonal antibody for sandwich assay development. This is similar to what is described above for toxin A except the monoclonal antibody for toxin A was a hybridoma antibody from a commercial source and the monoclonal antibody described here is from the antibody phage library.

The resulting 4th round antibody phage was panned again with 7F11 magnetic latex prior to functional panning. The eluted phage samples were set up for panning with the biotinylated monoclonal antibody (CD.43.9) and unlabelled glutamate dehydrogenase as described in Example 15 for toxin A antibodies. As discussed above, the monoclonal antibody was picked from the phage library and a polyclonal antibody phage stock that was complementary to the monoclonal was needed. Mixed the monoclonal antibody biotin (125 $\mu$L, $10^{-6}$M) and glutamate dehydrogenase (125 $\mu$L, $5\times10^{-8}$ M) at room temperature for 15 min. Added 20 $\mu$L of the mixture to each 1 mL phage sample (0.7 mL panning buffer and 0.3 mL phage eluted from the 7F11 latex), and incubated the samples overnight at 2–8° C. The phage samples were panned with the avidin magnetic latex following the standard procedure.

The 5th round antibody phage were eluted from the 150 mm LB agar lates as described in Example 15. The antibody phage were titered by plating 10 $\mu$L $10^{-7}$ dilutions of each phage stock on 100 mm LB agar plates. After 6 hr at 37° C., the number of plaques on each plate was counted, and the titers were calculated by multiplying the number of plaques by $10^9$. A pool of ten fifth round phage was made by mixing an equal number of phage from each phage stock so that high titer phage stocks would not bias the pool. Two of the samples were discarded because they had low functional percentages by plaque lift. The pooled phage were panned with 7F11 magnetic latex as described above. The eluted phage was set up for panning by mixing 0.1 mL panning buffer, 0.9 mL 7F11 eluted phage, and 20 $\mu$L monoclonal antibody biotin/glutamate dehydrogenase (see above). Phage were incubated overnight at 2–8° C. The phage sample was panned with avidin magnetic latex following the standard procedure. The phage binding to the latex was 97% functional positive by plaque lift assay.

Example 18

Enrichment of Polyclonal Page to Human Vascular Endothelial Growth Factor 165

The immunization of vascular endothelial growth factor 165 ($VEGF_{165}$, R&D Systems, Minneapolis, Minn.), purification of RNA, preparation of cDNA, and amplification of cDNA by PCR were done as described in Examples 1,2 and 3. The ss-DNA was purified by HPLC and kinased as described in Example 4 with the following changes in the HPLC gradient shown in Table 1. The time to 85% B was changed from 32 min to 17 min, the time to 100% B was changed from 35 min to 18 min, and every time after 35 min was decreased by 17 min. The total time for the HPLC program was decreased from 52 min to 35 min. Mutagenesis of the BS45 uracil template was done as described in Example 7 with the following exceptions. The kinased heavy chain ss-DNA from 4 different spleens (5 $\mu$L of 100 ng/$\mu$L from each spleen) was pooled, and separately the kinased kappa chain ss-DNA from 4 different spleens (5 $\mu$L of 100 ng/$\mu$L from each spleen) was pooled. The pooled ss-DNA was used in the mutagenesis of BS45 instead of ss-DNA from individual spleens. Four electroporations of the mutagenesis DNA were done as described in Example 8 except the transformed samples were resuspended in 400 $\mu$L 2XYTand 600 $\mu$L overnight XL1 cells instead of 1 mL of 2XYT. The first round antibody phage samples were generated by plating the electroporated samples on 150 mm LB plates as described in Example 12 except no lawn cells were added. The plates were incubated at 37° C. for 4hr, then 20° C. overnight. The first round antibody phage was eluted from the 150 mm plates by pipeting 10 mL 2YT media onto the lawn and gently shaking the plate at room temperature for 20 min. The phage were transferred to 15 mL disposable sterile centrifuge tubes with plug seal cap and the debris from the LB plate was pelleted by centrifuging for 15 min at 3500 rpm. The four $1^{st}$ round antibody phage samples were then transferred to new tubes.

Prior to functional panning, the antibody phage samples were enriched for polyvalent display using the decapeptide tag on the kappa chain and the 7F11 magnetic latex, as described in Example 17. The same procedure was followed except one 9 mL panning buffer wash and two 1 mL panning buffer washes were done instead of that described in Example 17. The first round of panning was set up with biotinylated VEGF at $10^{-9}$ M final concentration. The antigen was biotinylated as described in Example 9. The functional panning was done as described in Example 14 except there were only one 10 mL panning buffer wash and three 1 mL panning buffer washes of the avidin magnetic latex prior to plating the latexes on LB plates. The entire latex of each sample was plated on 150 mm LB plates to generate the 2nd round antibody phage. The 150 mm plates were incubated at 37° C. for 4 hr, then overnight at 20° C.

The resulting $2^{nd}$ round antibody phage samples were set up for the second round of functional panning in separate 15 mL disposable sterile centrifuge tubes with plug seal cap by mixing 900 $\mu$L panning buffer, 100 $\mu$L $2^{nd}$ round antibody phage, and 10 $\mu$L $10^{-6}$M VEGF-biotin. After 1 hr at room temperature, the phage samples were panned with avidin magnetic latex as described above. An aliquot of one sample was plated on a 100 mm LB agar plate to determine the percentage of kappa positives, as described in Example 14. The percentage of kappa positives was 84%.

The 3rd round antibody phage was eluted from the plates and a third round of functional panning was set up as described above using 950 μL panning buffer, 50 μL 3$^{rd}$ round antibody phage, and 10 μL 10$^{-6}$M VEGF-biotin. After incubation for 46 hours at 2–8° C., the phage samples were panned with avidin magnetic latex and aliquots of each sample were plated to determine the percentage of kappa positives, as described above. The percentage of kappa positives was between 57–74%.

The 4th round antibody phage samples were titered by plating 40 μL 10$^{-8}$ dilutions on 100 mm LB plates. After 6hr at 37° C., the number of plaques on each plate was counted. A pool of 4th round phage was made by mixing an equal number of phage from each phage stock, so that high titer phage stocks would not bias the pool. The pooled antibody phage was panned with 7F11 magnetic latex as described above, and the eluted phage was set up for functional panning by adding VEGF-biotin to a final concentration of 10$^{-9}$M. After allowing the mixture to come to equilibrium, the phage sample was panned with avidin magnetic latex as described above.

The eluted 5$^{th}$ round phage was set up in duplicate for a 5$^{th}$ round of functional panning as described above using 950 μL panning buffer, 50 μL 5$^{th}$ round pooled-antibody phage. One sample (foreground) received 10 μL 10$^{-7}$M VEGF-biotin, and the other sample (background) did not receive antigen and served as a blank to monitor non-specific binding of phage to the magnetic latex. After incubation for 18 hours at 2–8° C., the phage samples were panned with avidin magnetic latex as described above. The next day, the 6$^{th}$ round antibody phage was eluted and the number of plaques was counted on the foreground and background plates. The foreground:background ratio was 134:1.

Example 19

Preparation of M13 Cloning Vector with Human Constant Region Sequences

The mouse heavy and kappa constant region sequences were deleted from BS45 by oligonucleotide directed mutagenesis. Oligonucleotide 864 was used to delete the mouse kappa chain and oligonucleotide 862 was used to delete the mouse heavy chain.

Oligonucleotide 864 (SEQ ID NO:67)

5' ATC TGG CAC ATC ATA TGG ATA AGT TTC GTG TAC AAA ATG CCA GAC CTA GAG GAA TTT TAT TTC CAG CTT GGT CCC

Oligonucleotide 862 (SEQ ID NO:68)

5' GTG ATG GTG ATG GTG ATG GAT CGG AGT ACC AGG TTA TCG AGC CCT CGA TAT TGA GGA GAC GGT GAC TGA

Deletion of both constant region sequences was determined by amplifying the DNA sequence containing both constant regions by PCR using oligonucleotides 5 and 197, followed by sizing the PCR products on DNA agarose gel. The PCR was accomplished as described in Example 3 for the double-stranded DNA, except 1 μL of phage was template instead of cDNA. Phage with the desired deletion had a shorter PCR product than one deletion or no deletion. Uracil template was made from one phage stock having both deletions, as described in Example 6. This template, BS50, was used to insert the human constant region sequences for the kappa chain and IgG1.

Primer 5 (SEQ ID NO:69)

5' GCA ACT GTT GGG AAG GG

Primer 197 (SEQ ID NO:70)

5' TC GCT GCC CAA CCA GCC ATG

The human constant region DNA sequences were amplified from human spleen cDNA (Clontech, Palo Alto, Calif.). Oligonucleotides 869 and 870 were used to amplify the kappa constant region sequence, and oligonucleotides 867 and 876 were used to amplify the IgG1 constant region sequence and the codons for 6 amino acids of the hinge region (Kabat et al., Sequences of Proteins of Immunological Interest, 1991).

5' PCR primer (869)—(SEQ ID NO:71) GGG ACC AAG CTG GAA ATA AAA CGG GCT GTG GCT GCA CCA TCT GTC T 3' PCR primer (870)—(SEQ ID NO:72) ATC TGG CAC ATC ATA TGG ATA AGA CTC TCC CCT GTT GAA GCT CTT 5' PCR primer (867)—(SEQ ID NO:73) TCA GTC ACC GTC TCC TCA GCC TCC ACC AAG GGC CCA TC 3' PCR primer (876)—(SEQ ID NO:74) GTG ATG GTG ATG GTG ATG AGA TTT GGG CTC TGC TTT CTT GTC C PCR (1–50 μL reaction for each chain) was performed using Expand high-fidelity PCR system (Roche Molecular Biochemicals, Indianapolis, Ind.). Each 50 μL reaction contained 50 pmol of 5' primer, 50 pmol of 3' primer, 0.35 units of Expand DNA polymerase, 5 μL 2 mM dNTP's, 5 μL 10×Expand reaction buffer, 1 μL cDNA as template, and water to 50 μL. The reaction was carried out in a Perkin-Elmer thermal cycler (Model 9600) using the following thermal profile for the kappa chain: one cycle of denaturation at 94° C. (1 min); ten cycles of denaturation (15 sec, 94° C.), annealing (30 sec, 55° C.), elongation (60 sec, 72° C.); fifteen cycles of denaturation (15 sec, 94° C.), annealing (30 sec, 55° C.), elongation (80 sec plus 20 sec for each additional cycle, 72° C.); elongation (6 min, 72° C.); soak (4° C., indefinitely). The thermal profile used for the heavy chain reaction had twenty cycles instead of fifteen in the second part of the thermal profile.

The dsDNA products of the PCR process were then subjected to asymmetric PCR using only 3' primer to generate substantially only the anti-sense strand of the human constant region genes, as described in Example 3. Five reactions were done for the kappa chain and ten reactions were done for the heavy chain (100 μL per reaction). The thermal profile for both constant region genes is the same as that described in Example 3, including the heavy chain asymmetric PCR was done with 30 cycles and the kappa chain asymmetric PCR was done with 25 cycles. The single stranded DNA was purified by HPLC as described in Example 4. The HPLC purified kappa chain DNA was dissolved in 55 μL of water and the HPLC purified heavy chain was dissolved in 100 μL of water. The DNA was quantified by absorbance at 260 nm, as described in Example 4, then the DNA was kinased as described in Example 4 except added 6 μL 10×kinase buffer, 2.6 μL 10 mM ATP, and 0.5 μL of polynucleotide kinase to 50 μL of kappa chain DNA. Twice those volumes of kinase reagents were added to 100 μL of heavy chain DNA.

The kinased DNA was used to mutate BS50 without purifying the DNA by extractions. The mutagenesis was performed on a 2 μg scale by mixing the following in a 0.2 mL PCR reaction tube: 8 μl of (250 ng/μl) BS50 uracil template, 8 μl of 10×annealing buffer (200 mM Tris pH 7.0, 20 mM MgCl$_2$, 500 mM NaCl), 2.85 μl of kinased single-stranded heavy chain insert (94 ng/μl), 6.6 μl of kinased single-stranded kappa chain insert (43.5 ng/μl), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10×synthesis buffer (5 mM each dNTP, 10 mM ATP, 100 mM Tris pH 7.4, 50 mM MgCl$_2$, 20 mM DTT), 8 μl T4 DNA ligase (1 U/μl, Roche Molecular Biochemicals, Indianapolis, Ind.), 8 μl diluted T7 DNA polymerase (1 U/μl, New England BioLabs, Beverly, Mass.) and incubating at 37° C. for 30 min. The reaction was stopped with 296 μl of mutagenesis stop buffer (10 mM Tris pH 8.0, 10 mM EDTA). The mutagenesis DNA was extracted once with equilibrated phenol (pH>8) :chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl of sterile water. 1 μl mutagenesis DNA was (500 ng) was transferred into 40 μl electrocompetent *E. coli* DH12S (Gibco/BRL, Gaithersburg, Md.) using the electroporation conditions in Example 8. The transformed cells were mixed with 1.0 mL 2×YT broth (Sambrook, et al., supra) and transferred to a 15 mL sterile culture tube. Aliquots (10 μL of $10^{-3}$ and $10^{-4}$ dilutions) of the transformed cells were plated on 100 mm LB agar plates as described in Example 11. After 6 hr of growth at 37° C., 20 individual plaques were picked from a plate into 2.75 mL 2×YT and 0.25 ml overnight XL1 blue cells. The cultures were grown at 37° C., 300 rpm overnight to amplify the phage from the individual plaques. The phage samples were analyzed for insertion of both constant regions by PCR using oligonucleotides 197 and 5 (see above in BS50 analysis), followed by sizing of the PCR products by agarose gel electrophoresis. The sequence of two clones having what appeared to be two inserts by agarose gel electrophoresis was verified at MacConnell Research (San Diego, Calif.) by the dideoxy chain termination method using a Sequatherm sequencing kit (Epicenter Technologies, Madison, Wis.) and a LI-COR 4000L automated sequencer (LI-COR, Lincoln, Nebr.). Oligonucleotide primers 885 and 5, that bind on the 3' side of the kappa chain and heavy chain respectively, were used. Both clones had the correct sequence. The uracil template having human constant region sequences, called BS46, was prepared as described in Example 6.

Primer 885 (SEQ ID NO:75)

5' TAA GAG CGG TAA GAG TGC CAG

Example 20

Preparation of Chimeric Omniclonal to VEGF from Mouse Phage Library

The variable region sequences of the phage library from Example 18 were amplified using oligonucleotides 197 and 938 for the kappa chain sequences, and oligonucleotides 949 and 950 for the heavy chain sequences. PCR was performed using a high-fidelity PCR system, Expand (Roche Molecular Biochemicals, Indianapolis, Ind.). Each 50 μL reaction contained 50 pmol of each primer, 0.35 units of Expand DNA polymerase, 5 μL 2 mM dNTP's, 5 μL 10×Expand reaction buffer, 1 μl diluted (1:20 dilution) phage stock as template, and water to 50 μL. The reaction was carried out as described in Example 22 except twenty cycles was used instead of fifteen in the second part of the thermal profile. The double stranded DNA products were used as template to make single standed DNA as described in Example 3. For each chain, five 100 μL reactions were done using oligonucleotide 938 for the kappa chain and oligonucleotide 939 for the heavy chain, and only 25 cycles of amplification were done instead of 30. The ss-DNA was purified as described in Example 18. The HPLC purified DNA was quantified by absorbance at 260 nm, as described in Example 4, then the DNA was kinased as described in Example 4 except added 6 μL 10×kinase buffer, 2.6 μL 10 mM ATP, and 0.5 μL of polynucleotide kinase to 50 μL of DNA. The kinased heavy and light chain ss-DNA samples were then used to mutate BS46 uracil template as described in Example 7 except the mutagenesis was done on a 1 μg scale instead of 2 μg. Electroporated 1 μL of the mutagenesis DNA into DH12S cells as described in Example 8. The first round antibody phage was generated as described in Example 18. The plates were incubated at 37° C. for 4 hr, then 20° C. overnight. The first round antibody phage was eluted from the plates as described in Example 18.

Prior to functional panning, the antibody phage sample was enriched for polyvalent display using the decapeptide tag on the kappa chain and the 7F11 magnetic latex, as described in Example 18. The first round of functional panning was set up with the VEGF-biotin at $10^{-9}$ M final concentration. After allowing the phage and antigen to reach equilibrium, the phage sample was panned with avidin magnetic latex as described in Example 18. The second and third rounds of panning were set up and finished as described in Example 18 using a final VEGF-biotin concentration of $10^{-8}$ M. After 3 rounds of functional panning, the foreground/background was 67.

Oligonucleotide 197—(SEQ ID NO: 76) 5' TC GCT GCC CAA CCA GCC ATG

Oligonucleotide 938—(SEQ ID NO: 77) 5' GAT GAA GAC AGA TGG TGC AGC CAC AG

Oligonucleotide 939—(SEQ ID NO: 78) 5' GG GAA GAC CGA TGG GCC CTT GGT GGA GGC

Oligonucleotide 949—(SEQ ID NO: 79) 5' TTT ACC CCT GTG GCA AAA GCC

Oligonucleotide 950—(SEQ ID NO: 80) 5' TGG ATA GAC AGA TGG GCC CGT CGT GGT GGC

The antibody phage population was subcloned into the expression vector and electroporated as described in Example 22 with the following changes. The 3' PCR primer used to amplify the antibody gene insert, oligonucleotide 970, was different from primer J. Annealing was done by mixing 1 μL of the T4 digested antibody gene insert (100 ng), 1 μL of the T4 digested vector (100 ng), 1 L of 10×annealing buffer and water to 10 μL, followed by heating at 70° C. for 2 min and slow cooling. The vector and insert were ligated together by adding 1 μL of 10×synthesis buffer, 1 μL T4 DNA ligase, 1 μL diluted T7 DNA polymerase and incubating at 37° C. for 15 min. The ligated DNA was electroporated by diluting 1 μL of the ligated DNA into 2 μL of water, then electroporating 1 μL of the diluted DNA into 40 μL of electrocompetent DH10B cells.

Oligonucleotide 970—(SEQ ID NO:81) 5' GT GAT AAA CTA CCG TA AAG CTF ATC GAT GAT AAG CTG TCA A TTA GTG ATG GTG ATG GTG ATG AGA TTT G The recombinant omniclonal was expressed as described in Example 23. The antibody was purified as follows. The first step in purification uses immobilized metal affinity chromatography (IMAC). Streamline Chelating resin (Amersham Pharmacia Biotech, Piscataway, N.J.) is charged with 0.1 M NiCl$_2$, and then equilibrated in 20 mM Borate, 150 nM NaCl, 10 mM Imidazole, 0.01% NaN$_3$, pH 8.0 buffer. The culture homogenate is adjusted to contain 10 mM Imidazole, using a 5 M Imidazole stock solution. It is then contacted with the Ni-charged resin (1 L culture homogenate per 100 mL resin) in a 2 L Pyrex bottle on a G-10 incubator shaker (New Brunswick Scientific, Edison, N.J.) at room temperature, 160 rpm, for 1 hour. The Fab is captured by means of the high affinity interaction between the nickel ligand and the hexahistidine tag on the Fab heavy chain. Following the batch binding step, the resin is allowed to settle by sedimentation, and the culture homogenate is decanted for disposal. The resin with the bound Fab is then washed three times, each time with 1 L of equilibration buffer for 5 minutes. The sedimentation and decanting method described above is used between washes to recover the resin with the bound Fab. After washing, the resin is packed into a column, and washed further until baseline is established on the UV detector. The Fab is eluted with 20 mM Borate, 150 mM NaCl, 200 mM Imidazole, 0.01% $NaN_3$, pH 8.0 buffer.

The second step in purification uses ion-exchange chromatography (IEC). Q Sepharose FastFlow resin (Amersham Pharmacia Biotech, Piscataway, N.J.) is equilibrated in 20 mM Borate, 250 mM NaCl, 0.01% $NaN_3$, pH 8.0. The IMAC elution pool from the first step is mixed 1:1 with 20 mM Borate, 350 mM NaCl, 0.01% $NaN_3$, pH 8.0. This diluted IMAC pool, now in 20 mM Borate, 250 mM NaCl, 0.01% $NaN_3$, pH 8.0, is loaded onto the IEC column. The load is chased with equilibration buffer to UV baseline. The Fab is collected in the flowthrough pool, while other contaminants bind to the column. The contaminants are stripped from the column with 20 mM Borate, 1 M NaCl, 0.01% $NaN_3$, pH 8.0.

The third step in purification uses protein G chromatography (PGC). Protein G Sepharose FastFlow resin (Amersham Pharmacia Biotech, Piscataway, N.J.) is equilibrated in 20 mM Borate, 150 mM NaCl, 0.01% $NaN_3$, pH 8.0. The IEC flowthrough pool from the second step is loaded onto the PGC column. The column is washed equilibration buffer to UV baseline. The Fab binds to the column by means of high affinity interaction between the protein G ligand and the heavy chain on the Fab, while other contaminants pass through the column. The Fab is eluted with 0.1 M Glycine, 0.01% $NaN_3$, pH 3.0. The elution pool is immediately neutralized to pH 8.0 by addition of 3.3% V/V of 1 M TRIS, pH 10.2 buffer.

Finally, the Fab pool from the third step is concentrated to about 25 mg/mL using a stirred-cell concentrator fitted with a YM10 10 kDa disc membrane (Amicon, Beverly, Mass.). The concentrate is dialyzed overnight into 20 mM Borate, 150 mM NaCl, 0.01% $NaN_3$, pH 8.0 buffer, using 12–14 kDa dialysis tubing (Spectrum, Laguna Hills, Calif.). The concentrated and dialyzed Fab pool is then filtered with a 0.2µ, PES syringe filter (Nalgene, Rochester, N.Y.) and tansferred to storage at 2–8° C.

The concentration of the purified Fab is measured by UV absorbance at 280 nm, using an extinction coefficient of 1.6 mg/(mL.cm). The purity is evaluated using a 4–20% TRIS-Glycine SDS-PAGE gel in an Xcell II system (Novex, San Diego, Calif.), and by means of a G250 Zorbax HPLC column (Hewlett-Packard).

Example 21

Construction of the pBR Expression Vector

An expression vector and a process for the subcloning of monoclonal and polyclonal antibody genes from a phage-display vector has been developed that is efficient, does not substantially bias the polyclonal population, and can select for vector containing an insert capable of restoring antibiotic resistance. The vector is a modified pBR322 plasmid, designated pBRncoH3, that contains an arabinose promoter, ampicillin resistance (beta-lactamase) gene, a partial tetracycline resistance gene, a pelB (pectate lyase) signal sequence, and NcoI and HindIII restriction sites. (FIG. 7). The pBRncoH3 vector can also be used to clone proteins other than Fabs with a signal sequence. A second vector, pBRnsiH3, has been developed for cloning proteins with or without signal sequences, identical to the vector described above except that the pelB signal sequence is deleted and the NcoI restriction site has been replaced with an NsiI site.

The araC regulatory gene (including the araBAD promoter) was amplified from E. coli K-12 strain NL31-001 (a gift from Dr. Nancy Lee at UCSB) by PCR (Example 3) using Taq DNA polymerase (Boehringer Mannheim, Indianapolis, Ind.) with primers A and B (Table 3). Primers A and B contain 20 base-pairs of the BS39 vector sequence at their 5'-ends complementary to the 5' side of the lac promoter and the 5' side of the pelB signal sequence, respectively. Primer A includes an EcoRI restriction site at its 5'-end used later for ligating the ara insert into the pBR vector. The araCparaBAD PCR product was verified by agarose gel electrophoresis and used as template for an asymmetric PCR reaction with primer 'B' in order to generate the anti-sense strand of the insert. The single-stranded product was run on agarose gel electrophoresis, excised, purified with GeneClean (Bio101, San Diego, Calif.), and resuspended in water as per manufacturers recommendations. The insert was kinased with T4 polynucleotide kinase for 45 min at 37° C. The T4 polynucleotide kinase was heat inactivated at 70° C. for 10 min and the insert extracted with an equal volume of phenol/chloroform, followed by chloroform. The DNA was precipitated with ethanol at −20° C. for 30 min. The DNA was pelleted by centrifugation at 14 krpm for 15 min at 4° C., washed with ice-cold 70% ethanol, and dried in vacuo.

The insert was resuspended in water and the concentration determined by $A_260$ using an absorbance of 1.0 for a concentration of 40 µg/ml. The insert was cloned into the phage-display vector BS39 for sequence verification and to introduce the pelB signal sequence in frame with the arabinose promoter (the pelB signal sequence also contains a NcoI restriction site at its 3'-end used later for ligating the ara insert into the pBR vector). The cloning was accomplished by mixing 250 ng of BS39 uracil template (Example 5), 150 ng of kinased araCpBAD insert, and 1.0 µl of 10×annealing buffer in a final volume of 10 µl. The sample was heated to 70° C. for 2 min and cooled over 20 min to room temperature to allow the insert and vector to anneal. The insert and vector were ligated together by adding 1 µl of 10×synthesis buffer, 1 µl T4 DNA ligase (1 U/µl), 1 µl T7 DNA polymerase (1 U/µl) and incubating at 37° C. for 30 min. The reaction was stopped with 90 µl of stop buffer (10 mM Tris pH 8.0, 10 mM EDTA) and 1 µl electroporated (Example 8) into electrocompetent E. coli strain, DH10B, (Life Technologies, Gaithersburg, Md.).

The transformed cells were diluted to 1.0 ml with 2×YT broth and 1 µl, 10 µl, 100 µl plated as described in Example 12. Following incubation overnight at 37° C., individual plaques were picked, amplified by PCR with primers A and B, and checked for full-length insert by agarose gel electrophoresis. Clones with full-length insert were sequenced with primers D, E , F, G (Table 3) and checked against the literature. An insert with the correct DNA sequence was amplified by PCR (Example 3) from BS39 with primers A and C (FIG. 5A) and the products run on agarose gel electrophoresis.

Full-length products were excised from the gel and purified as described previously and prepared for cloning by digestion with EcoRI and NcoI. A pBR lac-based expression vector that expressed a murine Fab was prepared to receive this insert by EcoRI and NcoI digestion. This digestion excised the lac promoter and the entire coding sequence up to the 5'-end of the heavy chain ($C_H1$) constant region (FIG. 5A).

The insert and vector were mixed (2:1 molar ratio) together with 1 μl 10 mM ATP, 1 μl (1U/μl) T4 DNA ligase, 1 μl 10×ligase buffer in a final volume of 10 μl and ligated overnight at 15° C. The ligation reaction was diluted to 20 μl, and 1 μl electroporated into electrocompetent *E. coli* strain, DH10B (Example 8), plated on LB tetracycline (10 μg/ml) plates and grown overnight at 37° C.

Clones were picked and grown overnight in 3 ml LB broth supplemented with tetracycline at 20 μg/ml. These clones were tested for the correct insert by PCR amplification (Example 3) with primers A and C, using 1 μl of overnight culture as template. Agarose gel electrophoresis of the PCR reactions demonstrated that all clones had the araCparaB insert. The vector (plasmid) was purified from each culture by Wizard miniprep columns (Promega, Madison, Wis.) following manufacturers recommendations. The new vector contained the araC gene, the araB promoter, the pelB signal sequence, and essentially the entire $C_H1$ region of the heavy chain (FIG. 5B).

The vector was tested for expression by re-introducing the region of the Fab that was removed by EcoRI and NcoI digestion. The region was amplified by PCR, (Example 3) from a plasmid (20 ng) expressing 14F8 with primers H and I (Table 3). The primers, in addition to having sequence specific to 14F8, contain 20 base-pairs of vector sequence at their 5'-end corresponding to the 3'-end of the pelB signal sequence and the 5'-end of the $C_H1$ region for cloning purposes. The PCR products were run on agarose gel electrophoresis and full-length products excised from the gel and purified as described previously.

The vector was linearized with NcoI and together with the insert, prepared for cloning through the 3'→5' exonuclease activity of T4 DNA polymerase. The insert and NcoI digested vector were prepared for T4 exonuclease digestion by aliquoting 1.0 μg of each in separate tubes, adding 1.0 μl of 10×restriction endonuclease Buffer A (Boehringer Mannheim, Indianapolis, Ind.) and bringing the volume to 9.0 μl with water. The samples were digested for 5 min at 30° C. with 1 μl (1U/μl) of T4 DNA polymerase. The T4 DNA polymerase was heat inactivated by incubation at 70° C. for 15 min. The samples were cooled, briefly spun, and the digested insert (35 ng) and vector (100 ng) mixed together and the volume brought to 10 μl with 1 mM $MgCl_2$. The sample was heated to 70° C. for 2 min and cooled over 20 min to room temperature to allow the complementary 5' single-stranded overhangs of the insert and vector resulting from the exonuclease digestion to anneal together (FIG. 6). The annealed DNA (1.5 μl) was electroporated (Example 8) into 30 μl of electrocompetent *E. coli* strain DH10B.

The transformed cells were diluted to 1.0 ml with 2×YT broth and 1 μl, 10 μl, and 100 μl plated on LB agar plates supplemented with tetracycline (100 μg/ml) and grown overnight at 37° C. The following day, two clones were picked and grown overnight in 2×YT (10 μg/ml tetracycline) at 37° C. To test protein expression driven from the ara promoter, these cultures were diluted 1/50 in 2×YT(tet) and grown to $OD_{600}=1.0$ at which point they were each split into two cultures, one of which was induced by the addition of arabinose to a final concentration of 0.2% (W/V). The cultures were grown overnight at room temperature, and assayed for Fab production by ELISA. Both of the induced cultures were producing approximately 20 μg/ml Fab. There was no detectable Fab in the uninduced cultures.

Initial efforts to clone polyclonal populations of Fab were hindered by backgrounds of undigested vector ranging from 3–13%. This undigested vector resulted in loss of Fab expressing clones due to the selective advantage non-expressing clones have over Fab expressing clones. A variety of means were tried to eliminate undigested vector from the vector preparations with only partial success; examples including: digesting the vector overnight 37° C. with NcoI, extracting, and redigesting the preparation a second time; including spermidine in the NcoI digest; including single-stranded binding protein (United States Biochemical, Cleveland, Ohio) in the NcoI digest; preparative gel electrophoresis. It was then noted that there is a HindIII restriction site in pBR, 19 base-pairs from the 5'-end of the tetracycline promoter. A vector missing these 19 base-pairs is incapable of supporting growth in the presence of tetracycline, eliminating background due to undigested vector.

The ara-based expression vector was modified to make it tetracycline sensitive in the absence of insert. This was done by digesting the pBRnco vector with NcoI and HindIII (Boehringer Mannheim, Indianapolis, Ind.), which removed the entire antibody gene cassette and a portion of the tet promoter (FIG. 5B). The region excised by NcoI/HindIII digestion was replaced with a stuffer fragment of unrelated DNA by ligation as described above. The ligation reaction was diluted to 20 μl, and 1 μl electroporated (Example 8) into electrocompetent *E. coli* strain DH10B, plated on LB ampicillin (100 μg/ml) and incubated at 37° C.

After overnight incubation, transformants were picked and grown overnight in LB broth supplemented with ampicillin (100 μg/ml). The vector (plasmid) was purified from each culture by Wizard (Promega, Madison, Wis.) miniprep columns following manufacturers recommendations. This modified vector, pBRncoH3, is tet sensitive, but still retains ampicillin resistance for growing preparations of the vector.

The antibody gene inserts were amplified by PCR with primers I and J (Table 3) as described in Example 3; primer J containing the 19 base-pairs of the tet promoter removed by HindIII digestion, in addition to 20 base-pairs of vector sequence 3' to the HindIII site for annealing. This modified vector was digested with NcoI/HindIII and, together with the insert, exonuclease digested and annealed as described previously. The tet resistance is restored only in clones that contain an insert capable of completing the tet promoter. The annealed Fab/vector (1 μl) was transformed (Example 8) into 30 μl of electrocompetent *E. coli* strain, DH10B.

The transformed cells were diluted to 1.0 ml with 2×YT broth and 10 μl of $10^{-2}$ and $10^{-3}$ dilutions plated on LB agar plates supplemented with tetracycline at 10 μg/ml to determine the size of the subcloned polyclonal population. This plating also provides and opportunity to pick individual clones from the polyclonal if necessary. The remaining cells were incubated at 37° C. for 1 hr and then diluted 1/100 into 30 ml 2×YT supplemented with 1% glycerol and 20 μg/ml tetracycline and grown overnight at 37° C. The overnight culture was diluted 1/100 into the same media and grown 8 hr at which time glycerol freezer stocks were made for long term storage at −80° C.

The new vector eliminates growth bias of clones containing vector only, as compared to clones with insert. This, together with the arabinose promoter which is completely repressed in the absence of arabinose, allows cultures of transformed organisms to be expanded without biasing the polyclonal antibody population for antibodies that are better tolerated by E. coli until induction.

A variant of this vector was also constructed to clone any protein with or without a signal sequence. The modified vector has the NcoI restriction site and all of the pelB signal-sequence removed. In its place a NsiI restriction site was incorporated such that upon NsiI digestion and then T4 digestion, there is single base added, in frame, to the araBAD promoter that becomes the adenosine residue (A) of the ATG initiation codon. The HindIII site and restoration of the tetracycline promoter with primer J (Table 3) remains the same as described for the pBRncoH3 vector. Additionally, the T4 exonuclease cloning process is identical to that described above, except that the 5' PCR primer used to amplify the insert contains 20 bp of vector sequence at its 5'-end corresponding to 3'-end of the araBAD promoter rather than the 3'-end of the PelB signal sequence.

Three PCR primers, K, L, and M (Table 3) were used for amplifying the araC regulatory gene (including the araBAD promoter). The 5'-primer, primer K, includes an EcoRI restriction site at its 5'-end for ligating the ara insert into the pBR vector. The 3'-end of the insert was amplified using two primers because a single primer would have been too large to synthesize. The inner 3'-primer (L) introduces the NsiI restriction site, in frame, with the araBAD promoter, with the outer 3' primer (M) introducing the HindIII restriction site that will be used for ligating the insert into the vector.

The PCR reaction was performed as in Example 3 on a 4×100 µl scale; the reactions containing 100 pmol of 5' primer (K), 1 pmol of the inner 3' primer (L), and 100 pmol of outer 3' primer (M), 10 µl 2 mM dNTPs, 0.5 µL Taq DNA Polymerase, 10 µl 10×Taq DNA polymerase buffer with MgCl$_2$, and H$_2$O to 100 µL. The araCparaBAD PCR product was precipitated and fractionated by agarose gel electrophoresis and full-length products excised from the gel, purified, resuspended in water, and prepared for cloning by digestion with EcoRI and HindIII as described earlier. The pBR vector (Life Technologies, Gaithersburg, Md.) was prepared to receive this insert by digestion with EcoRI and HindIII and purification by agarose gel electrophoresis as described above.

The insert and vector were mixed (2:1 molar ratio) together with 1 µl 10 mM ATP, 1 µl (1 U/µl) T4 DNA ligase, 1 µl 10×ligase buffer in a final volume of 1 µl and ligated overnight at 15° C. The ligation reaction was diluted to 20 µl, and 1 µl electroporated into electrocompetent E. coli strain, DH10B (Example 8), plated on LB tetracycline (10 µg/ml) plates and grown overnight at 37° C. Clones were picked and grown overnight in 3 ml LB broth supplemented with tetracycline.

These clones were tested for the correct insert by PCR amplification (Example 3) with primers K and M, using 1 µl of overnight culture as template. Agarose gel electrophoresis of the PCR reactions demonstrated that all clones had the araCparaB insert. The vector (plasmid) was purified from each culture by Wizard miniprep columns following manufacturers recommendations. The new vector, pBRnsi contained the araC gene, the araBAD promoter, and a NsiI restriction site.

The vector was tested for expression by introducing a murine Fab. The region was amplified by PCR (Example 3) from a plasmid (20 ng) containing a murine Fab with primers O and N (Table 3). The primers, in addition to having sequence specific to the Fab, contain 20 bp of vector sequence at their 5'-end corresponding to the 3'-end araBAD promoter and the 5'-end of the $C_H1$ region for cloning purposes. The pBRnsi vector was linearized with NsiI and HindIII. The vector and the PCR product were run on an agarose gel, and full-length products were excised from the gel and purified as described previously. The vector and insert were digested with T4 DNA polymerase and annealed as described earlier. The annealed DNA (1 µl) was electroporated (Example 8) into 30 µl of electrocompetent E. coli strain DH10B. The transformed cells were diluted to 1.0 ml with 2×YT broth and 1 µl, 10 µl, and 100 µl plated on LB agar plates supplemented with tetracycline (10 µg/ml) and grown overnight at 37° C.

Nitrocellulose lifts were placed on the placed on the surface of the agar plates for 1 min and processed as described (Section 12.24, Molecular Cloning, A laboratory Manual, (1989) Sambrook. J.). The filters were developed with goat anti-kappa-AP, and a positive (kappa expressing) clone was picked and grown overnight in 2×YT (10 µg/ml tetracycline) at 37° C. The vector (plasmid) was purified from the culture by Wizard miniprep columns (Promega, Madison, Wis.) following manufacturers recommendations. The Fab region was excised by NcoI/HindIII digestion and replaced with a stuffer fragment of unrelated DNA by ligation as described above. The ligation reaction was diluted to 20 µl, and 1 µl electroporated (Example 8) into electrocompetent E. coli strain DH10B, plated on LB ampicillin (100 µg/ml) and incubated at 37° C. After overnight incubation, transformants were picked and grown overnight in LB broth supplemented with ampicillin (100 µg/ml). The vector (plasmid) was purified from each culture by Wizard miniprep columns following manufacturers recommendations. This modified vector, pBRnsiH3, is tet sensitive, but still retains ampicillin resistance for growing preparations of the vector.

Example 22

Subcloning Monoclonal and Polyclonal Fab Populations into Expression Vectors and Electroporation into *Escherichia coli*

The final round of the polyclonal glutamate dehydrogenase antibody phage (see Example 17) was diluted 1/30 in 2×YT (approximately 2×10$^9$/ml) and 1 µl used as template for PCR amplification of the antibody gene inserts with primers I and P (Table 3). PCR (3–100 µL reactions) was performed using a high-fidelity PCR system, Expand (Boehringer Mannheim, Indianapolis, Ind.) to minimize errors incorporated into the DNA product. Each 100 µl reaction contained 100 pmol of 5' primer I, 100 pmol of 3' primer J, 0.7 units of Expand DNA polymerase, 10 µl mM dNTPs, 10 µl 10×Expand reaction buffer, 1 µl diluted phage stock as template, and water to 100 µl. The reaction was carried out in a Perkin-Elmer thermal cycler (Model 9600) using the following thermal profile: one cycle of denaturation at 94° C. (1 min); ten cycles of denaturation (15 sec, 94° C.), annealing (30 sec, 55° C.), elongation (60 sec, 72° C.); fifteen cycles of denaturation (15 sec. 94° C.), annealing (30 sec, 55° C.), elongation (80 sec plus 20 sec for each additional cycle, 72° C.); elongation (6 min, 72° C.); soak (4° C., indefinitely). The PCR products were ethanol precipitated, pelleted and dried as described above. The DNA was dissolved in water and fractionated by agarose gel electrophoresis. Only full-length products were excised from the gel, purified, and resuspended in water as described earlier.

The insert and NcoI/HindIII digested pBRncoH3 vector were prepared for T4 exonuclease digestion by adding 1.0 µl of 10×Buffer A to 1.0 μg of DNA and bringing the final volume to 9 μl with water. The samples were digested for 4 min at 30 C with 1 μl (1U/μl) of T4 DNA polymerase. The T4 DNA polymerase was heat inactivated by incubation at 70° C. for 10 min. The samples were cooled, briefly spun, and 5 μl of the digested antibody gene insert and 2.0 μl of 10×annealing buffer were mixed with 5 μL of digested vector in a 1.5 mL tube. The volume was brought to 20 μl with water, heated to 70° C. for 2 min and cooled over 20 min to room temperature to allow the insert and vector to anneal.

The insert and vector were ligated together by adding 2 μl of 10×synthesis buffer, 2 μl T4 DNA ligase (1U/μl), 2 μl diluted T7 DNA polymerase (1U/μl) and incubating at 37° C. for 30 min. The reaction was stopped with 370 μl of stop buffer (10 mM Tris pH 8.0, 10 mM EDTA), extracted with phenol/chloroform, chloroform, and precipitated from ethanol at −20° C. The reaction was centrifuged and the supernatant aspirated. The sample was briefly spun an additional time and all traces of ethanol removed with a pipetman. The pellet was dried in vacuo.

The DNA was resuspended in 2 μl of water and 1 μl electroporated (Example 8) into 40 μl of electrocompetent *E. coli* strain, DH10B. The transformed cells were diluted to 1.0 ml with 2×YT broth and 10 μl of $10^{-1}$, $10^{-2}$ and $10^{-3}$ dilutions plated on LB agar plates supplemented with tetracycline at 10 μg/ml to determine the size of the subcloned polyclonal population. The remaining cells were incubated at 37° C. for 1 hr and then diluted 1/100 into 30 ml 2×YT supplemented with 1% glycerol and 20 μg/ml tetracycline and grown overnight at 37° C. The overnight culture was diluted 1/100 into the same media, grown 8 hr, and glycerol freezer stocks made for long term storage at −80° C. The polyclonal antibody was designated CD.43.5. PC.

The monoclonal antibody to glutamate dehydrogenase (Example 17) was also subcloned following the same general procedure described above. The subcloned monoclonal antibody was designated CD.43.9. The polyclonal antibody phage stock for *Clostridium difficile* toxin A (Example 15) was subcloned in a similar way. The subcloned polyclonal antibody was designated CD.TXA.1.PC.

Example 23

Growth of *E. coli* Cultures and Purification of Recombinant Antibodies and Antigens A shake flask inoculum is generated overnight from a −70° C. cell bank in an Innova 4330 incubator shaker (New Brunswick Scientific, Edison, N.J.) set at 37° C., 300 rpm. The inoculum is used to seed a 20 L fermenter (Applikon, Foster City, Calif.) containing defined culture medium (Pack, et al., Bio/Technology 11:1271–1277 (1993)) supplemented with 3 g/L L-leucine, 3 g/L L-isoleucine, 12 g/L casein digest (Difco, Detroit, Mich.), 12.5 g/L glycerol and 10 mg/ml tetracycline. The temperature, pH and dissolved oxygen in the fermenter are controlled at 26° C., 6.0–6.8 and 25% saturation, respectively. Foam is controlled by addition of polypropylene glycol (Dow, Midland, Mich.). Glycerol is added to the fermenter in a fed-batch mode. Fab expression is induced by addition of L(+)-arabinose (Sigma, St. Louis, Mo.) to 2 g/L during the late logarithmic growth phase. Cell density is measured by optical density at 600 nm in an UV-1201 spectrophotometer (Shimadzu, Columbia, Md.). Final Fab concentrations are typically 100–500 mg/L. Following run termination and adjustment of pH to 6.0, the culture is passed twice through an M-210B-EH Microfluidizer (Microfluidics, Newton, Mass.) at 17000 psi. The high pressure homogenization of the cells releases the Fab into the culture supernatant.

The first step in purification is expanded bed immobilized metal affinity chromatography (EB-IMAC). Streamline Chelating resin (Pharmacia, Piscataway, N.J.) is charged with 0.1 M $NiCl_2$. It is then expanded and equilibrated in 50 mM acetate, 200 mM NaCl, 10 mM imidazole, 0.01% $NaN_3$, pH 6.0 buffer flowing in the upward direction. A stock solution is used to bring the culture homogenate to 10 mM imidazole, following which, it is diluted two-fold or higher in equilibration buffer to reduce the wet solids content to less than 5% by weight. It is then loaded onto the Streamline column flowing in the upward direction at a superficial velocity of 300 cm/hr. The cell debris passes through unhindered, but the Fab is captured by means of the high affinity interaction between nickel and the hexahistidine tag on the Fab heavy chain. After washing, the expanded bed is converted to a packed bed and the Fab is eluted with 20 mM borate, 150 mM NaCl, 200 mM imidazole, 0.01% $NaN_3$, pH 8.0 buffer flowing in the downward direction. The second step in purification uses ion-exchange chromatography (IEC). Q Sepharose FastFlow resin (Pharmacia, Piscataway, N.J.) is equilibrated in 20 mM borate, 37.5 mM NaCl, 0.01% $NaN_3$, pH 8.0. The Fab elution pool from the EB-IMAC step is diluted four-fold in 20 mM borate, 0.01% $NaN_3$, pH 8.0 and loaded onto the IEC column. After washing, the Fab is eluted with a 37.5–200 mM NaCl salt gradient. The elution fractions are evaluated for purity using an Xcell II SDS-PAGE system (Novex, San Diego, Calif.) prior to pooling. Finally, the Fab pool is concentrated and diafiltered into 20 mM borate, 150 mM NaCl, 0.01% $NaN_3$, pH 8.0 buffer for storage. This is achieved in a Sartocon Slice system fitted with a 10,000 MWCO cassette (Sartorius, Bohemia, N.Y.). The final purification yields are typically 50%. The concentration of the purified Fab is measured by UV absorbance at 280 nm, assuming an absorbance of 1.6 for a 1 mg/mL solution.

Example 24

Expression of Antigen or Antibodies in Shake Flasks and Purification

A shake flask inoculum is generated overnight from a −70° C. cell bank in an incubator shaker set at 37° C., 300 rpm. The cells are cultured in a defined medium described above. The inoculum is used to seed a 2 L Tunair shake flask (Shelton Scientific, Shelton, Conn.) which is grown at 37° C., 300 rpm. Expression is induced by addition of L(+)-arabinose to 2 g/L during the logarithmic growth phase, following which, the flask is maintained at 23° C., 300 rpm. Following batch termination, the culture is passed through an M-110Y Microfluidizer (Microfluidics, Newton, Mass.) at 17000 psi. The homogenate is clarified in a J2-21 centrifuge (Beckman, Fullerton, Calif.).

Purification employs immobilized metal affinity chromatography. Chelating Sepharose FastFlow resin (Pharmacia, Piscataway, N.J.) is charged with 0.1 M $NiCl_2$ and equilibrated in 20 mM borate, 150 mM NaCl, 10 mM imidazole, 0.01% $NaN_3$, pH 8.0 buffer. A stock solution is used to bring the culture supernatant to 10 mM imidazole. The culture supernatant is then mixed with the resin and incubated in the incubator shaker set at room temperature, 150–200 rpm. The antigen is captured by means of the high affinity interaction between nickel and the hexahistidine tag on the antigen. The culture supernatant and resin mixture is poured into a chromatography column. After washing, the antigen is eluted with 20 mM borate, 150 mM NaCl, 200 mM imidazole, 0.01% $NaN_3$, pH 8.0 buffer. The antigen pool is concentrated in a stirred cell fitted with a 10,000 MWCO membrane (Amicon, Beverly, Mass.). It is then dialysed overnight into 20 mM borate, 150 mM NaCl, 0.01% $NaN_3$, pH 8.0 for storage, using 12–14,000 MWCO dialysis tubing. The purified antigen is evaluated for purity by SDS-PAGE analysis. A yield of 150 mg of purified antigen per liter of shake flask culture is expected. The concentration of the *C. difficile* glutamate dehydrogenase antigen is based on UV absorbance at 280 nm, assuming an absorbance of 1.48 for a 1 mg/mL solution. Antibody shake flask expression and purification is done as described for antigen.

Example 25

Preparation of 7F11 Monoclonal Antibody
Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 min, under argon, a solution of 1-acetylimidazole (9.6 g, 0.087 moles) in THF (100 ml). The solution was allowed to stir a further 3 hr at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44–45° C.

Decapeptide Derivatives

The decapeptide, YPYDVPDYAS,(SEQ IDS NO: 82) (Chiron Mimotopes Peptide Systems, San Diego, Calif.) was dissolved (0.3 g) in dry DMF (5.4 mL) in a round bottom flask under argon with moderate stirring. Imidazole (0.02 g) was added to the stirring solution. Separately, acetylthiopropionic acid (0.041 g) was dissolved in 0.55 mL of dry DMF in a round bottom flask with stirring and 0.056 g of 1,1'-carbonyldiimidazole (Aldrich Chemical Co., Milwaukee, Wis.) was added to the stirring solution. The flask was sealed under argon and stirred for at least 30 min at room temperature. This solution was added to the decapeptide solution and the reaction mixture was stirred for at least six hr at room temperature before the solvent was removed in vacuo. The residue in the flask was triturated twice using 10 mL of diethyl ether each time and the ether was decanted. Methylene chloride (20 mL) was added to the residue in the flask and the solid was scraped from the flask and filtered using a fine fritted Buchner funnel. The solid was washed with an additional 20 mL of methylene chloride and the Buchner funnel was dried under vacuum. In order to hydrolyze the derivative to generate a free thiol, it was dissolved in 70% DMF and 1 M potassium hydroxide was added to a final concentration of 0.2 M while mixing vigorously. The derivative solution was allowed to stand for 5 min at room temperature prior to neutralization of the solution by the addition of a solution containing 0.5 M potassium phosphate, 0.1 M borate, pH 7.0, to which concentrated hydrochloric acid has been added to a final concentration of 1 M. The thiol concentration of the hydrolyzed decapeptide derivative was determined by diluting 10 µL of the solution into 990 µL of a solution containing 0.25 mM 5,5'-dithiobis (2-nitrobenzoic acid) (DTNB, Aldrich Chemical Co., Milwaukee Wis.) and 0.2 M potassium borate, pH 8.0. The thiol concentration in mM units was equal to the A412(100/13.76).

Preparation of Conjugates of Decapeptide Derivative with Keyhole Limpet Hemocyanin and Bovine Serum Albumin Keyhole limpet hemocyanin (KLH, 6 ml of 14 mg/ml, Calbiochem, San Diego, Calif.) was reacted with sulfosuccinimidyl 4-(N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hr at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The hydrolyzed decapeptide derivative was separately added to portions of the KLH-maleimide in substantial molar excess over the estimated maleimide amounts present and the solution was stirred for 4 hr at 4° C. and then each was dialyzed against 3 volumes of one liter of pyrogen-free phosphate-buffered saline, pH7.4, prior to immunization.

Bovine serum albumin (BSA, 3.5 ml of 20 mg/ml) was reacted with SMCC by adding a solution of 6.7 mg of SMCC in 0.3 ml acetonitrile and stirring the solution for one hr at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The hydrolyzed decapeptide derivative was separately added to portions of the BSA-maleimide in substantial molar excess over the estimated maleimide amounts present and the solution was stirred for 4 hr at 4° C. The solutions were used to coat microtiter plates for the detection of antibodies that bound to the decapeptide derivative by standard techniques.

Production and Primary Selection of Monoclonal Antibodies

Immunization of Balb/c mice was performed according to the method of Liu, et al. *Clin Chem* 25:527–538 (1987). Fusions of spleen cells with SP2/0-Ag 14 myeloma cells, propagation of hybridomas, and cloning were performed by standard techniques. Selection of hybridomas for further cloning began with culture supernatant at the 96-well stage. A standard ELISA procedure was performed with a BSA conjugate of decapeptide derivative adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not linked to the decapeptide derivative identified which of the positive clones that bound the BSA conjugates were actually binding the SMCC-BSA. The antibodies specific for SMCC-BSA may be eliminated at this step. Monoclonal antibody 7F11, specific for the decapeptide derivative, was produced and selected by this process.

Example 26

Preparation of 7F11 Magnetic Latex

MAG/CM-BSA

To 6 mL of 5% magnetic latex (MAG/CM, 740 µm 5.0%, Seradyn, Indianapolis, Ind.) was added 21 ML of water followed by 3 mL of 600 mM 2-(4-morpholino)-ethane sulfonic acid, pH 5.9 (MES, Fisher Scientific, Pittsburgh, Pa.). Homocysteine thiolactone hydrochloride (HCTL, 480mg, Aldrich Chemical Co., Milwaukee, Wis.) and 1-(3-Dimethylaminopropyl)-3-ethylcarbodiimide (EDAC, 660 mg, Aldrich Chemical Co., Milwaukee, Wis.) were added in succession, and the reaction mixture was rocked at room temperature for 2 h. The derivatized magnetic latex was washed 3 times with 30 mL of water (with magnet as in Example 14) using probe sonication to resuspend the particles. The washed particles were resuspended in 30 mL of water. Three mL of a solution containing sodium hydroxide (2M) and EDTA (1 mM) was added to the magnetic latex-HCTL suspension, and the reaction proceeded at room temperature for 5 min. The pH was adjusted to 6.9 with 6.45 mL of 1 M hydrochloric acid in 500 mM sodium phosphate, 100 mM sodium borate. The hydrolyzed magnetic latex-HCTL was separated from the supernate with the aid of a magnet, and then resuspended in 33 mL of 50 mM sodium phosphate, 10 mM sodium borate, 0.1 mM EDTA, pH 7.0. The magnetic latex suspension was then added to 2 mL of 36 mg mL-1 BSA-SMCC (made as described in Example 21 with a 5-fold molar excess of SMCC over BSA), and the reaction mixture was rocked overnight at room temperature. N-Hydroxyethylmaleimide (NHEM, 0.42 mL of 500 mM, Organix Inc., Woburn, Mass.) was added to cap any remaining thiols for 30min. After 30 min, the magnetic latex-BSA was washed twice with 30 mL of 50 mM potassium phosphate, 10 mM potassium borate, 150 mM sodium chloride, pH 7.0 (50/10/150) and twice with 30 mL of 10 mM potassium phosphate, 2 mM potassium borate, 200 mM sodium thiocyanate, pH 7.0 (10/2/200). The magnetic latex-BSA was resuspended in 30 mL of 10/2/200.

7F11-SH (1:5)

To a solution of 7F11 (3.8 mL of 5.85 mg mL$^{-1}$) was added 18 $\mu$L of SPDP (40 mM in acetonitrile). The reaction proceeded at room temperature for 90 min after which taurine (Aldrich Chemical Co., Milwaukee, Wis.) was added to a final concentration of 20 mM. Fifteen min later DTT was added to a final concentration of 2 mM, and the reduction reaction proceeded at room temperature for 30 min. The 7F11-SH was purified on G-50 (40 mL) that was eluted with 50/10/150 plus 0.1 mM EDTA. The pool of purified 7F11-SH was reserved for coupling to the MAG/CM-BSA-SMCC.

MAG/CM-BSA-7F11

SMCC (10 mg) was dissolved in 0.5 mL of dry dimethylformamide (Aldrich Chemical Co., Milwaukee, Wis.), and this solution was added to the magnetic latex-BSA suspension. The reaction proceeded at room temperature with gentle rocking for 2 h. Taurine was added to a final concentration of 20 mM. After 20 min the magnetic latex-BSA-SMCC was separated from the supernate with the aid of a magnet and then resuspended in 10/2/200 (20 mL) with probe sonication. The magnetic latex was purified on a column of Superflow-6 (240 mL, Sterogene Bioseparations Inc., Carlsbad, Calif.) that was eluted with 10/2/200. The buffer was removed, and to the magnetic latex cake was added 30 mL of 0.7 mg mL$^{-7}$F11-SH. The reaction mixture was rocked overnight at room temperature. After 20 hr the reaction was quenched with mercaptoethanol (2 mM, Aldrich Chemical Co., Milwaukee, Wis.) followed by NHEM (6 mM). The MAG/CM-7F11 was washed with 10/2/200 followed by 50/10/150. The magnetic latex was then resuspended in 30 mL of 50/10/150.

Table 3

PCR and Sequencing Primer Sequence

A—(SEQ ID NO: 83) 5'(CACTCAACCCTATCTATTAATGTGGAATTCAA ATGGACGAAGCAGGGATT)
B—(SEQ ID NO: 84) 5'(GTAGGCAATAGGTATTTCATCGTTTCACTCCA TCCAAA)
C—(SEQ ID NO: 85) 5'(TCCGTGCCGGTTGTGAAG)
D—(SEQ ID NO: 86) 5'(TACGCGAGGCTTGTCAGT)
E—(SEQ ID NO: 87) 5'(TTCATCACTACGGTCGTC)
F—(SEQ ID NO: 88) 5'(ACGGCAATGTCTGATGC)
G—(SEQ ID NO: 89) 5'(GATATCAACGTTTATCTAATCAGGCCATGGC TGGTTGGGCAG)
H—(SEQ ID NO: 90) 5'(GGCATCCCAGGGTCACCATG)
I—(SEQ ID NO: 91) 5'(TCGCTGCCCAACCAGCCATG)
J—(SEQ ID NO: 92) 5=(GTGATAAACTACCGCATTAAAGCTTATCGA TGATAAGCTGTCAATTAAGAATCC CTGGGCACAATTTTC)
K—(SEQ ID NO: 93) 5'(AGAGCTGCAGAATTCAGCTGATCATCTACC AATAAAAAACGCCCGGCGGCAAC CGAGCGT-TCTGAACAAATGGACGAAGCAGGG ATTC)
L—(SEQ ID NO: 94) 5'(TCTCTCCAAGGAAGCTTAAAAAAAAGCCCG CTCATTAGGCGGGCTAGCTTAATCAA TCATGCATCGTTTCACTCCATCCAAAAAAAC)
M—(SEQ ID NO: 95) 5'(ACAGGTACGAAGCTTATCGATGATAAGCTGT CAAACCAAGGAGCTTAAAAAAAA GCCCGCTCATTAGGC)
N—(SEQ ID NO: 96) 5'(ACCCGTTTTTTTGGATGGAGTGAAACGATGC ATTACCTATTGCCTACGGCA)
O—(SEQ ID NO: 97) 5'(GTGATAAACTACCGCATTAAAGCTTATCGATG ATAAGCTGTCAATTAAGAAGCG TAGTAGTCCG-GAACGTC
P—(SEQ ID NO: 98) 5'(GTGATAAACTACCGCATTAAAGCTTATCGATG ATAAGCTGTCAATTAGTGATGGT GATGGTGAT-GACAATCC
Q—(SEQ ID NO: 99) 5'(ACCCGTTTTTTTGGATGGAGTGAAACGATGT CAGGAAAAGATGTAAATGTC)
R—(SEQ ID NO: 100) 5'(GTGATAAACTACCGCATTAAAGCTTATCGAT GATAAGCTGTCAATTAGTGATGGTGA TGGTGATGGTACCATCCTCTTAATTTCATAGC)

Note: restriction enzyme sites are in bold type.

GAATTC=EcoRI
CCATGG=NcoI
AAGCTT=HindIII

What is claimed is:

1. A method of producing a chimeric antibody library having affinity for a target, comprising:

providing a library of replicable genetic packages, wherein a member comprises a replicable genetic package capable of displaying an antibody chain encoded by a genome of the package and the antibody chain varying between members, and wherein the library of replicable genetic packages has been selected from a primary library of replicable genetic packages by affinity selection to a target;

subcloning a mixed population of DNA molecules encoding at least four different antibody chains of the library of replicable genetic packages into multiple copies of an expression vector to produce modified forms of the expression vector; and introducing the modified forms of the expression vector into a host and expressing the antibody chains as chimeric antibody chains in the host, wherein a library of at least four different chimeric antibody chains are expressed, at least 90% of modified forms of the expression vector encode chimeric antibody chains having specific affinity for the target and no modified form of the expression vector constitutes more than 50% of the total forms.

2. The method of claim 1, wherein the antibody chains comprise variable regions from a first species and the expression vector encodes a constant domain from a second species which is expressed in-frame with the antibody chains subcloned from the library of replicable genetic packages to form the chimeric antibody chains.

3. The method of claim 1, wherein the antibody chains encoded by the genome of the package are chimeric antibody chains comprising a variable region from a first species and a constant region from a second species.

4. The method of claim 2 or 3, wherein the variable regions are nonhuman variable regions, and the constant region is a human constant region.

5. The method of claim 1, wherein the antibody chains encoded by the genome of the package are chimeric antibody chains, a chimeric antibody chain comprising a variable region from a first species and a first segment of a constant region from a second species, and the expression vector encodes a second segment of the constant region of the second species, which is expressed in-frame with the first segment of the constant region.

6. The method of claim 5, wherein the antibody chains are heavy chains, the first segment comprises a $C_H1$ region, and the second segment comprises a hinge, $C_H2$ and $C_H3$ regions.

7. The method of claim 1, further comprising releasing the polypeptides from the host.

8. The method of claim 1, wherein the antibody chain encoded by the replicable genetic package comprises an antibody heavy or light chain variable domain, and in at least some library members, the heavy or light chain variable domain is respectively complexed with a partner light or heavy chain antibody variable domain to form a Fab fragment, and the subcloning comprises subcloning a mixture of DNA molecules encoding at least four different antibodies chains and their respective partner into multiple copies of an expression vector, whereby each copy encodes an antibody chain and its partner, and the antibody chains and their partners are expressed as chimeric chains and complex to form chimeric Fab fragments.

9. The method of claim 8, wherein the host cells are procaryotic and the antibody heavy or light chain variable domain and the partner heavy or light chain variable domain are expressed as chimeric antibody chains from the same promoter in the expression vector as a polycistronic message.

10. The method of claim 1, wherein the mixed population of DNA molecules encodes at least 10 different antibody chains and a library of at least 10 different chimeric antibody chains are expressed in the host.

11. The method of claim 1, wherein the mixed population of DNA molecules encodes at least 10 different antibody chains and a library of at least 100 different chimeric antibody chains are expressed in the host.

12. The method of claim 1, wherein at least 95% of the modified form of the expression vector encode chimeric antibody chains having specific affinity for the target.

* * * * *